(12) United States Patent
Tsai et al.

(10) Patent No.: US 8,784,485 B2
(45) Date of Patent: Jul. 22, 2014

(54) METHOD AND DEVICE FOR INSERTING AN INTRAOCULAR LENS

(71) Applicant: Visiogen, Inc., Santa Ana, CA (US)

(72) Inventors: George Tsai, Mission Viejo, CA (US); Tuan Anh Nguyen, Orange, CA (US); Phu Nguyen, Lake Forest, CA (US); Scott Evans, Santa Ana, CA (US)

(73) Assignee: Visiogen, Inc., Santa Ana, CA (US)

( * ) Notice: Subject to any disclaimer, the term of this patent is extended or adjusted under 35 U.S.C. 154(b) by 0 days.

(21) Appl. No.: 13/865,019

(22) Filed: Apr. 17, 2013

(65) Prior Publication Data

US 2013/0304077 A1 Nov. 14, 2013

Related U.S. Application Data

(62) Division of application No. 12/047,259, filed on Mar. 12, 2008, now Pat. No. 8,425,595.

(51) Int. Cl.
*A61F 2/16* (2006.01)
*A61F 9/00* (2006.01)

(52) U.S. Cl.
USPC .......................................... 623/6.12; 606/107

(58) Field of Classification Search
USPC ........................... 606/107, 108, 166; 623/6.12
See application file for complete search history.

(56) References Cited

U.S. PATENT DOCUMENTS

| | | | |
|---|---|---|---|
| 4,240,163 A | 12/1980 | Galin | |
| 4,409,691 A | 10/1983 | Levy | |
| 4,636,210 A | 1/1987 | Hoffer | |
| 4,655,770 A | 4/1987 | Gupta et al. | |
| 4,666,445 A | 5/1987 | Tillay | |
| 4,681,102 A | 7/1987 | Bartell | |
| 4,702,244 A | 10/1987 | Mazzocco | |
| 4,731,079 A | 3/1988 | Stoy | |
| 4,790,847 A | 12/1988 | Woods | |
| 4,834,094 A | 5/1989 | Patton et al. | |

(Continued)

FOREIGN PATENT DOCUMENTS

| | | |
|---|---|---|
| DE | 19501444 | 7/1996 |
| DE | 10015472 | 11/2001 |

(Continued)

OTHER PUBLICATIONS

2004/0160575, Prosecution Events: Office Action: Oct. 11, 2006, Mar. 30, 2007, Jul. 30, 2007, Nov. 1, 2007, Jun. 13, 2008, Amendments: Jan. 11, 2007, Apr. 30, 2007, Aug. 24, 2007, Feb. 29, 2008, Sep. 15, 2008.

(Continued)

*Primary Examiner* — Ashley Fishback
(74) *Attorney, Agent, or Firm* — Visiogen, Inc.

(57) ABSTRACT

An injector for inserting an intraocular lens into an eye includes a lumen. The lumen can include a terminal portion at a distal end and a proximal portion juxtaposed with the terminal portion. An injector plunger can be disposed within the lumen for generating a driving force on the intraocular lens. The injector can include a lens frictional force that has a first value when the lens is at a first location within the proximal portion and a second value when the lens is at a second location within the terminal portion. The first value can be smaller than the second value. In some embodiments, the lens frictional force increases abruptly from the first value to the second value as the lens approaches the distal end of the lumen.

20 Claims, 49 Drawing Sheets

(56) References Cited

U.S. PATENT DOCUMENTS

| | | |
|---|---|---|
| 4,842,601 A | 6/1989 | Smith |
| 4,862,885 A | 9/1989 | Cumming |
| 4,883,485 A | 11/1989 | Patel |
| 4,888,012 A | 12/1989 | Horn et al. |
| 4,892,543 A | 1/1990 | Turley |
| 4,902,024 A | 2/1990 | Takenoshita |
| 4,919,130 A | 4/1990 | Stoy et al. |
| 4,932,966 A | 6/1990 | Christie et al. |
| 4,963,148 A | 10/1990 | Sulc et al. |
| 4,994,082 A | 2/1991 | Richards et al. |
| 5,098,439 A | 3/1992 | Hill et al. |
| 5,123,905 A | 6/1992 | Kelman |
| 5,171,319 A | 12/1992 | Keates et al. |
| 5,190,552 A | 3/1993 | Kelman |
| 5,190,553 A | 3/1993 | Kanert et al. |
| 5,275,604 A | 1/1994 | Rheinish et al. |
| 5,275,623 A | 1/1994 | Sarfarazi |
| 5,281,227 A | 1/1994 | Sussman |
| 5,326,347 A | 7/1994 | Cumming |
| 5,354,335 A | 10/1994 | Lipshitz et al. |
| 5,425,734 A | 6/1995 | Blake |
| 5,443,506 A | 8/1995 | Garabet |
| 5,468,246 A | 11/1995 | Blake |
| 5,474,562 A | 12/1995 | Orchowski et al. |
| 5,476,514 A | 12/1995 | Cumming |
| 5,494,484 A | 2/1996 | Feingold |
| 5,496,328 A | 3/1996 | Nakajima et al. |
| 5,499,987 A | 3/1996 | Feingold |
| 5,507,806 A | 4/1996 | Blake |
| 5,578,081 A | 11/1996 | McDonald |
| 5,607,472 A | 3/1997 | Thompson |
| 5,616,148 A | 4/1997 | Eagles et al. |
| 5,620,450 A | 4/1997 | Eagles et al. |
| 5,653,754 A | 8/1997 | Nakajima et al. |
| 5,728,102 A | 3/1998 | Feingold |
| 5,735,858 A | 4/1998 | Makker et al. |
| 5,800,442 A | 9/1998 | Wolf et al. |
| 5,807,400 A | 9/1998 | Chambers et al. |
| 5,860,984 A | 1/1999 | Chambers et al. |
| 5,873,879 A | 2/1999 | Figueroa et al. |
| 5,876,440 A | 3/1999 | Feingold |
| 5,921,989 A | 7/1999 | Deacon et al. |
| 5,928,245 A | 7/1999 | Wolf et al. |
| 5,941,886 A | 8/1999 | Feingold |
| 5,944,725 A | 8/1999 | Cicenas et al. |
| 5,947,975 A | 9/1999 | Kikuchi et al. |
| 5,968,094 A | 10/1999 | Werblin et al. |
| 5,984,962 A | 11/1999 | Anello et al. |
| 6,010,510 A | 1/2000 | Brown et al. |
| 6,013,101 A | 1/2000 | Israel |
| 6,056,758 A | 5/2000 | Vidal et al. |
| 6,083,230 A | 7/2000 | Makker et al. |
| 6,106,554 A | 8/2000 | Bretton |
| 6,117,171 A | 9/2000 | Skottun |
| 6,129,733 A | 10/2000 | Brady et al. |
| 6,162,229 A | 12/2000 | Feingold et al. |
| 6,176,878 B1 | 1/2001 | Gwon et al. |
| 6,179,843 B1 | 1/2001 | Weiler |
| 6,197,058 B1 | 3/2001 | Portney |
| 6,197,059 B1 | 3/2001 | Cumming |
| 6,203,549 B1 | 3/2001 | Waldock |
| 6,217,612 B1 | 4/2001 | Woods |
| 6,228,094 B1 | 5/2001 | Erdman |
| 6,231,603 B1 | 5/2001 | Lang et al. |
| 6,248,111 B1 | 6/2001 | Glick et al. |
| 6,258,123 B1 | 7/2001 | Young et al. |
| 6,280,449 B1 | 8/2001 | Blake |
| 6,280,471 B1 | 8/2001 | Peyman et al. |
| RE37,387 E | 9/2001 | Brady et al. |
| 6,283,975 B1 | 9/2001 | Glick et al. |
| 6,299,641 B1 | 10/2001 | Woods |
| 6,334,862 B1 | 1/2002 | Vidal et al. |
| 6,423,094 B1 | 7/2002 | Sarfarazi |
| 6,443,985 B1 | 9/2002 | Woods |
| 6,450,642 B1 | 9/2002 | Jethmalani et al. |
| 6,454,802 B1 | 9/2002 | Bretton et al. |
| 6,464,725 B2 | 10/2002 | Skottun |
| 6,468,282 B2 | 10/2002 | Kikuchi et al. |
| 6,488,708 B2 | 12/2002 | Sarfarazi |
| 6,497,708 B1 | 12/2002 | Cumming |
| 6,500,181 B1 | 12/2002 | Portney |
| 6,503,275 B1 | 1/2003 | Cumming |
| 6,551,354 B1 | 4/2003 | Ghazizadeh et al. |
| 6,558,420 B2 | 5/2003 | Green |
| 6,605,093 B1 | 8/2003 | Blake |
| 6,761,737 B2 | 7/2004 | Zadno-azizi et al. |
| 6,764,511 B2 | 7/2004 | Zadno-azizi et al. |
| 6,786,934 B2 | 9/2004 | Zadno-azizi et al. |
| 6,818,158 B2 | 11/2004 | Pham et al. |
| 6,846,326 B2 | 1/2005 | Zadno-azizi et al. |
| 6,858,040 B2 | 2/2005 | Nguyen et al. |
| 6,884,261 B2 | 4/2005 | Zadno-azizi et al. |
| 6,899,732 B2 | 5/2005 | Zadno-azizi et al. |
| 6,923,815 B2 | 8/2005 | Brady et al. |
| 7,041,134 B2 | 5/2006 | Nguyen et al. |
| 7,087,080 B2 | 8/2006 | Zadno-azizi et al. |
| 7,097,660 B2 | 8/2006 | Portney |
| 7,118,596 B2 | 10/2006 | Zadno-azizi et al. |
| 7,125,422 B2 | 10/2006 | Woods et al. |
| 7,198,640 B2 | 4/2007 | Nguyen |
| 7,226,478 B2 | 6/2007 | Ting et al. |
| 7,452,362 B2 | 11/2008 | Zadno-azizi et al. |
| 7,452,378 B2 | 11/2008 | Zadno-azizi et al. |
| 2001/0020171 A1 | 9/2001 | Heyman et al. |
| 2002/0002404 A1 | 1/2002 | Sarfarazi |
| 2002/0004682 A1 | 1/2002 | Zhou et al. |
| 2002/0077633 A1 | 6/2002 | Kikuchi et al. |
| 2002/0082609 A1 | 6/2002 | Green |
| 2002/0138140 A1 | 9/2002 | Hanna |
| 2002/0188351 A1 | 12/2002 | Laguette |
| 2003/0018384 A1 | 1/2003 | Valyunin et al. |
| 2003/0078657 A1 | 4/2003 | Zadno-azizi et al. |
| 2003/0078658 A1 | 4/2003 | Zadno-azizi |
| 2003/0114927 A1 | 6/2003 | Nagamoto |
| 2003/0158560 A1 | 8/2003 | Portney |
| 2003/0187504 A1 | 10/2003 | Weinschenk, III et al. |
| 2004/0059343 A1 | 3/2004 | Shearer et al. |
| 2004/0160575 A1 | 8/2004 | Ayton et al. |
| 2005/0182419 A1 | 8/2005 | Tsai |
| 2005/0228401 A1 | 10/2005 | Zadno-Azizi et al. |
| 2005/0234547 A1 | 10/2005 | Nguyen et al. |
| 2005/0251236 A1 | 11/2005 | Jeannin et al. |
| 2006/0100703 A1 | 5/2006 | Evans et al. |
| 2006/0178741 A1 | 8/2006 | Zadno-Azizi et al. |
| 2006/0184244 A1 | 8/2006 | Nguyen et al. |
| 2006/0259139 A1 | 11/2006 | Zadno-Azizi et al. |
| 2006/0271187 A1 | 11/2006 | Zadno-Azizi et al. |
| 2007/0027540 A1 | 2/2007 | Zadno-Azizi et al. |
| 2007/0032866 A1 | 2/2007 | Portney et al. |
| 2007/0050023 A1 | 3/2007 | Bessiere et al. |
| 2007/0050025 A1 | 3/2007 | Nguyen et al. |
| 2008/0027461 A1 | 1/2008 | Vaquero et al. |
| 2008/0045971 A1 | 2/2008 | Ayton et al. |
| 2008/0125790 A1 | 5/2008 | Tsai et al. |
| 2009/0005788 A1 | 1/2009 | Rathert |
| 2009/0030425 A1 | 1/2009 | Smiley et al. |
| 2009/0112313 A1 | 4/2009 | Mentak |
| 2010/0076449 A1 | 3/2010 | Tsai |
| 2010/0106160 A1 | 4/2010 | Tsai |

FOREIGN PATENT DOCUMENTS

| | | |
|---|---|---|
| EP | 0162573 | 11/1985 |
| EP | 0337390 A2 | 10/1989 |
| EP | 0336877 | 10/1993 |
| EP | 1114623 | 11/2001 |
| EP | 1481652 | 12/2004 |
| EP | 1736118 | 12/2006 |
| FR | 2900570 | 11/2007 |
| JP | S61-279241 | 12/1986 |
| JP | 02-126847 | 5/1990 |

(56) References Cited

FOREIGN PATENT DOCUMENTS

| | | |
|---|---|---|
| JP | H03-137325 | 6/1991 |
| WO | WO 95/13022 | 5/1995 |
| WO | WO 96/29956 | 10/1996 |
| WO | WO 98/12969 | 4/1998 |
| WO | WO 99/20206 | 4/1999 |
| WO | WO 99/21513 | 6/1999 |
| WO | WO 00/21467 | 4/2000 |
| WO | WO 00/27315 | 5/2000 |
| WO | WO 00/61036 | 10/2000 |
| WO | WO 00/66037 | 11/2000 |
| WO | WO 01/19289 | 3/2001 |
| WO | WO 01/34067 | 5/2001 |
| WO | WO 01/64136 | 9/2001 |
| WO | WO 01/66042 | 9/2001 |
| WO | WO 03/015657 | 2/2003 |
| WO | WO 2004/000171 | 12/2003 |
| WO | WO 2004/073560 | 9/2004 |
| WO | WO 2007/080868 | 7/2007 |

OTHER PUBLICATIONS

2005/0182419, Prosecution Events: Office Action: Sep. 12, 2008, Dec. 1, 2008, Amendments: Nov. 12, 2008.

2005/0228401, Prosecution Events: Office Action: Oct. 8, 2008.

2008/0125790, and its entire prosecution history.

2008/0045971, and its entire prosecution history.

2010/0076449, and its entire prosecution history.

Tsutomu Hara et al., "Accommodative Intraocular Lens with Spring Action Part 1. Design and Placement in an Excised Animal Eye," Opthalmic Surgery, Feb. 1990, vol. 21, No. 2, pp. 128-133.

International Search Report and Written Opinion, mailed Jun. 10, 2009 in related International Application No. PCT/US2009/036404 in 19 pp.

English Translation of Office Action dated Apr. 24, 2009 and issued in related Japanese Patent Application No. 2006-503503.

'(WO2007080868) Instrument for Inserting Intraocular Lens [English Translation powered by Google via WIPO Patentscope]', Jun. 3, 2011, hppt://patentscope.wipo.int/search/en/detail.jsf.

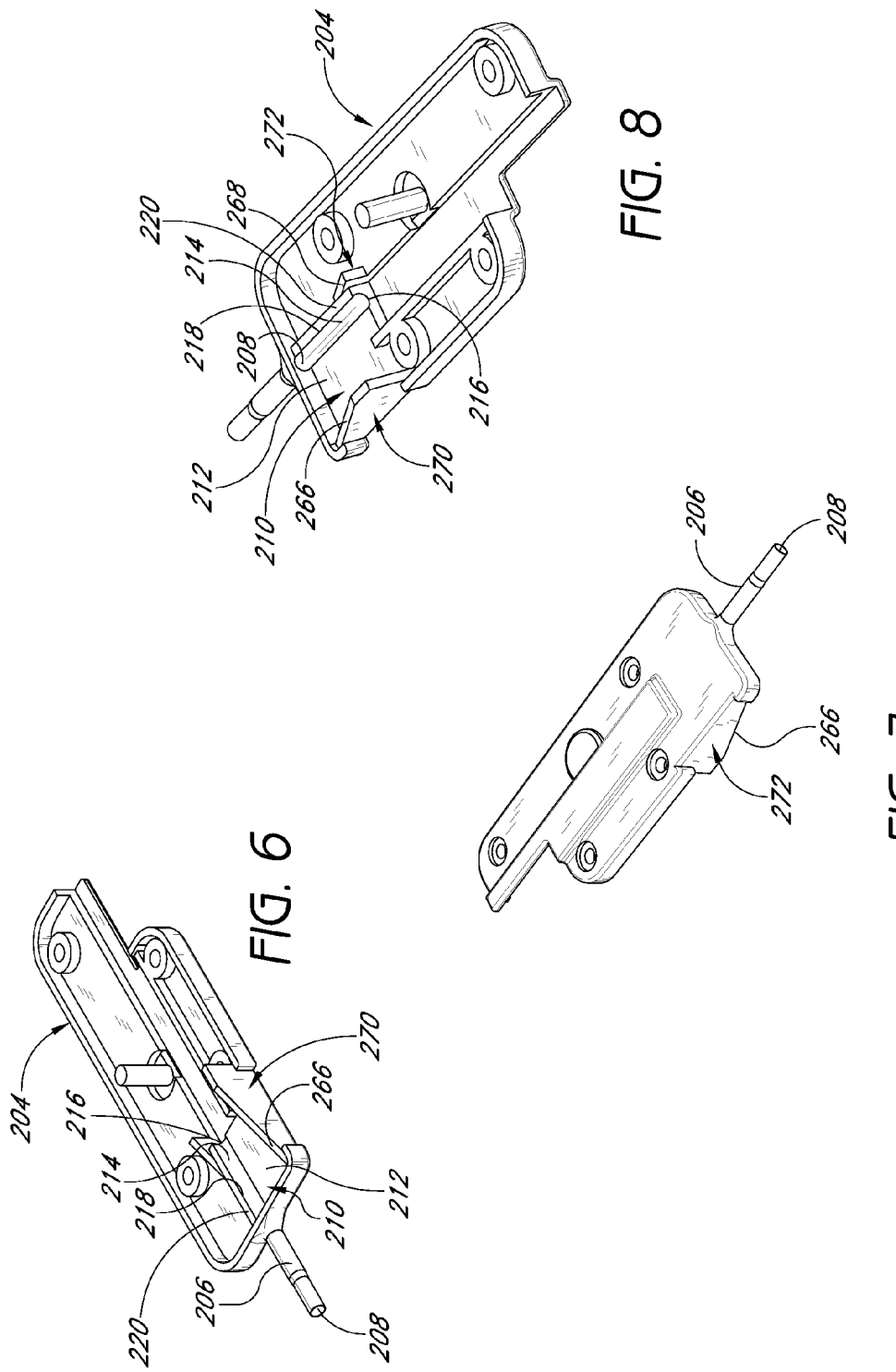

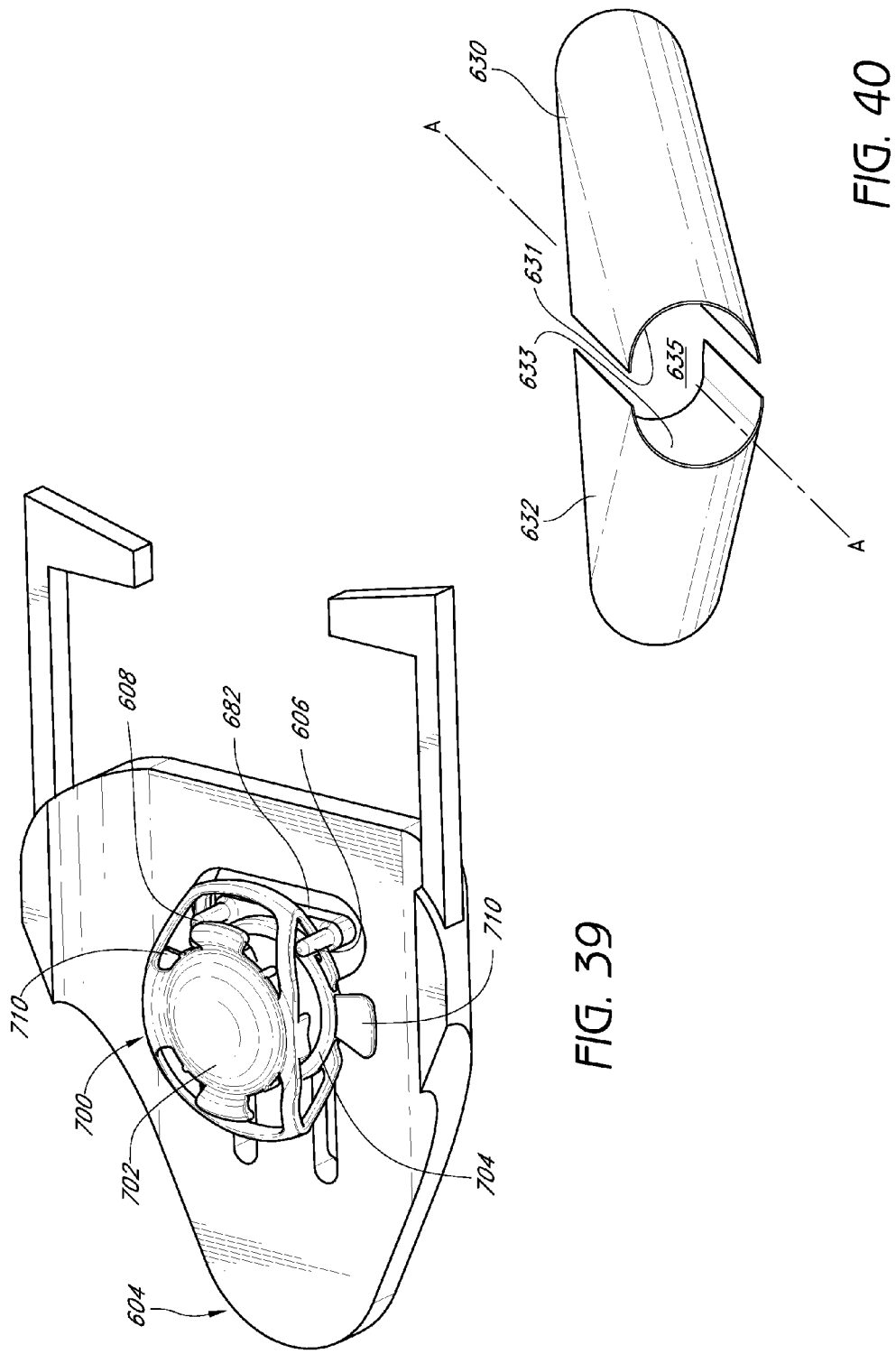

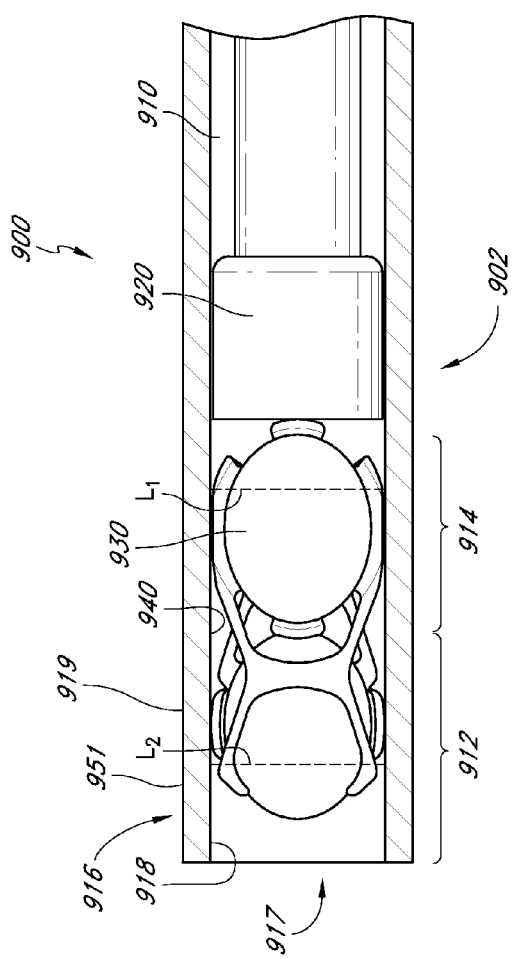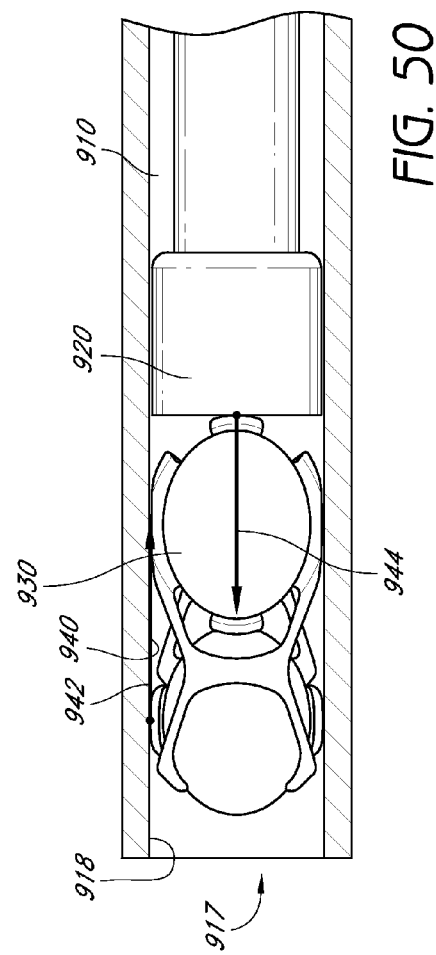

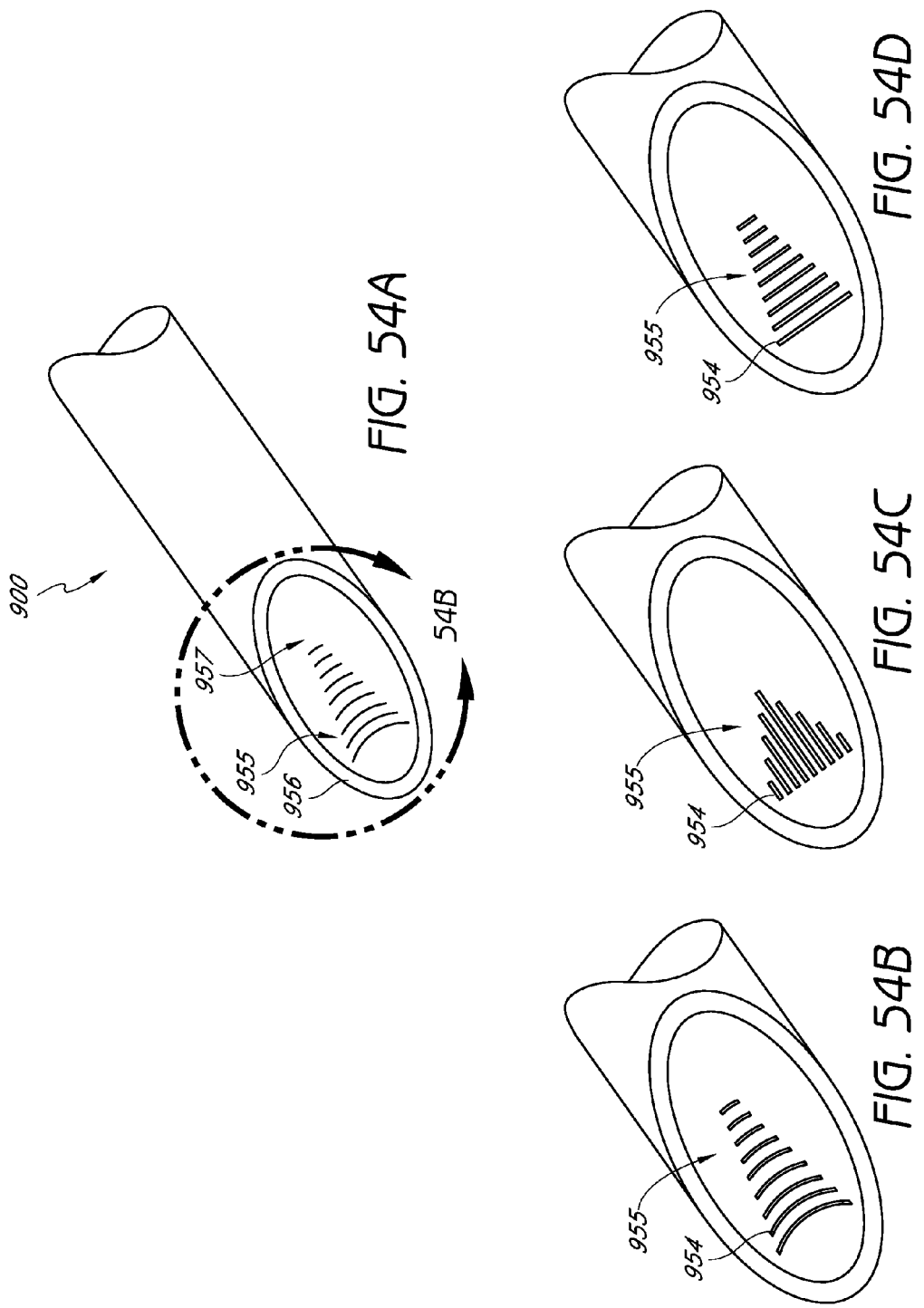

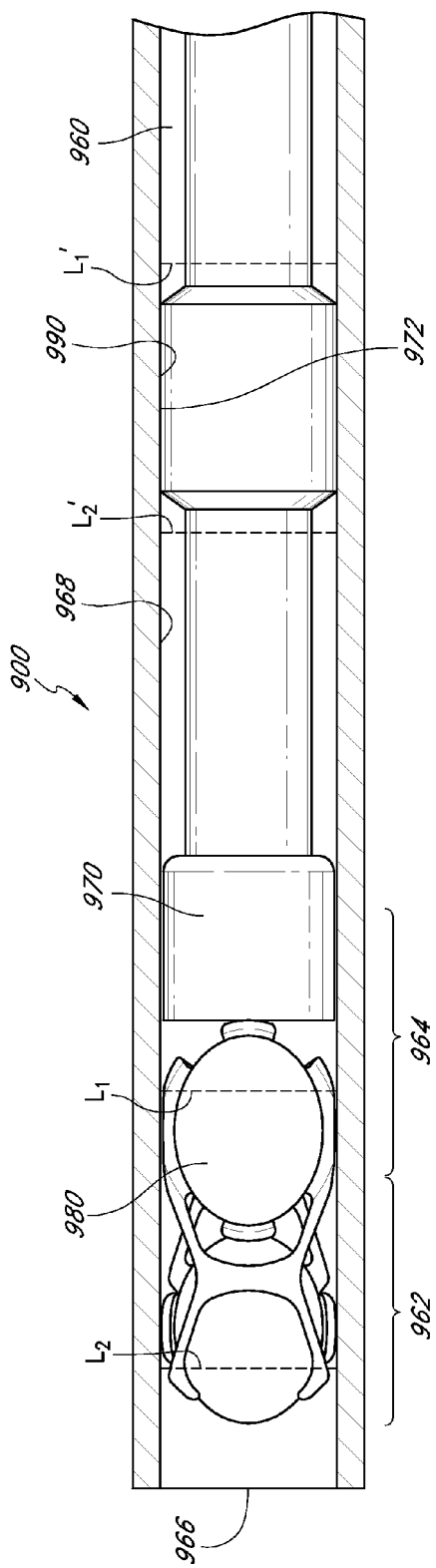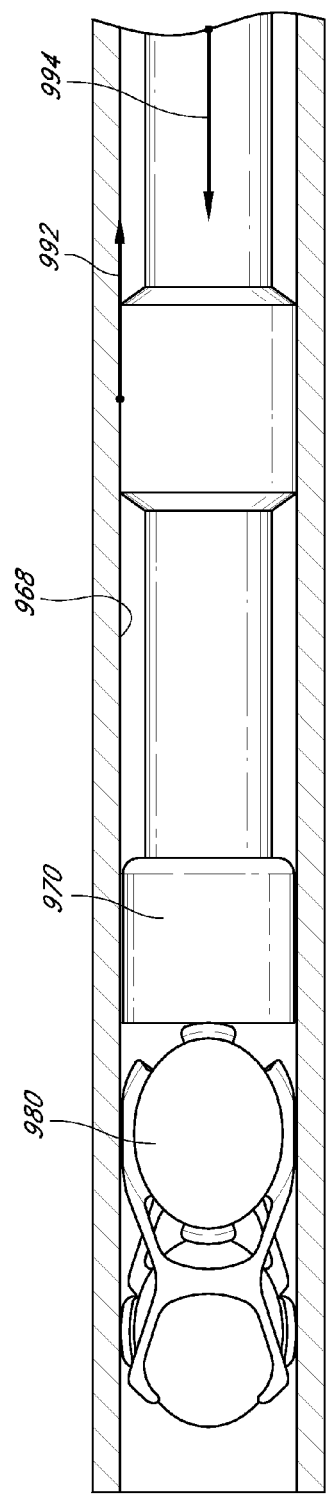

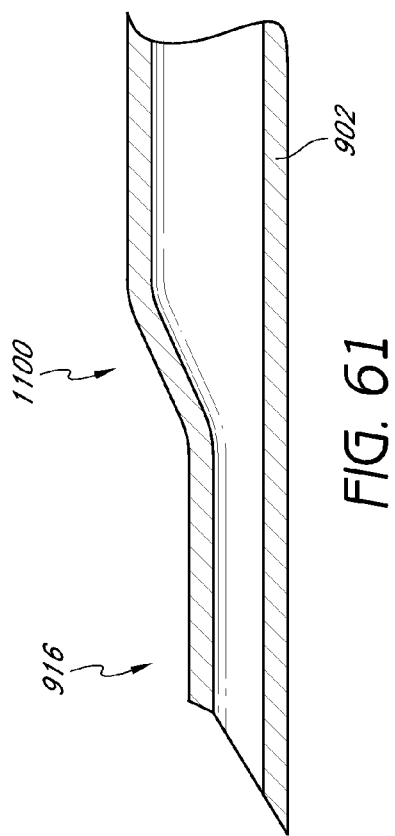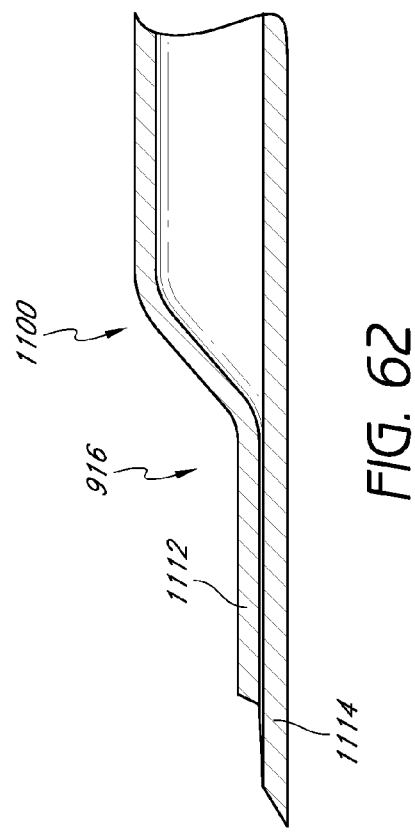

METHOD AND DEVICE FOR INSERTING AN INTRAOCULAR LENS

INCORPORATION BY REFERENCE TO ANY PRIORITY APPLICATIONS

Any and all applications for which a foreign or domestic priority claim is identified in the Application Data Sheet as filed with the present application, including U.S. application Ser. No. 12/047,259, are hereby incorporated by reference under 37 CFR 1.57.

BACKGROUND OF THE INVENTION

1. Field of the Invention

Various embodiments disclosed herein pertain to insertion of intraocular lenses into the eye of a patient, as well as methods and devices for preparing an intraocular lens for insertion, and for achieving the insertion itself.

2. Description of the Related Art

Artificial intraocular lenses are often implanted to replace or supplement the natural crystalline lens. Such a lens may be implanted where the natural lens has developed cataracts or has lost elasticity to create a condition of presbyopia. Implantation devices have been developed to roll or fold an intraocular lens, and/or assist in implanting a rolled or folded lens through a small incision in the patient's eye. However, these known implantation devices suffer from various drawbacks, many of which are addressed by certain embodiments disclosed herein.

SUMMARY OF THE INVENTION

In certain embodiments, an injector for inserting an intraocular lens into an eye comprises a lumen. The lumen can comprise a terminal portion at a distal end and a proximal portion juxtaposed with the terminal portion. The lumen can further comprise an inner surface. In some embodiments, the injector further comprises an injector plunger at least partially disposed within the lumen for generating a driving force on the intraocular lens. The driving force can cause the intraocular lens to move within the lumen. The lens can move through the proximal portion before the terminal portion. In some embodiments, the injector comprises a lens coefficient of friction between the inner surface and the intraocular lens when the lens is moving through the lumen. The lens coefficient of friction can be associated with a lens frictional force that resists the driving force. The lens coefficient of friction can have a first value when the lens is at a first location within the proximal portion and a second value when the lens is at a second location within the terminal portion. The first value can be smaller than the second value.

In some embodiments, as discussed further below, an increase from the first lens coefficient of friction to the second lens coefficient of friction can advantageously provide a tactile feedback to a user indicating that the lens is at or near the distal end of the lumen.

In some embodiments, an injector for inserting an intraocular lens into an eye comprises a lumen. The lumen can comprise a terminal portion at a distal end and a proximal portion juxtaposed with the terminal portion. The lumen can further comprise an inner surface. The injector can comprise an injector plunger at least partially disposed within the lumen for generating a driving force on the intraocular lens. The driving force can cause the intraocular lens to move within the lumen. The lens can move through the proximal portion before the terminal portion. In some embodiments, the injector comprises a lens coefficient of friction between the inner surface and the intraocular lens when the lens is moving through the lumen. The lens coefficient of friction can be associated with a lens frictional force that resists the driving force. The lens frictional force can have a first value when the lens is at a first location within the proximal portion and a second value when the lens is at a second location within the terminal portion. The first value can be smaller than the second value. In some embodiments, the lens frictional force increases abruptly from the first value to the second value as the lens approaches the distal end of the lumen. An increase in the lens frictional force from the first value to the second value can provide a tactile feedback to a user indicating that the lens is near the distal end of the lumen.

In some embodiments, an injector for inserting an intraocular lens into an eye comprises a lumen. The lumen can comprise a terminal portion at a distal end and a proximal portion juxtaposed with the terminal portion. The lumen can further comprise an inner surface. The injector can comprise an injector plunger at least partially disposed within the lumen. The plunger can be configured to generate a driving force on the intraocular lens that causes the intraocular lens to move within the lumen. The lumen can be configured such that the lens can move through the proximal portion before the terminal portion. In some embodiments, the inner surface is configured to cooperate with the intraocular lens to give rise to a lens coefficient of friction when the lens is moving through the lumen. The lens coefficient of friction can be associated with a lens frictional force that resists the driving force. The lens frictional force can have a first value when the lens is at a first location within the proximal portion and a second value when the lens is at a second location within the terminal portion. The first value can be smaller than the second value. In some embodiments, the lens frictional force increases abruptly from the first value to the second value as the lens approaches the distal end of the lumen. In some embodiments, an increase in the lens frictional force from the first value to the second value can provide a tactile feedback to a user indicating that the lens is near the distal end of the lumen.

In certain embodiments, an injector for inserting an intraocular lens into an eye comprises a lumen. The lumen can comprise a terminal portion at a distal end and a proximal portion juxtaposed with the terminal portion. The lumen can further comprise an inner surface. The injector can comprise an injector plunger at least partially disposed within the lumen for generating a driving force on the intraocular lens. The driving force can cause the intraocular lens to move within the lumen. The lens can move through the proximal portion before the terminal portion. The plunger can comprise an abutting surface in facing relationship to the inner surface. In some embodiments, the injector comprises a plunger coefficient of friction between the inner surface and the abutting surface when the plunger is moving through the lumen. The plunger coefficient of friction can be associated with a plunger frictional force that resists the driving force. The plunger frictional force can have a first value when the lens is at a first location within the proximal portion and a second value when the lens is at a second location within the terminal portion. The first value can be smaller than the second value. In some embodiments, an increase in the plunger frictional force from the first value to the second value can provide a tactile feedback to a user indicating that the lens is near the distal end of the lumen.

In certain embodiments, a method is provided for operating an injector having an intraocular lens disposed therein. The injector comprises a lumen having a terminal portion at a distal end thereof and a proximal portion juxtaposed with the terminal portion. The lumen comprises an inner surface. In some embodiments, the method comprises exerting a first lens frictional force on the intraocular lens when the lens is at a first location within the proximal portion. The first lens frictional force can be associated with a first lens coefficient of friction between the lens and the inner surface. The method can further comprise exerting a second lens frictional force on the intraocular lens when the lens is at a second location within the terminal portion. The second lens frictional force can be associated with a second lens coefficient of friction between the lens and the inner surface. The second lens coefficient of friction can be larger than the first lens coefficient of friction.

In certain embodiments, a method is provided for operating an injector having an intraocular lens disposed therein. The injector can comprise a lumen having a terminal portion at a distal end thereof and a proximal portion juxtaposed with the terminal portion. The lumen can comprise an inner surface. In certain embodiments, the method comprises advancing the intraocular lens toward the distal end of the lumen. The method can comprise exerting a first lens frictional force on the intraocular lens when the lens is at a first location within the proximal portion. The first lens frictional force can be associated with a first lens coefficient of friction between the lens and the inner surface. The method can comprise exerting a second lens frictional force on the intraocular lens when the lens is at a second location within the terminal portion. The second lens frictional force can be associated with a second lens coefficient of friction between the lens and the inner surface. The second lens frictional force can be larger than the first lens coefficient of friction. The method can comprise abruptly transitioning from the first lens frictional force to the second lens frictional force.

In some embodiments, a method is provided for operating an injector comprising a lumen and a plunger at least partially disposed within the lumen. The lumen can comprise a terminal portion at a distal end and a proximal portion juxtaposed with the terminal portion. The lumen can further comprise an inner surface. An intraocular lens can be disposed in the injector. In some embodiments, the method comprises exerting a first plunger frictional force on the plunger when the lens is at a first location within the proximal portion. The first plunger frictional force can be associated with a first plunger coefficient of friction between the abutting surface and the inner surface. The method can comprise exerting a second plunger frictional force on the plunger when the lens is at a second location within the terminal portion. The second plunger frictional force can be associated with a second plunger coefficient of friction between the abutting surface and the inner surface. The second plunger frictional force can be larger than the first plunger frictional force. An increase from the first plunger frictional force to the second plunger frictional force can advantageously provide a tactile feedback to a user indicating that the lens is near the distal end of the lumen.

In certain embodiments, an injector for inserting a dual-optic intraocular lens into the anterior chamber an eye comprises a tubular section having a lumen for conveying the dual-optic intraocular lens in a compacted condition along the tubular section with one optic in front of another optic. The injector can further comprise a release control section at a distal end portion of the tubular section. The release control section can be sized to fit within the anterior chamber when the injector is positioned in the eye for injection of the dual-optic intraocular lens into the anterior chamber. The release control section can resist passage of the intraocular lens through the portion of the injector within the anterior chamber such that release of mechanical energy stored in the compacted dual-optic intraocular lens is slowed.

In some embodiments, a method for injecting an intraocular lens comprising multiple optics into an eye comprises providing an injector having the intraocular lens positioned in an injection lumen with at least one optic in front of another optic. The method can further include inserting a release control section of the injector into the eye such that substantially the entire release control section is in the anterior chamber of the eye. The method can also include advancing the intraocular lens to the release control section. In some embodiments, the method includes using the release control section to significantly retard further advancement of the intraocular lens into the eye. The release control section can inhibit sudden release of mechanical energy stored in the compacted intraocular lens and slow entry of the intraocular lens from the injector into the anterior chamber. Other embodiments are also disclosed.

BRIEF DESCRIPTION OF THE DRAWINGS

Having thus summarized the general nature of the inventions, certain preferred embodiments and modifications thereof will become apparent to those skilled in the art from the detailed description herein having reference to the figures that follow, of which:

FIG. 6 is a perspective view of the lower housing of the apparatus of FIG. 3.

FIG. 7 is a second perspective view of the lower housing of the apparatus of FIG. 3.

FIG. 8 is a third perspective view of the lower housing of the apparatus of FIG. 3.

FIG. 39 is a detail perspective view of the actuator and lens system.

FIG. 40 is a detail perspective view of compacting members of the injector of FIG. 33.

FIG. 49 is a schematic partial top cross-sectional view of an embodiment of an injector.

FIG. 50 is a schematic partial top cross-sectional view of the injector of FIG. 49 showing the presence of a driving force and a frictional force.

FIG. 54A is a partial perspective view of an embodiment of an injector having an angled tip that includes a plurality of grooves arranged in a pattern.

FIG. 54B is an enlarged view of the angled tip shown in FIG. 54A showing the grooves in more detail.

FIG. 54C is a view similar to that shown in FIG. 54B illustrating grooves arranged in another pattern.

FIG. 54D is a view similar to that shown in FIG. 54B illustrating grooves arranged in another pattern.

FIG. 55 is a schematic partial top cross-sectional view of another embodiment of an injector.

FIG. 56 is a schematic partial top cross-sectional view of the injector of FIG. 55 showing the presence of a driving force and a frictional force.

FIG. 61 is a schematic partial side cross-sectional view of the injector of FIG. 60.

FIG. 62 is a schematic partial side cross-sectional view of another embodiment of an injector having a flattened end.

DETAILED DESCRIPTION OF THE PREFERRED EMBODIMENT

Figure 1:
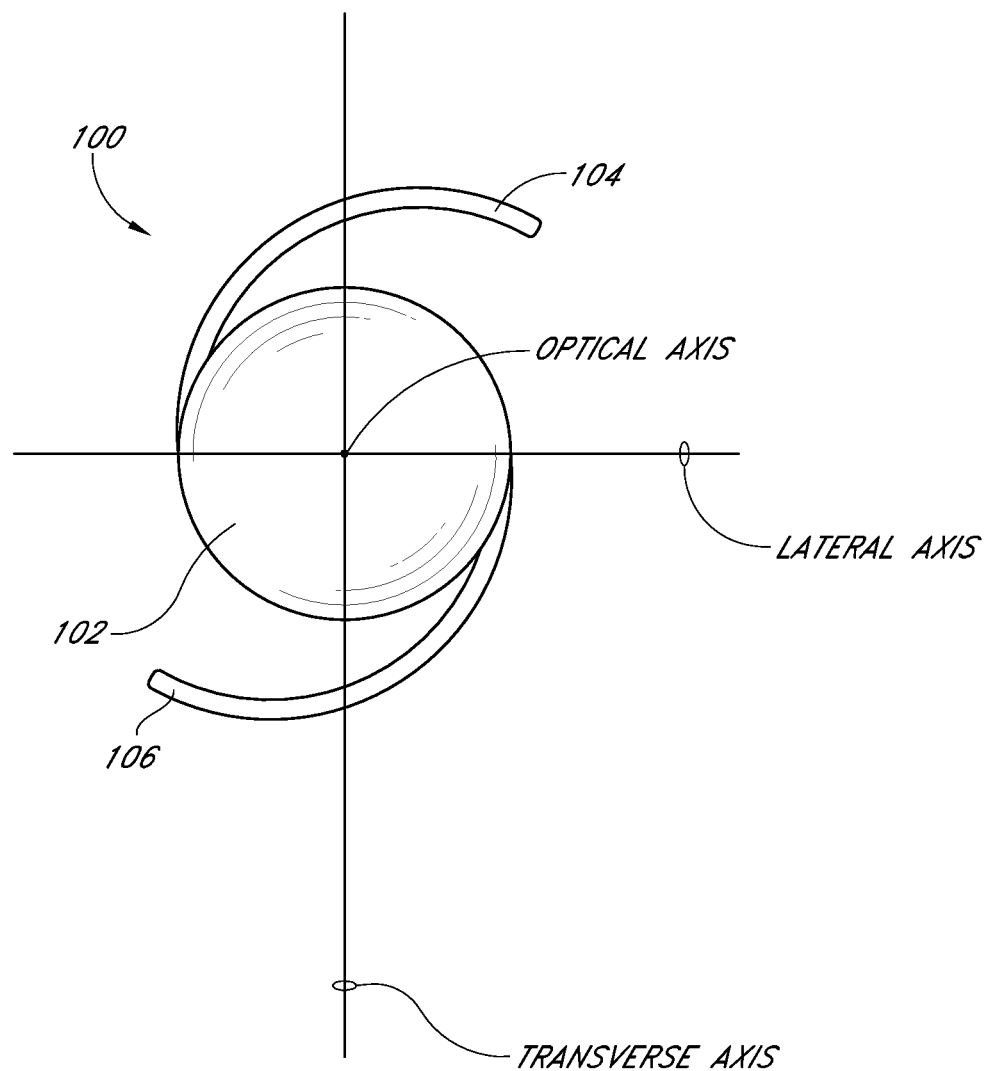
FIG. 1 is a front view of one type of single-lens IOL.
Figure 2:
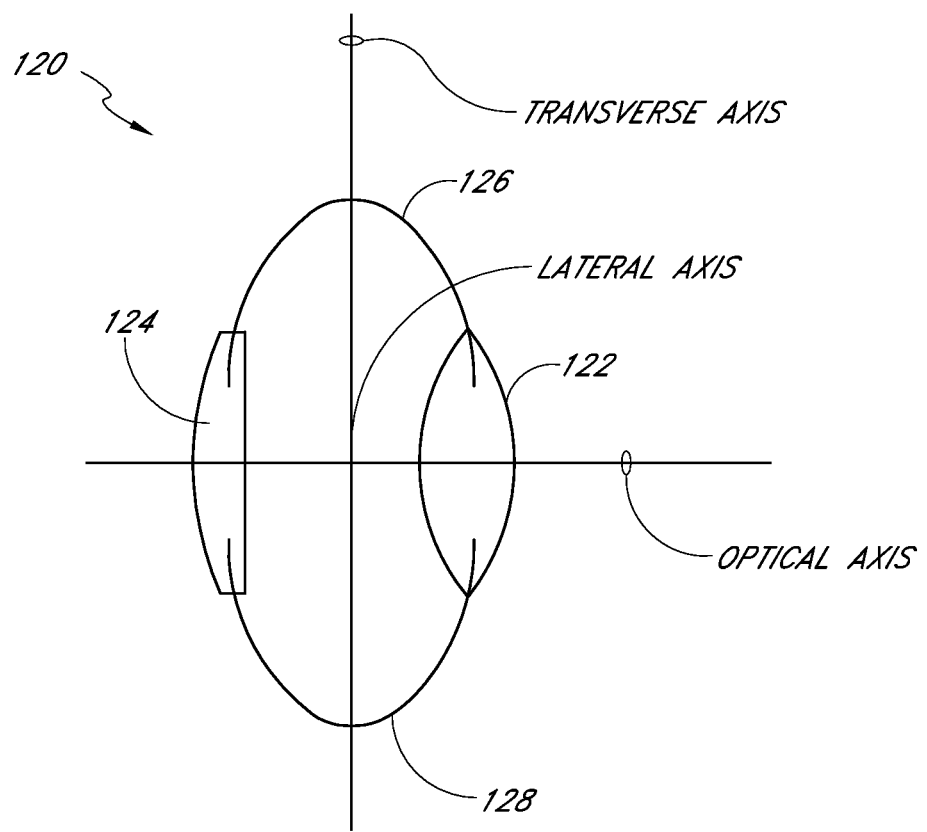
FIG. 2 is a side view of one type of multiple-lens IOL.

FIGS. 1 and 2 depict two known types of intraocular lenses ("IOLs") which are suitable for implantation in a human or animal eye to replace or supplement the natural crystalline lens. An IOL may be implanted, for example, when the natural lens has developed cataracts or has lost elasticity to create a condition of presbyopia.

FIG. 1 is front view of a conventional single-lens IOL 100 comprising an optic 102 to which are connected two or more haptics 104, 106. The optic 102 typically has a refractive power which is selected to replace or adjust the optical performance of the natural lens. The haptics 104, 106 comprise spring-like members which fix the optic in an appropriate location (e.g., inside the ciliary capsule or between the cornea and iris). The IOL 100 has an optical axis generally orthogonal to and centered on the optic; accordingly, in FIG. 1 the optical axis is depicted as a point. In addition, the IOL 100 has a transverse axis orthogonal to the optical axis and passing through arbitrarily chosen top and bottom points of the IOL 100, and a lateral axis orthogonal to the optical and transverse axes, and passing through arbitrarily chosen left and right points of the IOL 100. (The top, bottom, left and right positions are said to be "arbitrarily chosen" because the IOL 100 can be employed in a variety of orientations within the eye, so long as the optical axis is substantially coincident with the optical axis of the eye itself.)

FIG. 2 is a side view of a dual- or multiple-lens IOL 120 comprising first and second viewing elements 122, 124 which are interconnected by two or more biasing members 126, 128. One or both of the viewing elements 122, 124 may comprise an optic having refractive power. An IOL of this type is typically implanted in the ciliary capsule such that the biasing members maintain one of the viewing elements 122, 124 against the anterior region of the ciliary capsule, and the other of the viewing elements 122, 124 against the posterior region of the ciliary capsule. The biasing members 126, 128 may be constructed to have spring-like properties to permit the separation between the viewing elements 122, 124 to change in response to changes in the shape of the ciliary capsule that occur during accommodation.

Like the single-lens IOL 100, the multiple-lens IOL 120 has an optical axis, transverse axis and lateral axis, arranged depicted in FIG. 2. In the unstressed configuration shown in FIG. 2, the optical axes of the individual viewing elements 122, 124 are substantially coincident with the optical axis of the IOL 120 itself. However, as discussed below the optical axes of the individual viewing elements 122, 124 may be made non-coincident or non-coaxial during compaction of the IOL 120.

Various types of multiple-lens IOLs are disclosed in U.S. Pat. No. 7,118,596, issued on Oct. 10, 2006, titled ACCOMMODATING INTRAOCULAR LENS SYSTEM, and U.S. Pat. No. 6,884,261, issued on Apr. 26, 2005, titled METHOD OF PREPARING AN INTRAOCULAR LENS FOR IMPLANTATION. The entire contents of the above-mentioned publication and the entire contents of the above-mentioned patent are hereby incorporated by reference herein and made a part of this specification.

Intraocular lenses are typically implanted (after any removal of the natural lens) by first folding or rolling the IOL. The folded/rolled IOL is then inserted into the desired location in the eye by passing the IOL through one or more incisions made in the cornea, sclera and/or ciliary capsule. Once in place, the natural resilience of the IOL causes it to return, either partially or completely, to its original unrolled/unfolded state, whereupon the IOL can function as desired to improve the patient's vision.

FIGS. 3-20 depict one embodiment of an apparatus 200 for compacting and/or inserting an intraocular lens. The depicted apparatus 200 (as well as the other embodiments depicted and/or described herein) may, but need not, be employed to compact and/or insert an intraocular lens, including without limitation IOLs of the types depicted in FIG. 1 or FIG. 2, those described in the publication and patent mentioned above, or any suitable single- or multiple-lens IOL.

Figure 3:
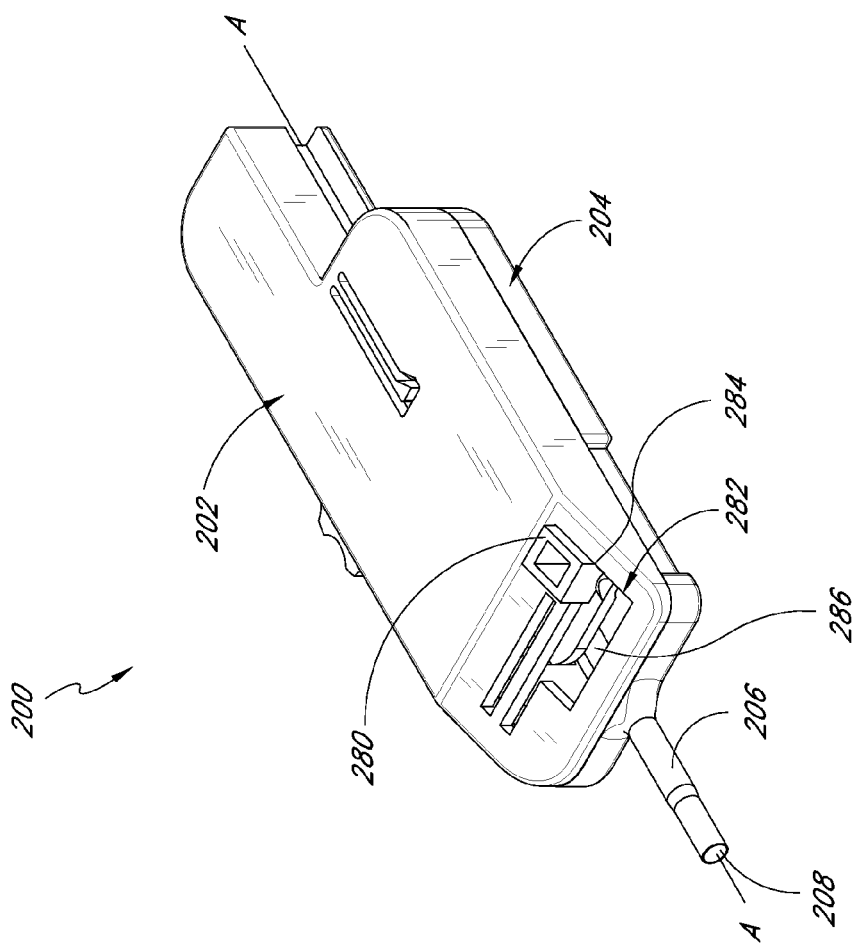
FIG. 3 is a perspective view of one embodiment of an apparatus for compacting and/or inserting an intraocular lens.
Figure 4:
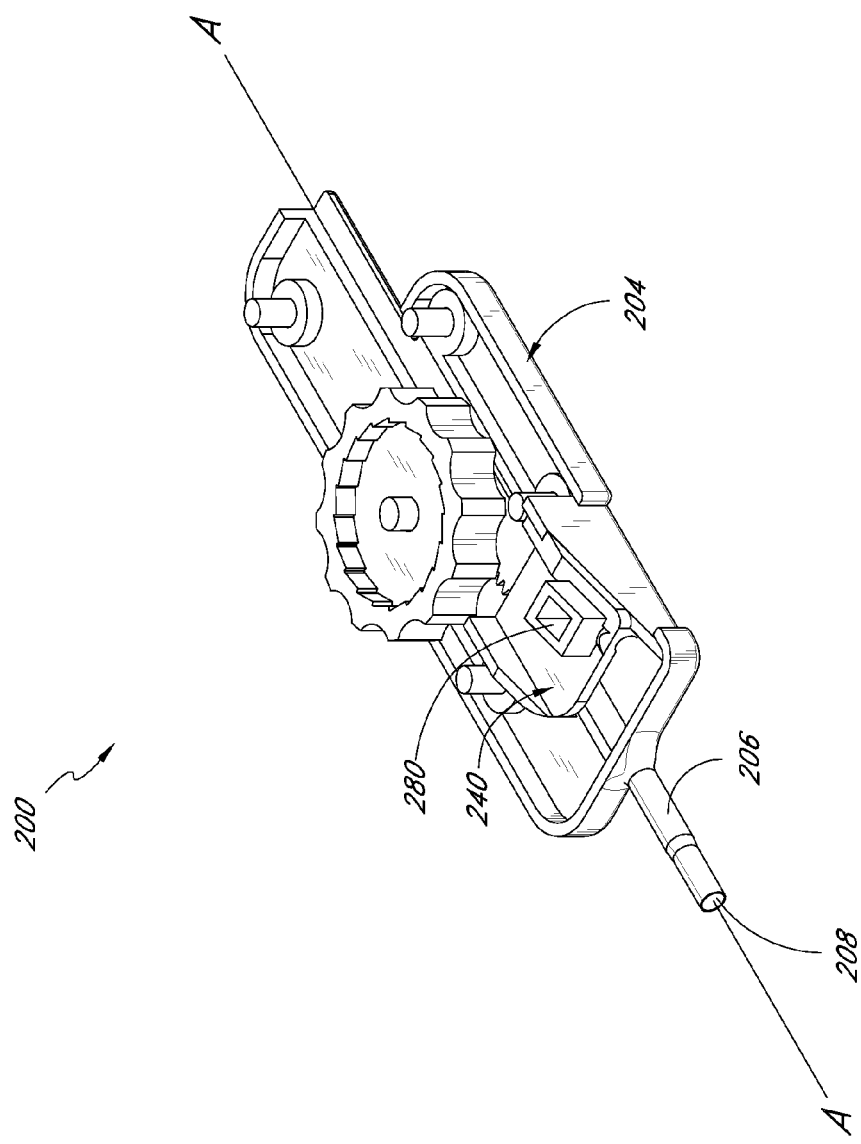
FIG. 4 is a perspective view of the apparatus of FIG. 3, with the upper housing portion removed for clarity.
Figure 5:
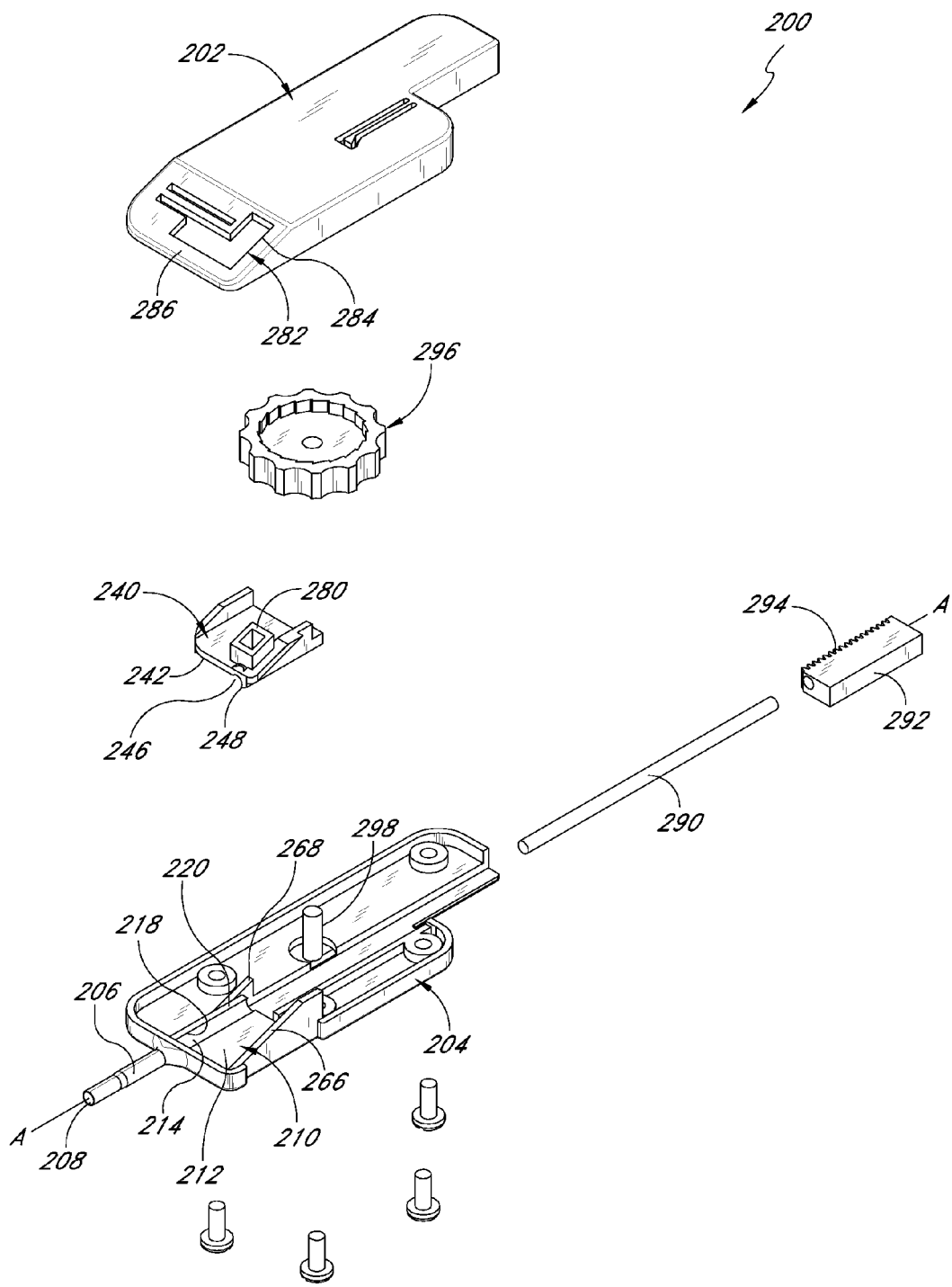
FIG. 5 is an exploded view of the apparatus of FIG. 3.

With reference now to FIGS. 3-5, the apparatus 200 preferably comprises an upper housing 202 and a lower housing 204 which cooperate to enclose and support the components of the apparatus 200. The lower housing 204 preferably forms a delivery probe 206 which in turn defines a delivery lumen 208; both the delivery probe 206 and lumen 208 extend along a longitudinally-oriented delivery or injection axis A-A of the apparatus 200. The lower housing 204 also preferably forms a lower lens compactor or lower compacting element 210 comprising a lower engagement face or wall 212 and a lower insertion channel 214 which extends along the delivery axis A-A.

As best seen in FIG. 8, the lower engagement face 212 preferably comprises a generally flat surface which defines a plane extending generally parallel to (or intercepting) the delivery axis A-A. The lower insertion channel 214 is preferably a partial cylinder in shape, with an inner surface 216 which extends from the lower engagement face 212 to a lower channel edge 218 which preferably extends generally parallel to the delivery axis A-A. The lower insertion channel 214 preferably comprises a partial rearward extension, along the delivery axis A-A, of the inner surface of the delivery lumen 208. From the lower channel edge 218 a lower support surface 220 extends in a direction opposite the lower engagement face 212, while forming a generally flat surface which defines a plane extending preferably generally parallel to the face 212.

Figure 9:
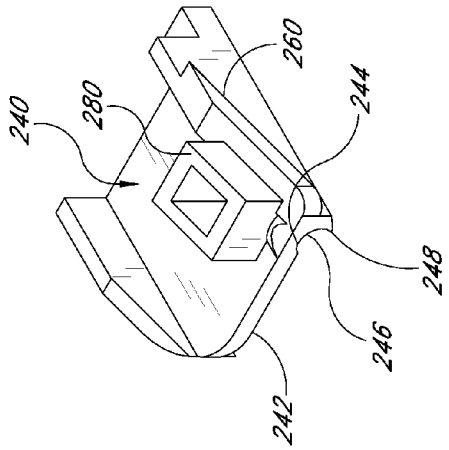
FIG. 9 is a perspective view of the upper lens compactor of the apparatus of FIG. 3.
Figure 10:
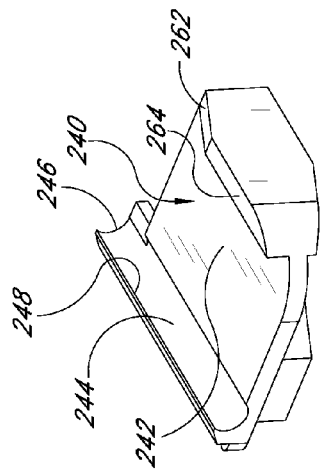
FIG. 10 is a second perspective view of the upper lens compactor of the apparatus of FIG. 3.
Figure 19:
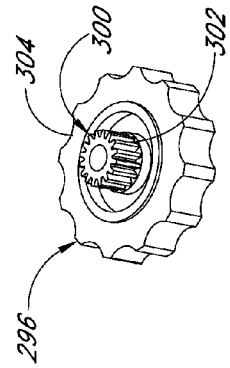
FIG. 19 is an upper perspective view of the pinion wheel of the apparatus of FIG. 3.
Figure 20:
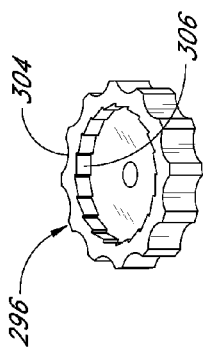
FIG. 20 is a lower perspective view of the pinion wheel of the apparatus of FIG. 3.
Figure 12:
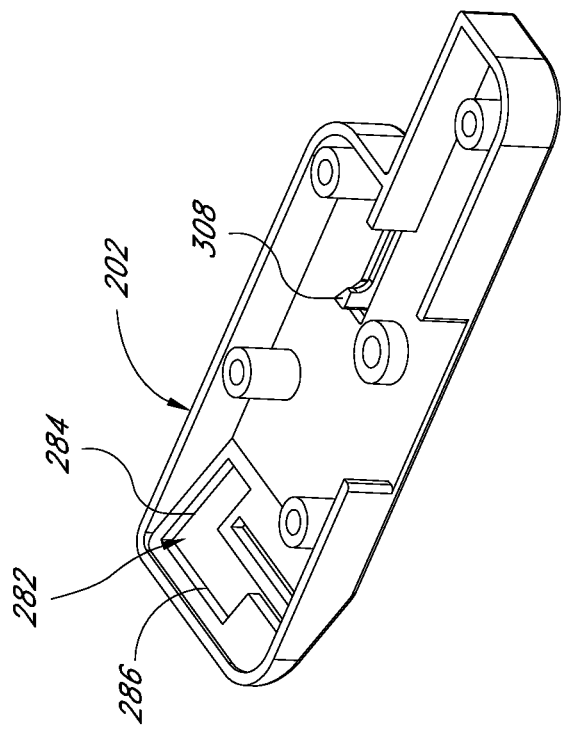
FIG. 12 is a second perspective view of the upper housing of the apparatus of FIG. 3.
Figure 11:
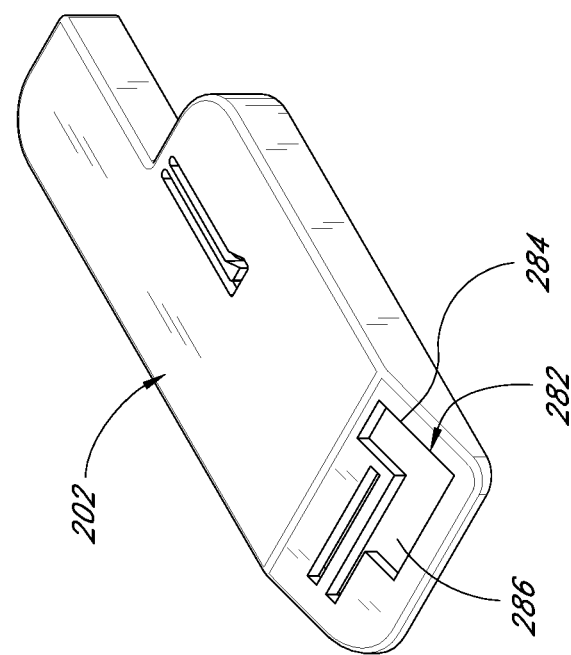
FIG. 11 is a perspective view of the upper housing of the apparatus of FIG. 3.
Figure 13:
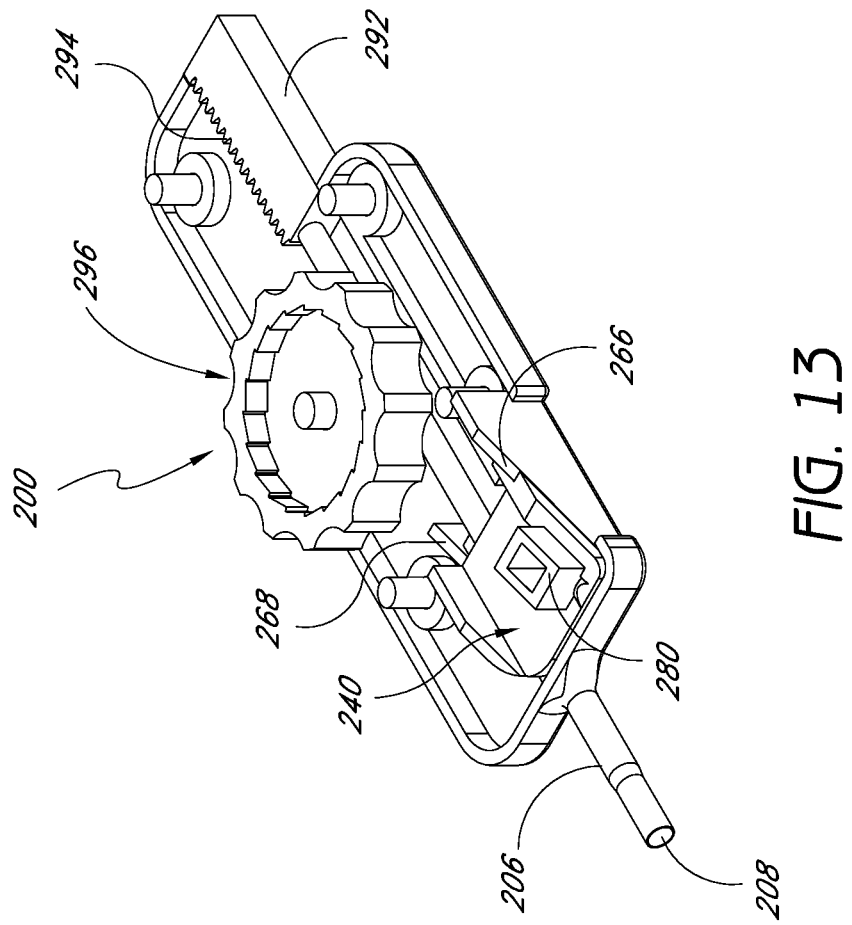
FIG. 13 is a perspective view of the apparatus of FIG. 3, with the upper housing portion removed for clarity, and the upper lens compactor moved to the first compacted position.

Referring again to FIGS. 3-5, and also to FIGS. 9-10, an upper lens compactor 240 is slidably disposed generally above the lower lens compactor 210. The lower and upper lens compactors 210, 240 together form a lens compactor of the apparatus 200. The depicted embodiment of the upper lens compactor 240 forms an upper engagement face 242 which preferably comprises a generally flat surface which, when the upper lens compactor is in position on the lower housing 204, defines a plane extending generally parallel to the delivery axis A-A. The upper lens compactor 240 preferably further comprises an upper insertion channel 244, which is preferably a partial cylinder in shape, with an inner surface 246 which extends from the upper engagement face 242 to an upper channel edge 248 which preferably extends generally parallel to the delivery axis A-A. (Alternatively, the insertion channels 214, 244 may taper inward as they extend forward, thereby forming a truncated cone or another inward-tapering surface upon their convergence when the upper lens compactor 240 is in the second compacted position (see below). Instead of or in addition to such a configuration of the insertion channels 214, 244, the inner surface of the delivery lumen 208 may also taper inward as it extends forward.)

In yet another embodiment, the delivery lumen 208 can have a generally oval cross-section (taken orthogonal to the delivery axis), with the channels 214, 244 shaped to have a similarly oval cross-section upon their convergence when the upper lens compactor 240 is in the second compacted position (see below).

The upper lens compactor 240 preferably further comprises first and second upper bearing surfaces 260, 262 disposed on respective opposite sides of the upper engagement face 242 and upper insertion channel 244, as well as a third upper bearing surface 264, which extends forward from the second upper bearing surface 262. The first, second and third upper bearing surfaces 260, 262, 264 preferably comprise generally flat surfaces which extend longitudinally, the first and second upper bearing surfaces 260, 262 being sloped with respect to the upper engagement face 242 and/or delivery axis A-A. The first and second upper bearing surfaces 260, 262 are (at least initially) slidably disposed against similarly-sloped first and second lower bearing surfaces 266, 268 formed on support ribs 270, 272 of the lower housing 204.

With reference now to FIGS. 3-5 and 9-12, the upper lens compactor 240 preferably also forms a compactor actuator 280 which, in the depicted embodiment, comprises a generally vertically-extending member suitable for manipulation by the thumb of a user. The compactor actuator 280 is received in a compactor guide 282 formed in the upper housing 202. In the depicted embodiment, the compactor guide 282 comprises a longitudinal slot 284 and a lateral slot 286 which are joined in an "L" configuration.

The upper and lower bearing surfaces 262, 264, 266, 268, and the compactor actuator 280 and compactor guide 282, coact to permit the upper lens compactor 240 to advance forward and downward from a home position (see FIGS. 3, 4, 15) in which the compactor actuator 280 is rearwardly disposed in the longitudinal slot 284, to a first compacted position (see FIGS. 13, 16) in which the compactor actuator 280 is forwardly disposed in the longitudinal slot 284, but has not yet been advanced laterally. This advancement of the upper lens compactor 240 moves the upper engagement face 242 forward and downward with respect to the lower engagement face 212, thereby reducing the vertical separation between the engagement faces 212, 242. The compactor actuator 280 and compactor guide 282 likewise coact to permit the upper lens compactor 240 to advance laterally from the first compacted position to a second compacted position (see FIGS. 14, 18) in which the compactor actuator 280 is laterally disposed in the lateral slot 286, remote from the longitudinal slot 284.

Figure 15:
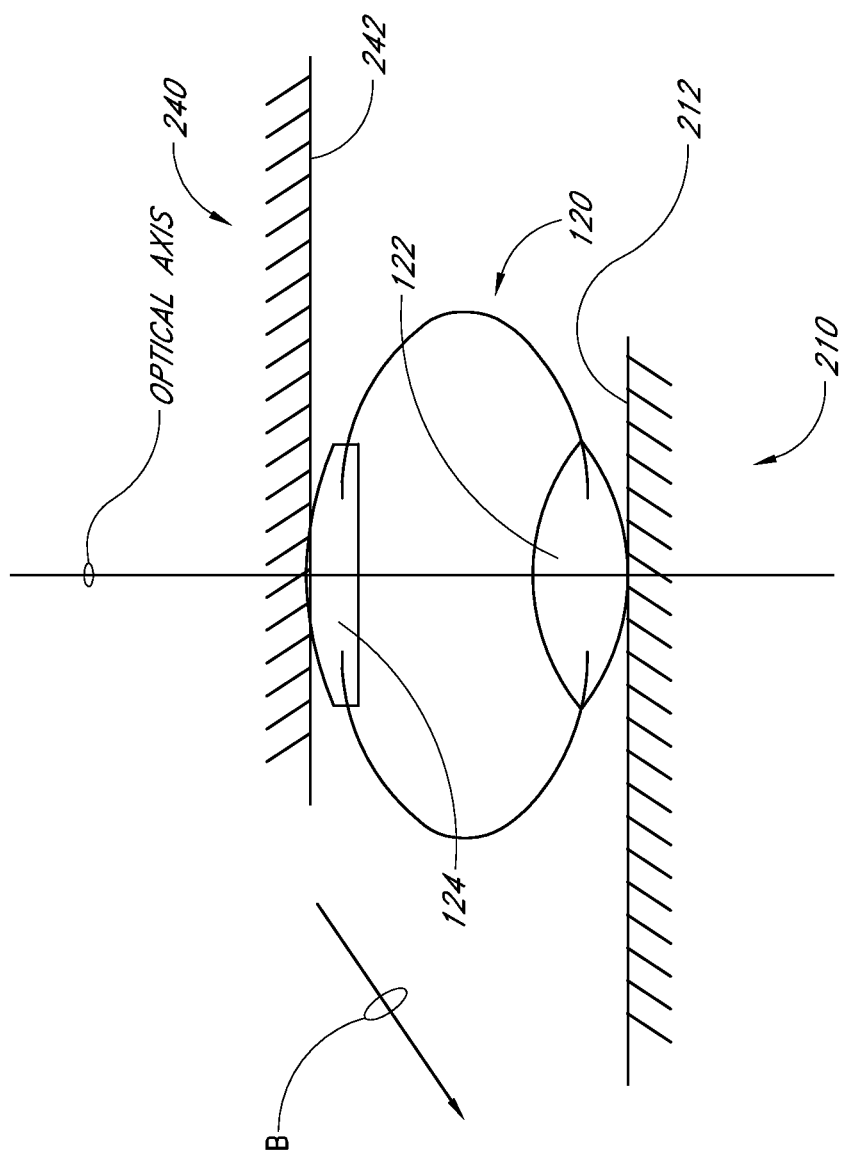
FIG. 15 is a schematic, side cross-sectional view of the apparatus of FIG. 3, with the upper lens compactor in the home position.

FIGS. 15-18 illustrate schematically the operation of the compactors 210, 240 in a circumstance in which a multiple-lens IOL, such as the IOL 120 described above, is stored or placed in the apparatus 200 for subsequent compaction and/or insertion. In FIG. 15, the upper lens compactor 240 is in the home position wherein the upper engagement face 242 is preferably generally parallel to the lower engagement face 212, and the multiple-lens IOL 120 is disposed between the faces 212, 242, preferably in a substantially unstressed condition in which the optical axes of the viewing elements are substantially coincident with each other, and/or with the optical axis of the IOL 120 itself.

Note that the IOL 120 is considered to be substantially unstressed even when the faces 212, 242 compress the viewing elements 122, 124 together somewhat, thereby slightly stressing the biasing members 126, 128. Accordingly, the separation between the faces 212, 242 may be chosen to slightly compress the viewing elements 122, 124 together when the upper lens compactor 240 is in the home position. The IOL 120 is also considered to be substantially unstressed when the faces 212, 242 draw the viewing elements 122, 124 apart somewhat, thereby slightly stressing the biasing members 126, 128. The separation between the faces 212, 242 may therefore be chosen to draw the viewing elements 122, 124 slightly apart when the upper lens compactor 240 is in the home position. The IOL 120 is also considered to be substantially unstressed when the outer faces or other portions of one or both of the viewing elements 122, 124 are deformed or stressed due to adhesion stresses between the faces 212, 242 and the viewing elements (which stresses can arise where the viewing elements 122, 124 comprise optics), as such stresses are relatively minor when viewed in the context of the entire IOL 120.

In the depicted embodiment, the engagement faces 212, 242 can comprise generally flat surfaces constructed from a material to which the outer faces of the viewing elements 122, 124 will tend to self-adhere. For example, acetal (sold as DELRIN™) may be employed to construct one or both of the faces 212, 242; this material displays good adhesion properties with many of the materials (e.g., silicone, polyurethanes, hydrogels, acrylics, PVA, styrene-based copolymers) typically employed to construct IOLs. Of course, any other material having good adhesion properties with the contacted portions of the IOL may be employed to form the engagement faces 212, 242. Materials having a lower coefficient of friction than that of acetal can also be used to construct the engagement faces 212, 242. For example, one or both of the engagement faces 212, 242 can be constructed from polycarbonate.

Figure 16:
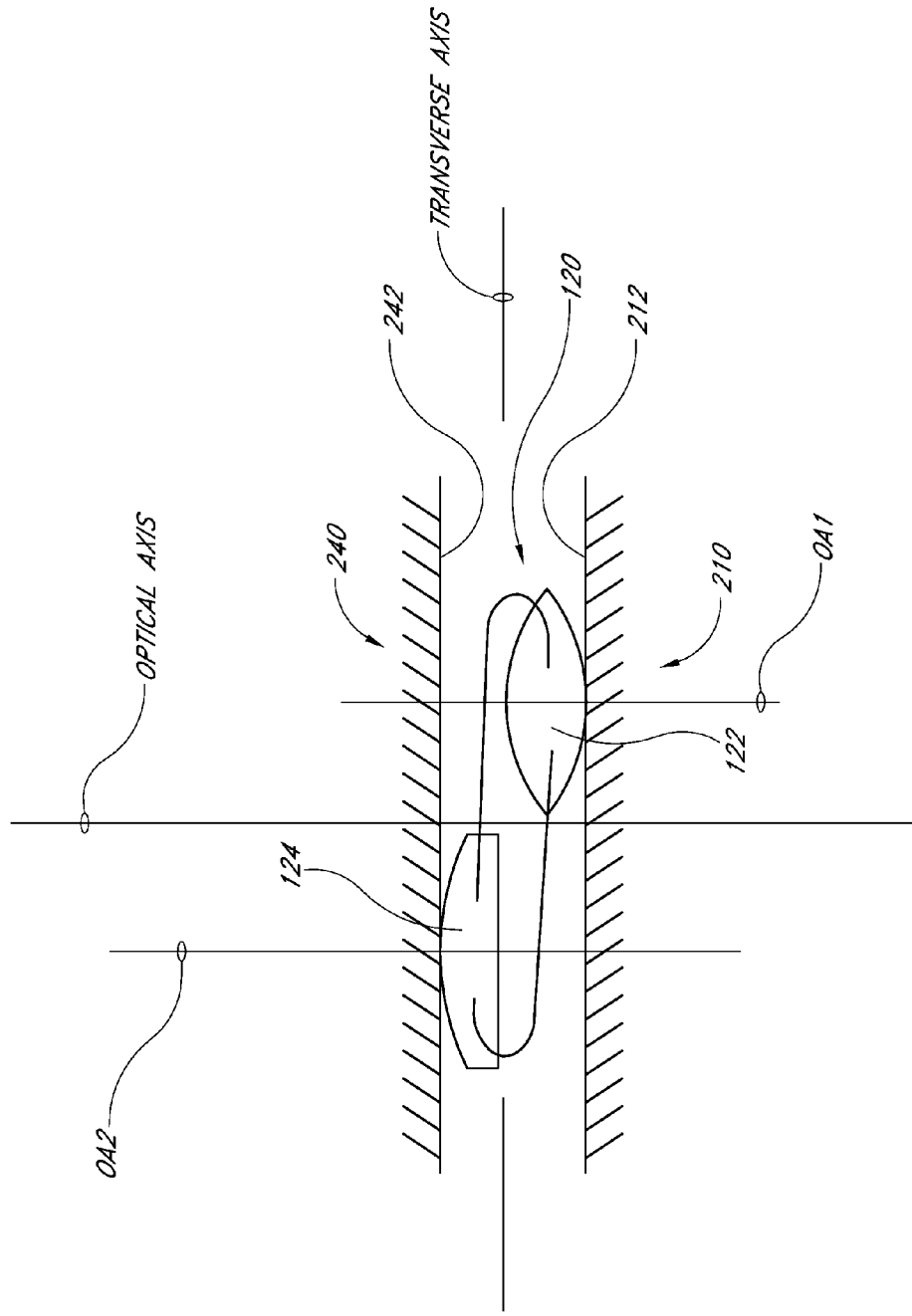
FIG. 16 is a schematic, side cross-sectional view of the apparatus of FIG. 3, with the upper lens compactor in the first compacted position.
Figure 17:
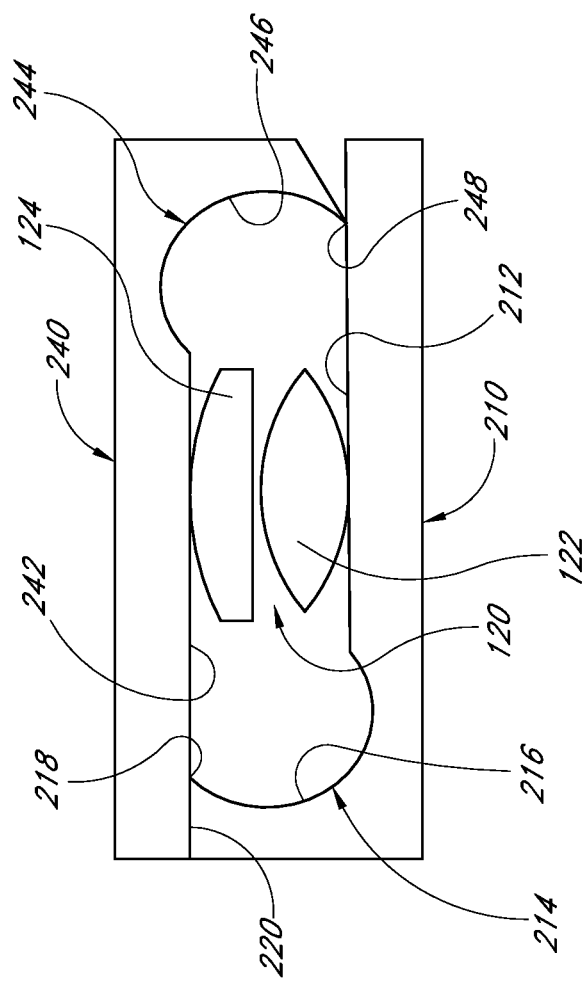
FIG. 17 is a schematic, front cross-sectional view of the apparatus of FIG. 3, with the upper lens compactor in the first compacted position.

From the home position depicted in FIG. 15, the upper engagement face 242 advances forward and downward, as indicated by the arrow B, to the first compacted position shown in FIGS. 16-17. With the upper engagement face in the first compacted position, the IOL 120 assumes a first compacted condition (also shown in FIGS. 16-17) in which the viewing elements 122, 124 are relatively displaced so that they are non-coaxial. (In other words, the optical axes OA1, OA2 of the individual viewing elements are non-coincident with each other, and/or with the optical axis of the IOL 120 itself.) In the depicted embodiment, the viewing elements 122, 124 are sufficiently relatively displaced when in the first compacted condition that no portion of the first viewing element 122 overlaps any portion of the second viewing element 124. However, in other embodiments the viewing elements 122, 124 may overlap somewhat (while being nonetheless non-coaxial), as the IOL 120 is viewed along the optical axis, while the IOL 120 is in the first compacted condition. Likewise, in the depicted embodiment no portion of the first viewing element 122 overlaps any portion of the second viewing element 124, as the IOL 120 is viewed along the transverse axis, when the IOL 120 is in the first compacted condition. However, in other embodiments the viewing elements 122, 124 may be sufficiently relatively displaced that they overlap somewhat, as the IOL 120 is viewed along the transverse axis, while the IOL 120 is in the first compacted condition. In still another embodiment, the IOL 120 may have an overall height, as measured along the optical axis, no greater than that of the higher of the first and second viewing elements 122, 124, when the IOL is in the first compacted condition. In the embodiment depicted in FIGS. 16-17, the height of the IOL 120, as measured along the optical axis, is substantially equal to the sum of the heights of the first and second viewing elements 122, 124.

As best seen in FIG. 17, when the upper lens compactor 240 is in the first compacted position, the upper channel edge 248 preferably contacts the lower engagement face 212 and the lower channel edge 218 preferably contacts the upper engagement face 242. In certain embodiments, the lower support surface 220 may also contact the upper engagement face 242. If desired, the IOL 120 may be lubricated when in the first compacted condition, using any suitable lubricant. The lubricant may assist in further compaction of the IOL 120.

Figure 14:
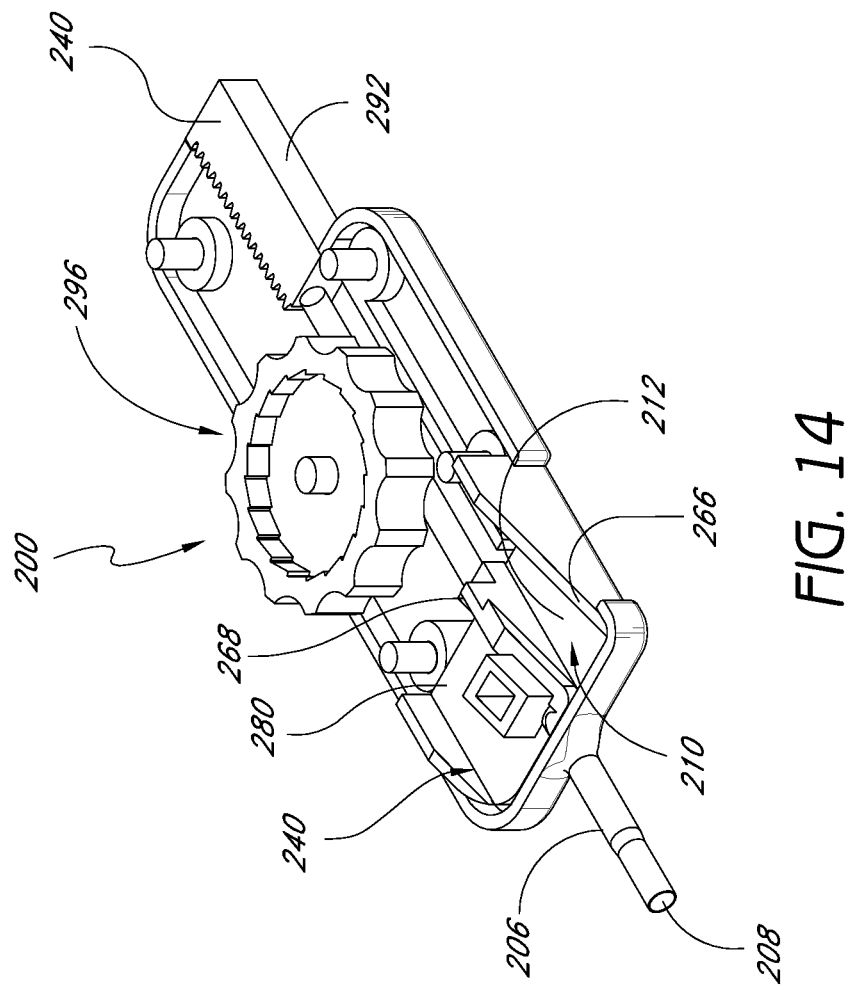
FIG. 14 is a perspective view of the apparatus of FIG. 3, with the upper housing portion removed for clarity, and the upper lens compactor moved to the second compacted position.
Figure 18:
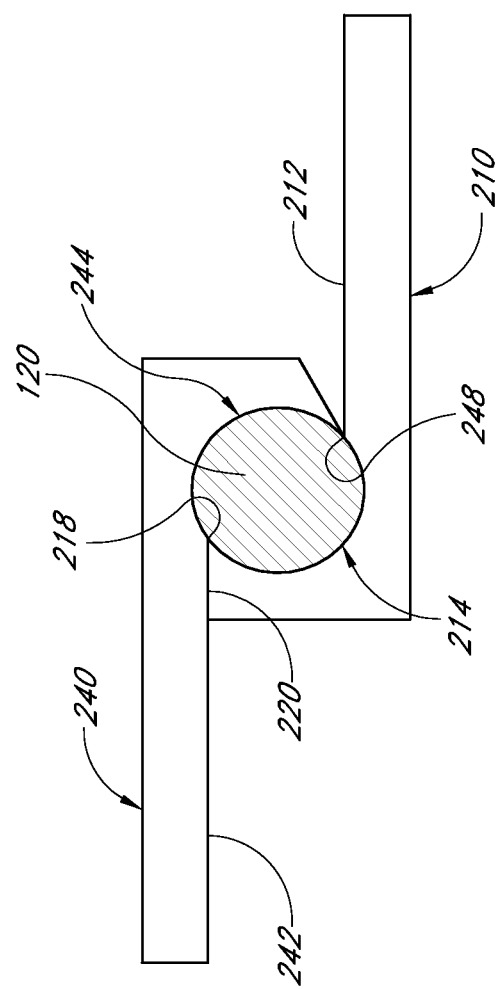
FIG. 18 a schematic, front cross-sectional view of the apparatus of FIG. 3, with the upper lens compactor in the second compacted position.

From the first compacted position, the upper lens compactor 240 may be advanced laterally to the second compacted position (see FIGS. 14, 18). As the upper lens compactor 240 is so advanced, the upper engagement face 242, inner surface 246 and/or upper insertion channel 244 urge the IOL 120 generally laterally toward the inner surface 216 and lower insertion channel 214. As best seen in FIG. 18, when the upper lens compactor 240 is in the second compacted position the upper insertion channel 244 is preferably disposed adjacent the lower insertion channel 214 such that they form a substantially complete cylinder which is substantially centered on the delivery axis A-A and forms a rearward extension of the delivery lumen 208. Accordingly, the inner surfaces 216, 246 and insertion channels 214, 244 "crush" the IOL 120 into a second compacted condition shown in FIG. 18.

With further reference to FIGS. 3-5 and 9-10, the apparatus 200 preferably further comprises a generally cylindrical driving member 290 which is disposed along the delivery axis A-A. (Where the delivery lumen 208 has an oval cross-section, the driving member 290 may have a similarly oval cross-section.) The rearward end of the driving member 290 is connected to a rack 292 which forms rack teeth 294 on one side thereof. A pinion wheel 296 is rotatably mounted on a pinion wheel bearing 298 which projects upward from the lower housing 204. The pinion wheel 296, shown in further detail in FIGS. 19-20, forms on its underside a pinion gear 300 comprising pinion teeth 302 which are configured to mesh with the rack teeth 294, upon manual advancement of the rack 292 and driving member 290 forward from a storage position (shown in FIGS. 4, 13-14) to a ready position (not shown) in which the forwardmost rack teeth 294 engage the pinion teeth 302. Once the rack 294 and driving member 290 reach the ready position, the user may manipulate the pinion wheel 296 via knurling 304 formed on the outer surface thereof, to advance the rack 294 and driving member longitudinally forward in the apparatus 200. As this is done, ratchet cogs 306 formed on an inner surface of the pinion wheel 296 cooperate with a ratchet pawl 308 formed on the upper housing 202 to prevent counter-rotation of the pinion wheel 296 or rearward motion of the rack 294 and driving member 290.

Where the IOL 120 has been compacted into the second compacted configuration (or is otherwise disposed in the lower insertion channel 214 or between the insertion channels 214, 244 when the upper lens compactor 240 is in the second compacted position), this forward movement of the driving member 290 causes the forward end of the driving member to advance through the lower insertion channel (or between the insertion channels 214, 244 when the upper lens compactor 240 is in the second compacted position), thereby urging the IOL 120 forward and into the delivery lumen 208 of the delivery probe 206. Further advancement of the driving member will then extrude the IOL from the forward end of the delivery probe 206.

Except where otherwise noted, the components of the apparatus 200 may be formed from any suitably rigid material, including plastics such as ABS or polycarbonate. The lower housing 204 (or, alternatively, at least the lower lens compactor 210 and/or delivery probe 206) may be formed from a transparent plastic such as clear polycarbonate, to promote visibility of the IOL during compaction/delivery.

Accordingly, the apparatus 200 may be employed to deliver or insert an IOL, such as the IOL 120, into an eye, such as a human eye. In doing so, the user/physician first accesses an insertion location (e.g., the capsular bag, anterior chamber, etc) within the eye via any suitable technique, for example, by making a small incision or series of small incisions in the anterior structures of the eye. If necessary, the natural crystalline lens is removed via a suitable technique such as phacoemulsification. Through the incision(s) the physician inserts the forward end of the delivery probe 206, preferably after compacting the IOL as detailed above and, if desired, after advancing the IOL partway through the lumen 208 of the delivery probe 206. With the end of the delivery probe in place, the physician extrudes the IOL from the probe 206, thereby inserting the IOL in the eye. (By employing the apparatus 200, the compacting and delivery may be done without opening the housing 202/204 or otherwise manually accessing the IOL.) Upon departure from the probe 206, the IOL "un-compacts" by virtue of its elasticity, returning substantially to its unstressed condition. The physician then withdraws the probe 206 and, if necessary, adjusts the positioning of the IOL within the eye. Upon satisfactory positioning of the IOL, the physician closes the incision(s) to complete the operation.

FIGS. 21-29 depict another embodiment of an apparatus 400 for compacting and/or inserting an intraocular lens. In one embodiment, the apparatus 400 is generally similar to the apparatus 200 described above and depicted in FIGS. 3-20, except as further detailed below. Except where otherwise noted, the components of the apparatus 400 may be formed from any suitably rigid material, including plastics such as ABS or polycarbonate.

The apparatus 400 preferably comprises an upper housing 402 and a lower housing 404 which cooperate to enclose and support the components of the apparatus 400. Disposed within the lower housing 404 is an injector plate 405 which forms a delivery probe 406 which in turn defines a delivery lumen 408; both the delivery probe 406 and lumen 408 extend along a longitudinally-oriented delivery or injection axis A-A of the apparatus 400. The injector plate 405 also forms a lower lens compactor or lower compacting element 410 comprising a lower engagement face or wall 412 and a lower insertion channel 414 which extends along the delivery axis A-A.

Figure 24:
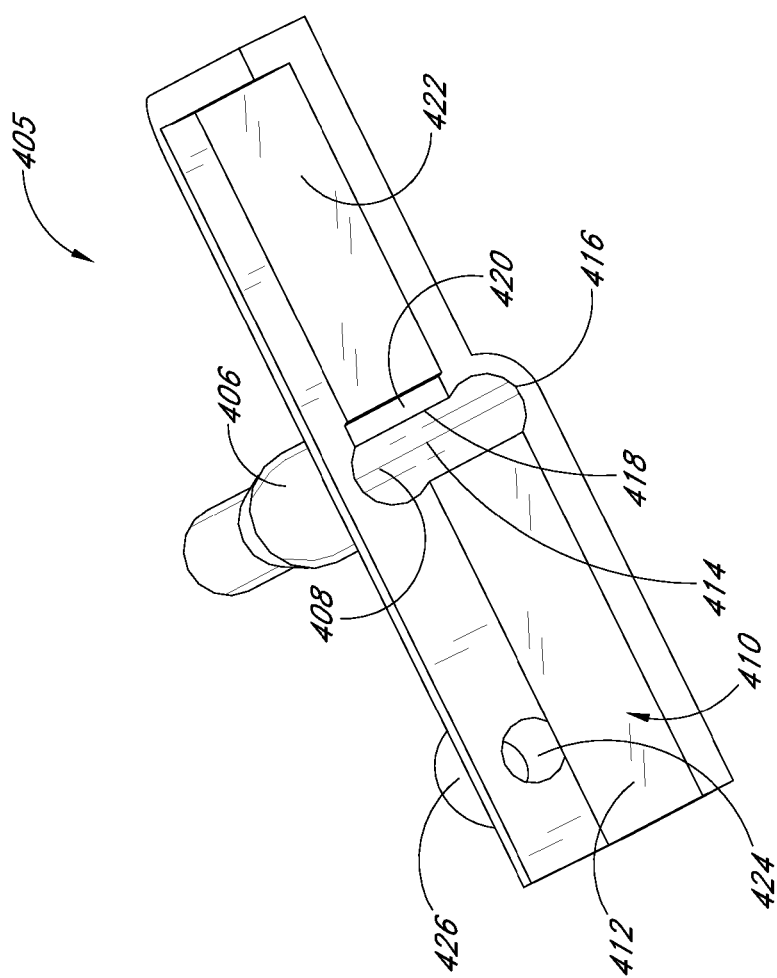
FIG. 24 is a perspective view of the injector plate of the apparatus of FIG. 21.

Best seen in FIG. 24, the lower engagement face 412 preferably comprises a generally flat surface which defines a plane extending generally parallel to (or intercepting) the delivery axis A-A. The lower insertion channel 414 is preferably a partial cylinder in shape, with an inner surface 416 which extends from the lower engagement face 412 to a lower channel edge 418 which preferably extends generally parallel to the delivery axis A-A. The lower insertion channel 414 preferably comprises a partial rearward extension, along the delivery axis A-A, of the inner surface of the delivery lumen 408. From the lower channel edge 418 a lower support surface 420 extends in a direction opposite the lower engagement face 412, while forming a generally flat surface which defines a plane extending generally parallel to the face 412. In the depicted embodiment, the lower support surface is slightly elevated with respect to a lower lateral surface 422 extending from the lower support surface 420 opposite the lower insertion channel 414. If desired, a lubricant opening 424 and lubricant fitting 426 may be provided in fluid communication with the lower lens compactor 410 to facilitate lubrication of the IOL during compaction.

The opening 424 also facilitates visibility of the IOL within the apparatus 400 at various stages of the compaction/delivery process. To further promote visibility of the IOL during compaction/delivery, a window or opening 407 may be formed in the lower housing 404 (see FIGS. 21-22, 28), and the lower engagement face 412 (or the entire injector plate 405) may be formed from a transparent material. Where the entire injector plate 405 is constructed from a transparent material, the post-compaction condition of the IOL will be visible in the delivery probe 406.

Figure 25:
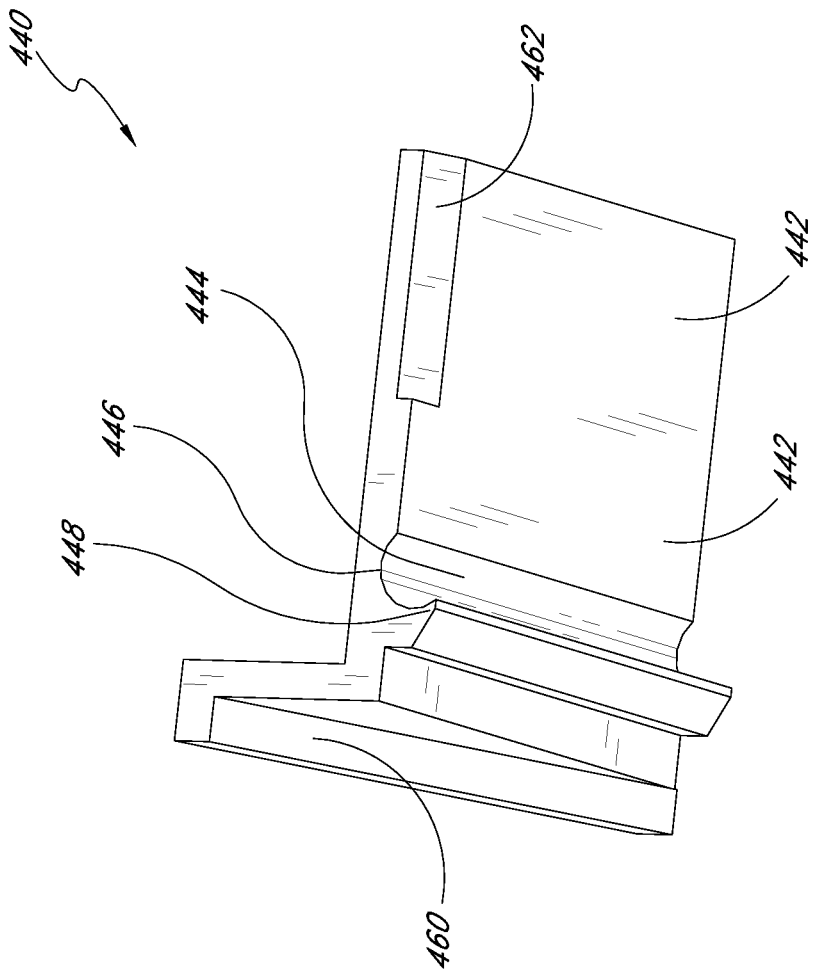
FIG. 25 is a perspective view of the upper lens compactor of the apparatus of FIG. 21.
Figure 26:
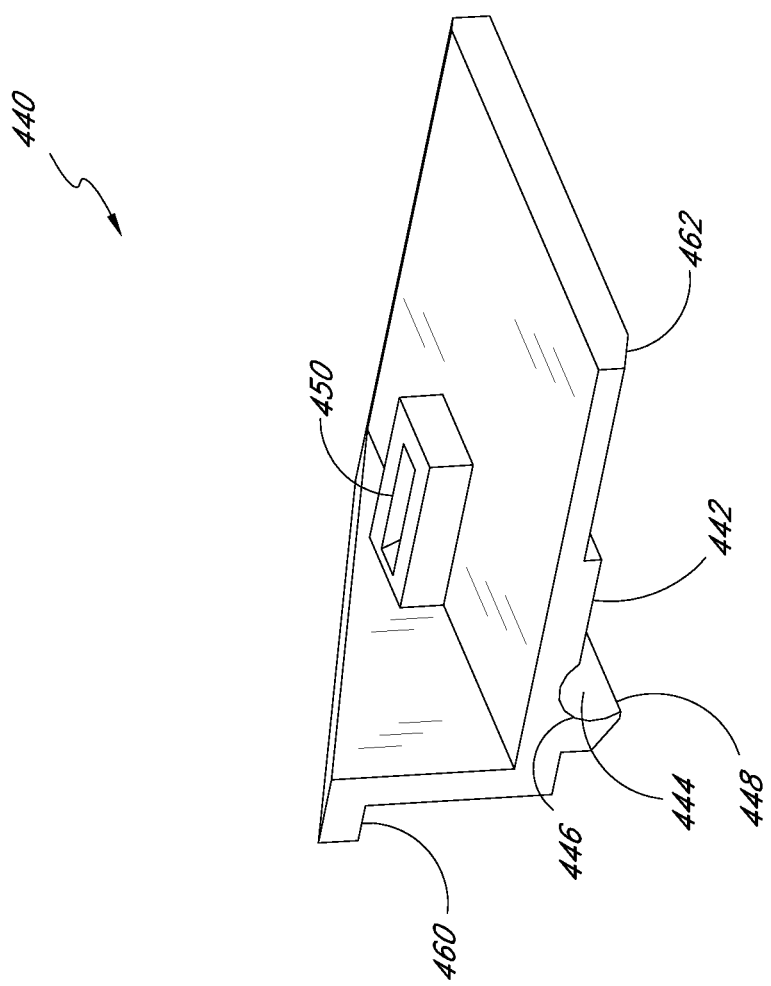
FIG. 26 is a second perspective view of the upper lens compactor of the apparatus of FIG. 21.

Referring again to FIGS. 21-22 and also to FIGS. 25-26, an upper lens compactor 440 is slidably disposed generally above the lower lens compactor 410. The lower and upper lens compactors 410, 440 together form a lens compactor of the apparatus 400. The upper lens compactor 440 forms an upper engagement face 442 which preferably comprises a generally flat surface which, when the upper lens compactor is in position on the lower housing 404, defines a plane extending generally parallel to the delivery axis A-A. The upper lens compactor 440 preferably further comprises an upper insertion channel 444, which is preferably a partial cylinder in shape, with an inner surface 446 which extends from the upper engagement face 442 to an upper channel edge 448 which preferably extends generally parallel to the delivery axis A-A. (Alternatively, the insertion channels 414, 444 may taper inward as they extend forward, thereby forming a truncated cone or another inward-tapering surface upon their convergence when the upper lens compactor 440 is in the second compacted position (see below). Instead of or in addition to such a configuration of the insertion channels 414, 444, the inner surface of the delivery lumen 408 may also taper inward as it extends forward.)

In yet another embodiment, the delivery lumen 408 can have a generally oval cross-section (taken orthogonal to the delivery axis), with the channels 414, 444 shaped to have a similarly oval cross-section upon their convergence when the upper lens compactor 440 is in the second compacted position (see below).

The upper lens compactor 440 preferably further comprises first and second upper bearing surfaces 460, 462 disposed on respective opposite sides of the upper engagement face 442 and upper insertion channel 444. The first and second upper bearing surfaces 460, 462 preferably comprise generally flat surfaces which extend longitudinally and are sloped with respect to the upper engagement face 442 and/or delivery axis A-A. The first and second upper bearing surfaces 460, 462 are (at least initially) slidably disposed against similarly-sloped first and second lower bearing surfaces 466, 468 formed on support ribs 470, 472 of the lower housing 404 (see FIG. 29). The upper lens compactor 440 further comprises an interface slot 450 which mates with an interface tab 452 formed on a compactor actuator 480.

Figure 27:
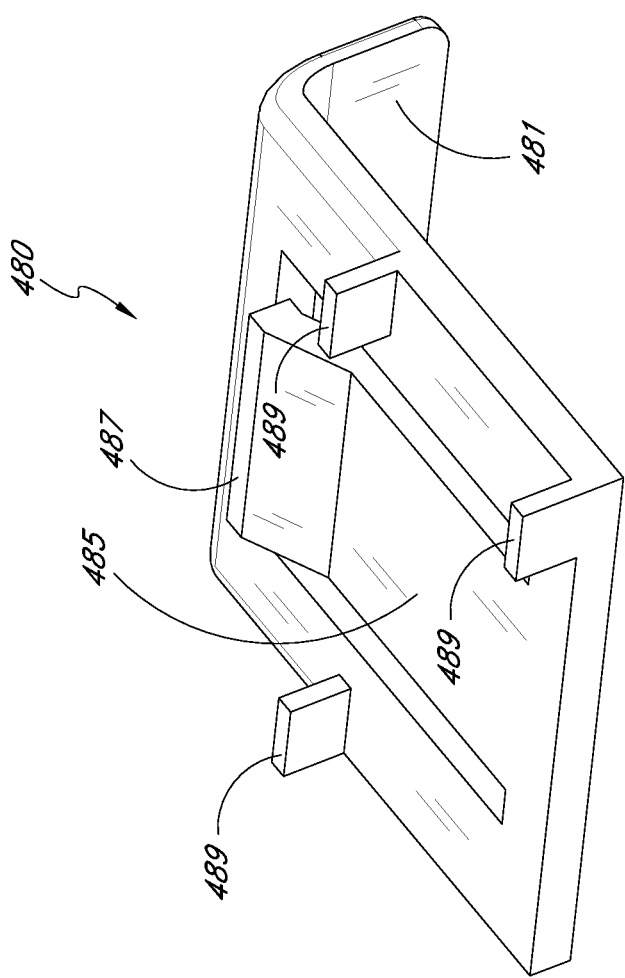
FIG. 27 is a perspective view of the compactor actuator of the apparatus of FIG. 21.
Figure 28:
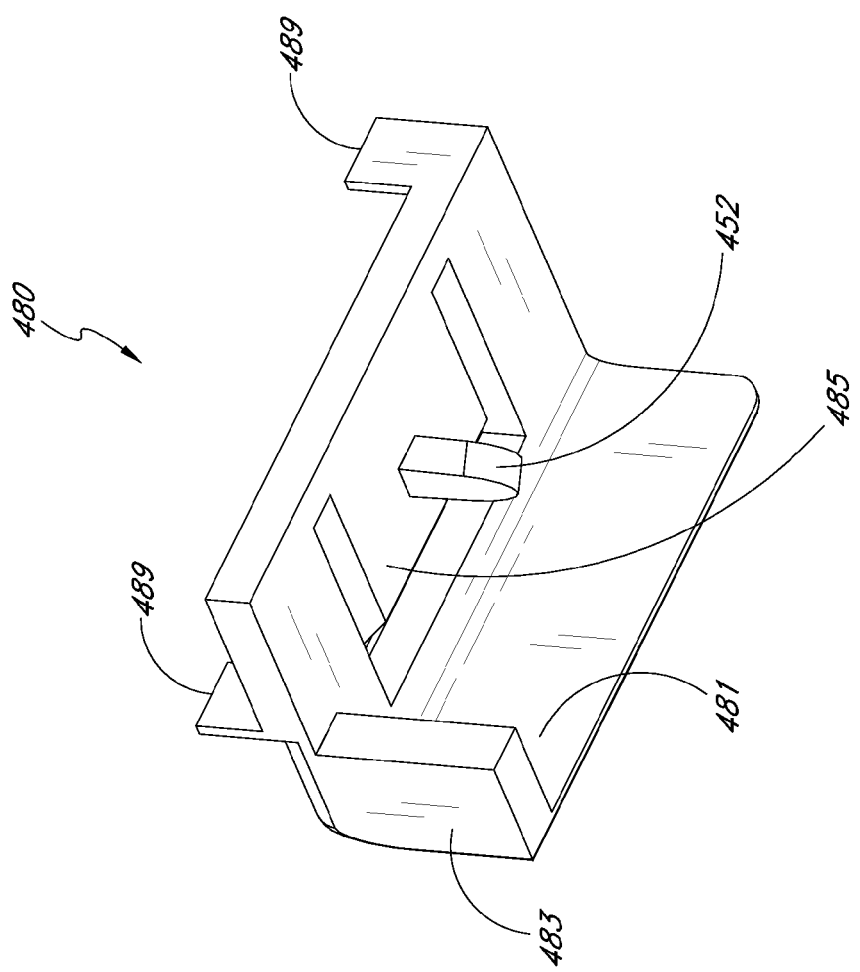
FIG. 28 is a second perspective view of the compactor actuator of the apparatus of FIG. 21.
Figure 29:
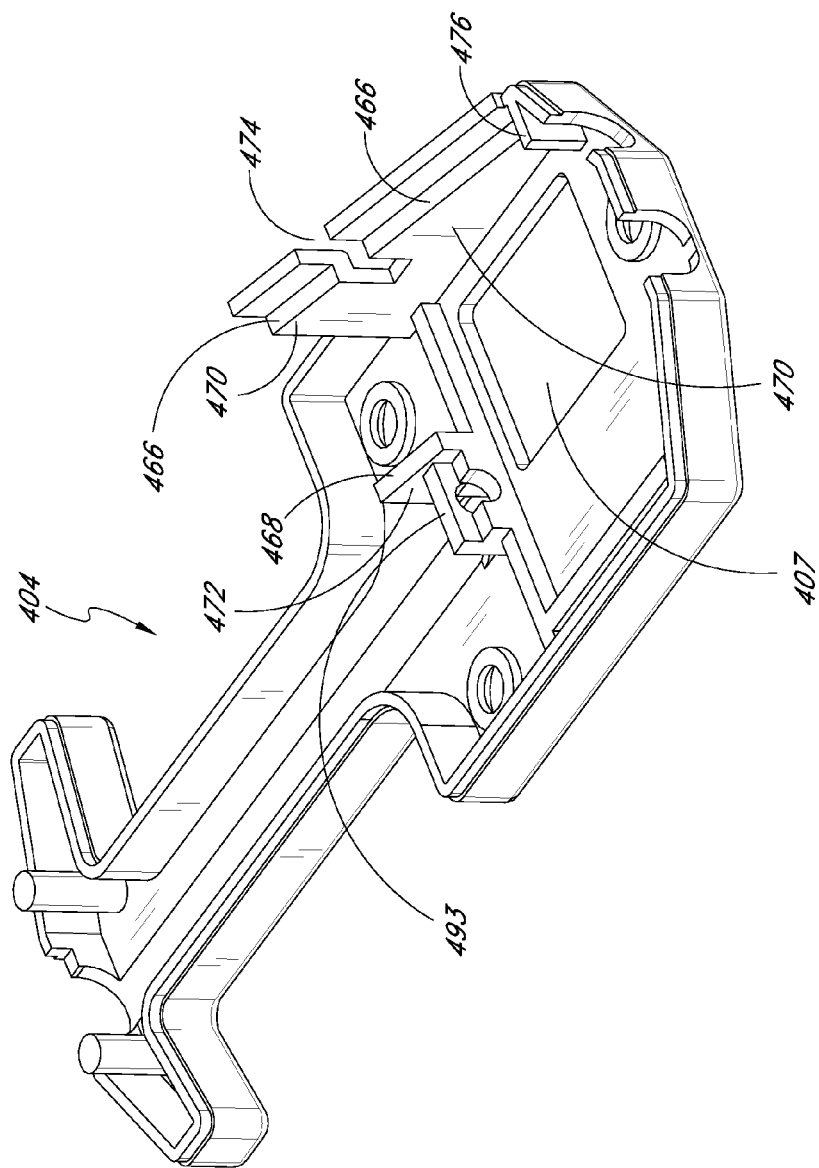
FIG. 29 is a perspective view of the lower housing of the apparatus of FIG. 21.

FIGS. 27-28 depict a preferred configuration of the compactor actuator 480. The actuator 480 preferably comprises a unitary member having a generally longitudinal handle 481 and a generally lateral guide rib 483. A spring member 485 extends laterally across an opening formed in the upper surface of the compactor actuator 480, and forms a spring tab 487 on its free end. Extending generally upward from the upper surface of the compactor actuator 480 are a number of guide projections 489, the upper ends of which are disposed within corresponding compactor guides 482 (see FIG. 22) formed on the inward upper surface of the upper housing 402. In the depicted embodiment, each of the compactor guides 482 comprises a generally longitudinal slot 484 and a generally lateral slot 486 which are joined in an "L" configuration. The lateral slot(s) 486 may extend purely laterally, or (in the depicted embodiment) they may be angled slightly forward, forming an angle of slightly more than 90 degrees with the corresponding longitudinal slot(s) 484.

Thus, the compactor actuator 480 is employed to move and guide the upper lens compactor 440 along a range of motion (similar to that of the upper lens compactor 240 of the apparatus 200) between a home position, first compacted position and second compacted position. At the home position, the upper lens compactor 440 is rearwardly disposed on the ribs 470, 472, with the first upper bearing surface 460 resting on the first lower bearing surface 466 and straddling a gap 474 formed in the surface 466/rib 470, and with the second upper bearing surface 462 resting on the second lower bearing surface 468. In one embodiment, the rearward edges of the surfaces 460 and 466 (and/or those of the surfaces 462 and 468) are aligned when the upper lens compactor 440 is in the home position.

From the home position, the actuator 480 and compactor 440 can be moved longitudinally forward by appropriate manipulation of the handle 481, to the first compacted position in which the first upper bearing surface 460 may remain on the first lower bearing surface 466, but forward of the gap 474, and the second upper bearing surface 462 is displaced forward of, and no longer rests on, the second lower bearing surface 468. In addition, the lateral guide rib 483 is longitudinally aligned with or forward of the gap 474, thereby permitting (subsequent) inward lateral movement of the actuator 480 and compactor 440, and the guide projections 489 are disposed at the forward ends of the longitudinal slots 484 of the corresponding compactor guides 482 (see FIG. 22). The first compacted position is, in one embodiment, further characterized by relative situation of the compactors 410, 440, bearing faces 412, 442, channels 414, 444, edges 418, 448, etc. in a manner similar to that depicted in FIGS. 16-17 with regard to the apparatus 200. In another embodiment, the first compacted position is still further characterized by contact between a forward edge of the upper lens compactor 440 and a stop member 476 formed on the lower housing 404.

From the first compacted position, the actuator 480 and compactor 440 can be moved generally laterally inward to the second compacted position. The second compacted position is, in one embodiment, characterized by relative situation of the compactors 410, 440, bearing faces 412, 442, channels 414, 444, edges 418, 448, etc. similar to that depicted in FIG. 18 with regard to the apparatus 200. As the compactor 440 and actuator 480 advance laterally inward, their motion is guided by the interaction of the guide projections 489 and the lateral slots 486 of the corresponding compactor guides 482, until the second compacted position is reached. In addition, the lateral guide rib 483 moves laterally into the housings 402, 404 through the gap 474. In one embodiment, the spring member 485 and spring tab 487 of the actuator 480 move sufficiently laterally inward to cause the outer edge of the tab 487 to engage the inner edge of a locking ridge 488 (see FIG. 22) formed on the upper housing 402. The spring member 485 prevents disengagement of the tab 487 and ridge 488, thereby preventing backward/outward lateral movement of the actuator 480 and upper lens compactor 440, once the second compacted position has been reached. This in turn ensures the creation of a rigid, stable "cylinder" at the meeting of the upper and lower insertion channels 414, 444 in the second compacted position, and a smooth longitudinal advancement of the compacted IOL from the "cylinder" into the delivery probe 406. Where employed, the spring member 485, tab 487 and ridge 488 also cooperate to make the apparatus 400 a single-use device, ensuring that factory-controlled standards for sterility, suitability of IOL type, etc. may be enforced with respect to each use of an apparatus 400.

Figure 21:
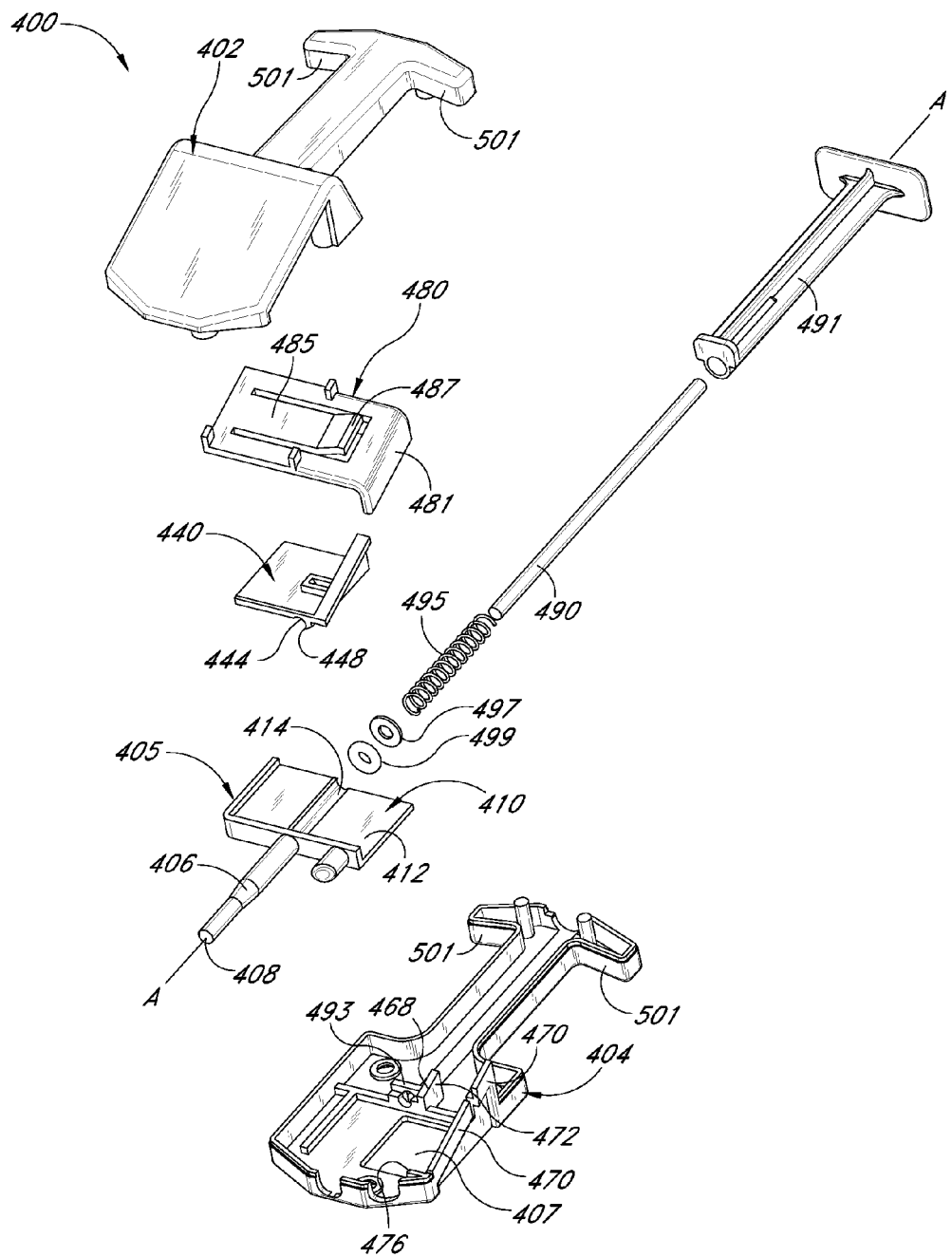
FIG. 21 is an exploded view of a second embodiment of an apparatus for compacting and/or inserting an intraocular lens.
Figure 22:
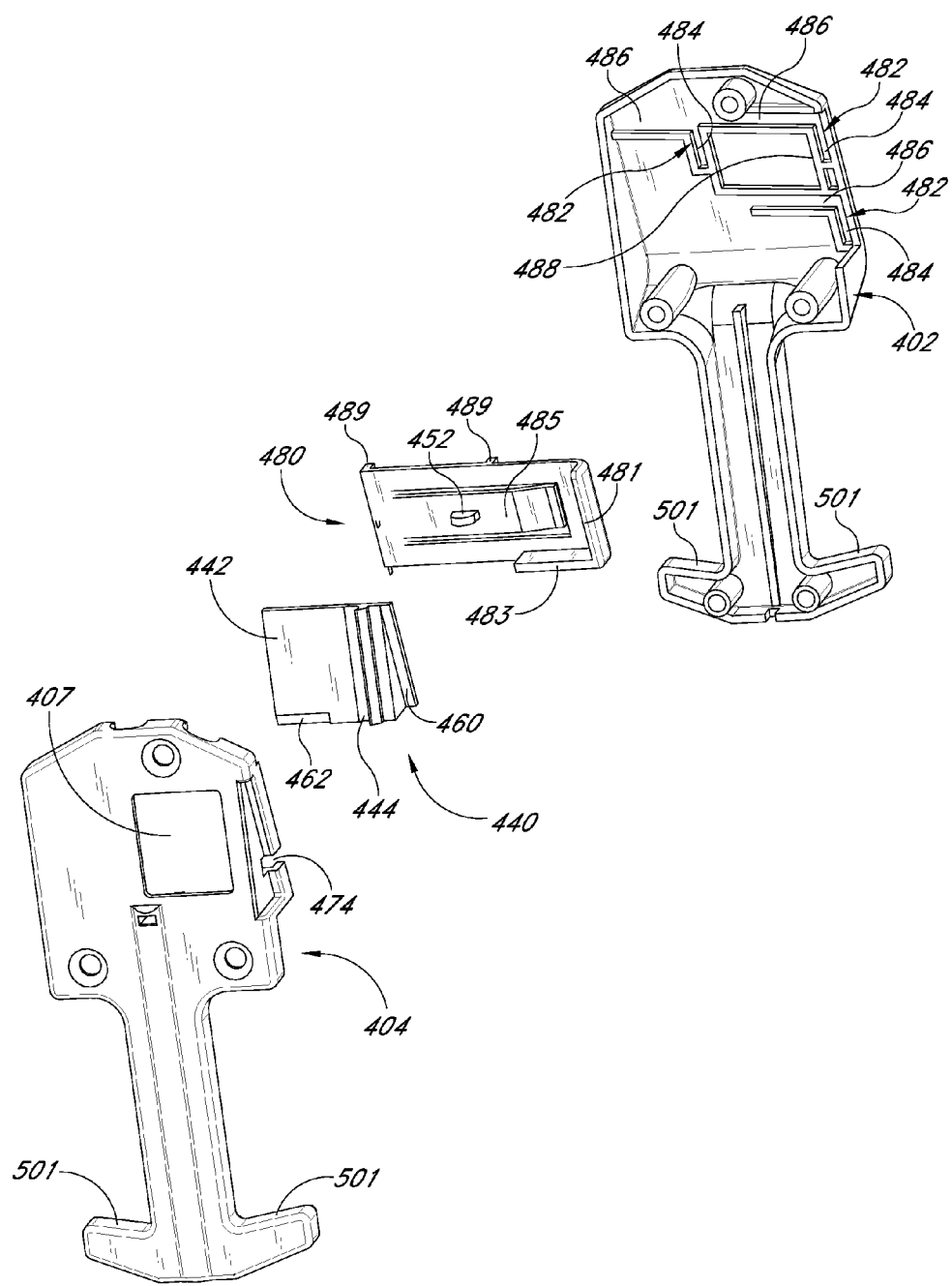
FIG. 22 is a second, partial exploded view of the apparatus of FIG. 21.
Figure 23:
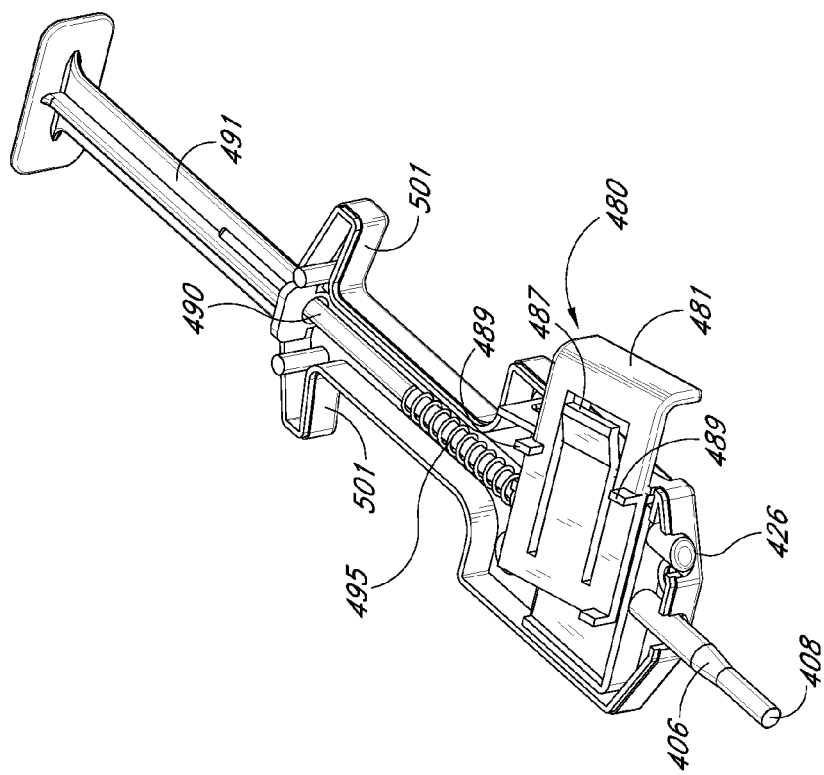
FIG. 23 is a perspective view of the apparatus of FIG. 21, with the upper housing removed for clarity.

With further reference to FIGS. 21-22, the apparatus 400 further comprises a generally cylindrical driving member 490 which is disposed along the delivery axis A-A. (Where the delivery lumen 408 has an oval cross-section, the driving member 490 may have a similarly oval cross-section.) The rearward end of the driving member 490 is received in a plunger 491 which is slidably disposed between the upper and lower housings 402, 404. The lower housing 404 forms a driving member guide 493 situated on the delivery axis A-A. Via appropriate manipulation of the plunger 491, the driving member 490 is longitudinally moveable from a retracted position (shown in FIG. 23), in which the forward end of the driving member 490 is situated in the driving member guide 493, forward through the lower insertion channel 414 (or between the insertion channels 414, 444 when the upper lens compactor 440 is in the second compacted position), thereby urging the IOL 120 forward and into the delivery lumen 408 of the delivery probe 406. Further advancement of the driving member will then extrude the IOL from the forward end of the delivery probe 406.

A spring 495, washer 497 and O-ring 499 may be situated surrounding the driving member 490 between the driving member guide 493 and the plunger 491. In addition, finger grips 501 may be provided on the upper and/or lower housings 402, 404 to facilitate holding the apparatus 400 between the thumb and forefingers, in a "syringe" fashion, with the thumb on the rear of the plunger 491 and one forefinger on each of the finger grips 501. This arrangement likewise facilitates single-handed operation of the apparatus 400 when delivering/inserting an IOL situated in the lower insertion channel 414. The spring 495 provides resistance and tactile feedback when a user is urging the driving member 490 forward with the plunger 491; if desired, the spring 495 and plunger 491 may be sized to reach an abutting relation (and thereby provide this resistance/feedback) once the forward end of the plunger 491 has entered the delivery lumen 408.

Accordingly, the apparatus 400 may be employed to deliver or insert an IOL, such as the IOL 120, into an eye, such as a human eye. In doing so, the user/physician first accesses an insertion location (e.g., the capsular bag, anterior chamber, etc) within the eye via any suitable technique, for example, by making a small incision or series of small incisions in the anterior structures of the eye. If necessary, the natural crystalline lens is removed via a suitable technique such as phacoemulsification. Through the incision(s) the physician inserts the forward end of the delivery probe 406, preferably after compacting the IOL as detailed above and, if desired, after advancing the IOL partway through the lumen 408 of the delivery probe 406. With the end of the delivery probe in place, the physician extrudes the IOL from the probe 406, thereby inserting the IOL in the eye. (By employing the apparatus 400, the compacting and delivery/insertion may be done without opening the housing 402/404 or otherwise manually accessing the IOL.) Upon departure from the probe 406, the IOL "un-compacts" by virtue of its elasticity, returning substantially to its unstressed condition. The physician then withdraws the probe 406 and, if necessary, adjusts the positioning of the IOL within the eye. Upon satisfactory positioning of the IOL, the physician closes the incision(s) to complete the operation.

Various embodiments of the apparatus 200/400 disclosed herein advantageously facilitate delivery of an IOL into the eye of a patient without need for a physician to handle the IOL or manually load it into an insertion device. For example, the IOL may be positioned within the lens compactor (e.g., between the upper and lower lens compactors) of the apparatus 200/400 during manufacture/assembly of the apparatus. The apparatus 200/400, with the IOL thus disposed inside the lens compactor, may then be sterilized as a unit, either at the point of manufacture or at some downstream location. Where appropriate, the sterilized apparatus-IOL assembly may be contained in a sterile package, wrapper, bag, envelope, etc. in which the apparatus-IOL assembly may remain until arrival at the point (or time) of use. (The apparatus-IOL assembly may be sterilized before and/or after placement in the package, etc.) This further facilitates a simple point-of-use procedure for medical personnel involved in implanting the IOL contained in the apparatus 200/400: after opening (any) packaging, the physician, or other medical personnel, can compact and insert the IOL using the apparatus 200/400 as discussed above, without (any need for) removing the IOL from the apparatus. Accordingly, there is no need to handle the IOL or manually load it into an insertion device at the point of use, both of which can be difficult and tedious, and can compromise the sterility of the IOL.

Figure 30:
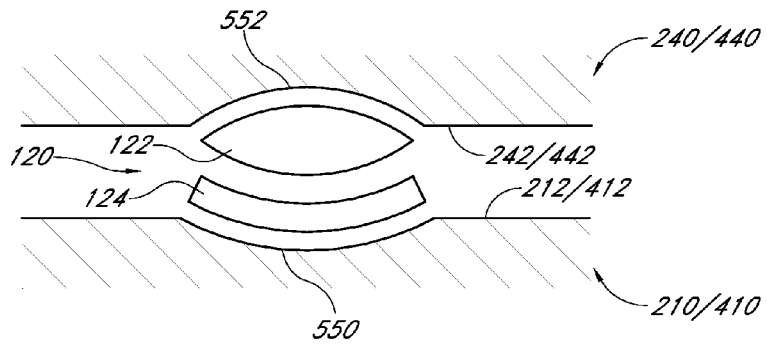
FIG. 30 is a schematic, cross-sectional view of alternative engagement faces for use with the disclosed apparatus.
Figure 31:
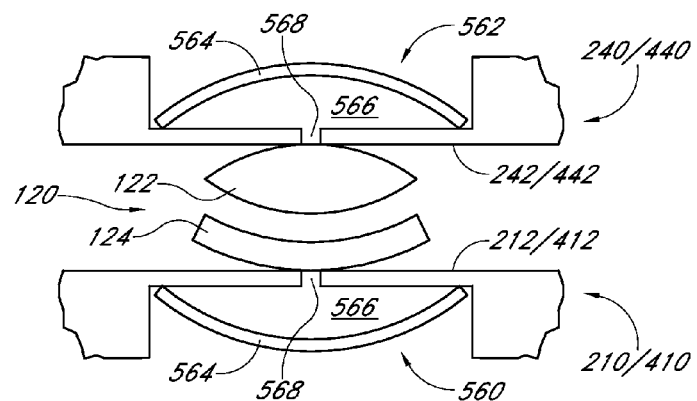
FIG. 31 is a schematic, cross-sectional view of vacuum-type engagement faces for use with the disclosed apparatus.
Figure 32:
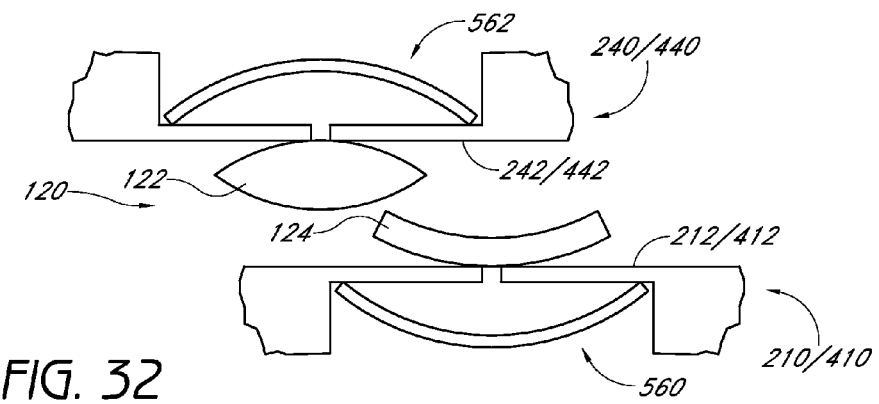
FIG. 32 is a schematic, cross-sectional view of vacuum-type engagement faces for use with the disclosed apparatus, with the upper lens compactor in the first compacted position.
Figure 33:
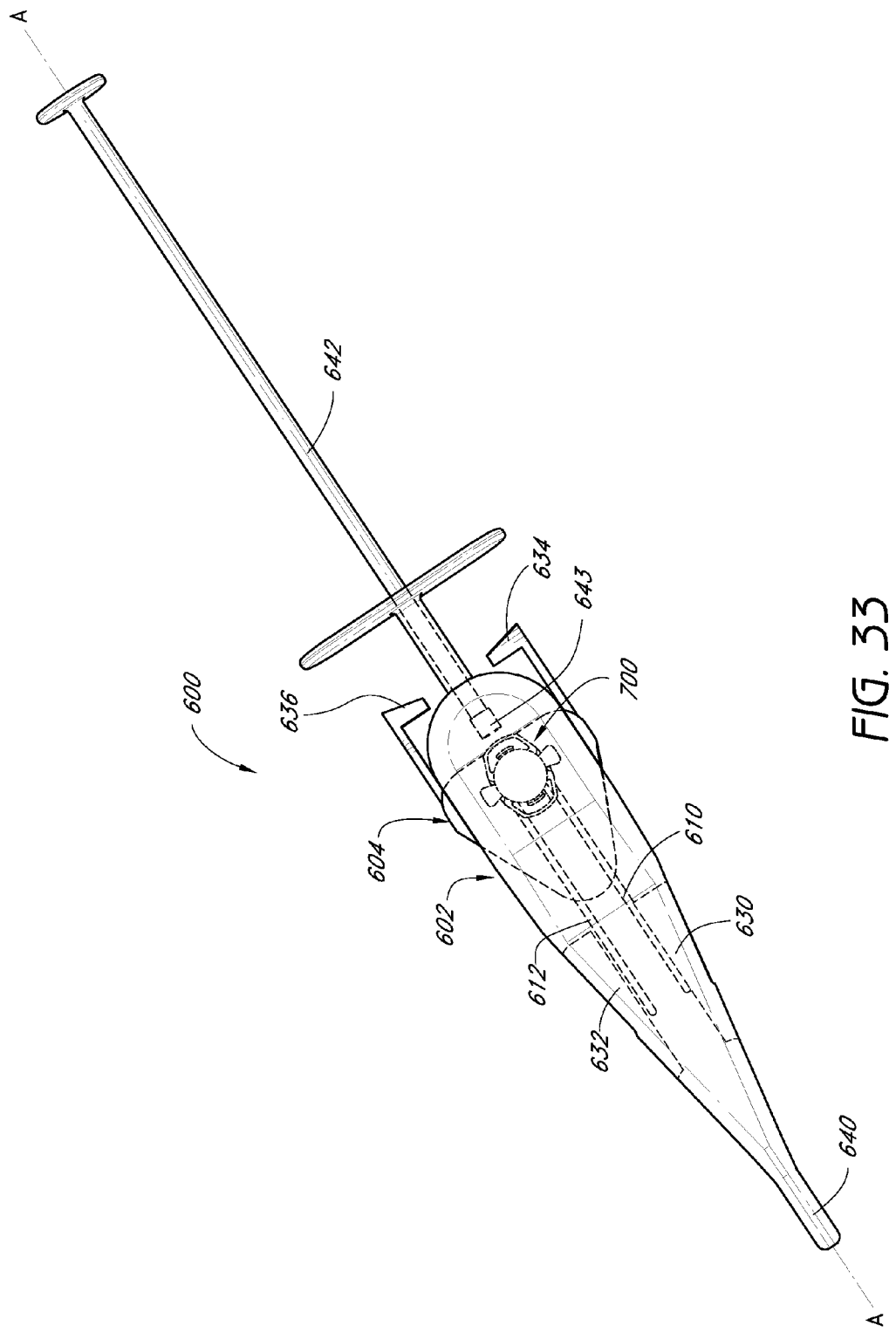
FIG. 33 is a perspective view of another embodiment of an injector for an intraocular lens system.

FIGS. 30-32 depict alternative structures that may be employed in connection with one or both of the lower and upper engagement faces 212/412, 242/442, instead of or in addition to the generally flat surfaces described above. For example, FIG. 31 depicts the use of one or more pockets 550, 552 formed in the faces 212/412, 242/442. The pockets 550, 552 may be suitably shaped (e.g. as partial, substantially cylindrical or spherical shells, or with a rectangular or other polygonal profile) to grip the respective viewing elements 124, 122. In a further embodiment, the pocket(s) 550, 552 may be formed from a material, such as any of the materials discussed above, having an adhesive affinity for the material(s) employed to construct the outer faces of the viewing elements.

As seen in FIGS. 31-32, vacuum grips 560, 562 may be employed in connection with the engagement face(s) 212/412, 242/442. In the depicted embodiment, each vacuum grip 560, 562 comprises a domelike button 564 enclosing a vacuum chamber 566 in fluid communication with a relief opening 568 formed in the respective engagement face(s) 212/412, 242/442 which is positioned to abut the respective viewing element(s) 124, 122. Thus, depression of the button(s) 564 expels air from the relief openings 568, and the resilient properties of the button(s) 564 are sufficient to urge the button(s) 564 toward their original position. The negative pressure thereby created in the vacuum chamber(s) 566 draws the viewing element(s) 124, 122 against the engagement face(s) 212/412, 242/442. With the viewing elements so gripped, the compactors 210/410, 240/440 may be relatively moved to place the IOL 120 in the first compacted configuration shown in FIG. 32.

As yet another alternative, one or both of the engagement face 212/412, 242/442 may be suitably roughened to engage the viewing elements 122, 124. Such surface roughening may be employed on its own, or in connection with any of the alternatives discussed herein for constructing the engagement face 212/412, 242/442. In one embodiment, the surfaces in question are sanded; as one example, 100 grit sandpaper may be employed. In other embodiments, the surfaces may be ribbed, knurled, etc.

In further embodiments of the apparatus 200/400, the lower housing 204/404, lower lens compactor 210/410 and/or upper lens compactor 240/440 may be configured such that the upper lens compactor 210/410 is moveable only from the first compacted position to the second compacted position. In other words, the first compacted position replaces the home position as the "start" location of the upper lens compactor 240/440, which can move from the first compacted position to the second compacted position in the manner already described. Any or all of the structures described above as facilitating longitudinal movement of the upper lens compactor 210 between the home and first compacted positions may be omitted, if desired. The balance of the structure and function of the apparatus 200/400 preferably remains as described above.

Such a modified apparatus 200/400 is particularly useful for compacting and/or inserting a single-lens IOL, such as (but not limited to) the IOL 100 described above. Alternatively, a multiple-lens IOL, such as (but not limited to) the IOL 120 described above, may be compacted and/or inserted with this modified apparatus. In one embodiment, the multiple-lens IOL is disposed or stored in the compactor in the first compacted condition described above, when the upper lens compactor is in the first compacted position (again, the "start" location of the upper lens compactor). In another embodiment, the multiple-lens IOL is disposed or stored in the compactor in the substantially unstressed condition described above, when the upper lens compactor is in the first compacted position.

FIGS. 33-44 depict an embodiment of an injector 600 for injecting an IOL 700 into the eye of a patient. In one embodiment, the IOL 700 comprises an accommodating intraocular lens having two or more interconnected viewing elements or two or more interconnected optics. One, both or all of the viewing elements of the IOL 700 may comprise an optic or lens having refractive (or diffractive) power. Alternatively, one, both or all of the viewing elements may comprise an optic with a surrounding or partially surrounding perimeter frame member or members, with some or all of the interconnecting members attached to the frame member(s). As a further alternative, one of the viewing elements may comprise a perimeter frame with an open/empty central portion or void located on the optical axis, or a perimeter frame member or members with a zero-power lens or transparent member therein. In still further variations, one of the viewing elements may comprise only a zero-power lens or transparent member.

In another embodiment, the IOL 700 may comprise any of the various embodiments of accommodating intraocular lenses described in U.S. Pat. No. 7,198,640, issued on Apr. 3, 2007, titled ACCOMMODATING INTRAOCULAR LENS SYSTEM WITH SEPARATION MEMBER, or any of the various embodiments of accommodating intraocular lenses described in U.S. Patent Application Publication No. 2005/0234547, published Oct. 20, 2005, titled INTRAOCULAR LENS. The entire disclosures of the above-mentioned publications are hereby incorporated by reference herein and made a part of this specification. In still other embodiments, the IOL 700 may comprise a single-optic system, of the accommodating or non-accommodating type.

In one embodiment, where the IOL 700 comprises a dual-optic system (or, more generally, a dual-viewing-element system), the injector 600 manipulates the IOL 700 in two stages while moving the IOL 700 along a single axis, specifically a longitudinal axis A-A of the injector 600. (The longitudinal axis A-A is also referred to herein as an "injection axis" of the injector.) In a first stage of manipulation, the injector 600 displaces first and second optics 702, 704 of the IOL 700 into a non-coaxial relation (see FIGS. 34, 38), in which the optical axes B-B, C-C of the first and second optics 702, 704 are displaced relative to each other. Displacing the optics 702, 704 and their respective optical axes in this manner reduces the overall thickness of the IOL 700. In a second stage of manipulation, the injector 600 compacts, folds or crushes the (thus-displaced) IOL 700 into an injection channel 635 (see FIGS. 35, 36, 40) oriented along the injection axis A-A of the injector 600.

In one embodiment, the first optic 702 comprises an anterior optic and the second optic 704 comprises a posterior optic. The terms "anterior" and "posterior" are derived from the positions preferably assumed by the optics 702, 704 upon implantation of the IOL 700 into an eye.

The injector 600 generally comprises a housing 602 and an actuator/lens carrier or "sled" 604 slidably mounted on the housing 600. The IOL 700 is (initially) stored in the housing 602 in a home position, in a substantially unstressed storage condition (see FIG. 33; also known as a "neutral" or "packaged" condition). In the storage condition the optics 702, 704 are arranged substantially coaxially, with their respective optical axes B-B, C-C substantially aligned or collinear, and with their optical axes B-B, C-C oriented substantially orthogonal to the longitudinal axis A-A of the injector 600/housing 602. As the user advances the actuator 604 distally or forward along the housing, actuator pins 606, 608 formed on the actuator 604 (see FIG. 39) simultaneously advance forward in slots 610, 612 formed in the bottom of the housing 602. Because the pins 606, 608 protrude through the slots 610, 612 and engage one of the viewing elements of the IOL 700, the forward advance of the pins 606, 608 urges the IOL 700 forward or distally within the housing, generally along the slots 610, 612 and along the longitudinal axis A-A.

Figure 34:
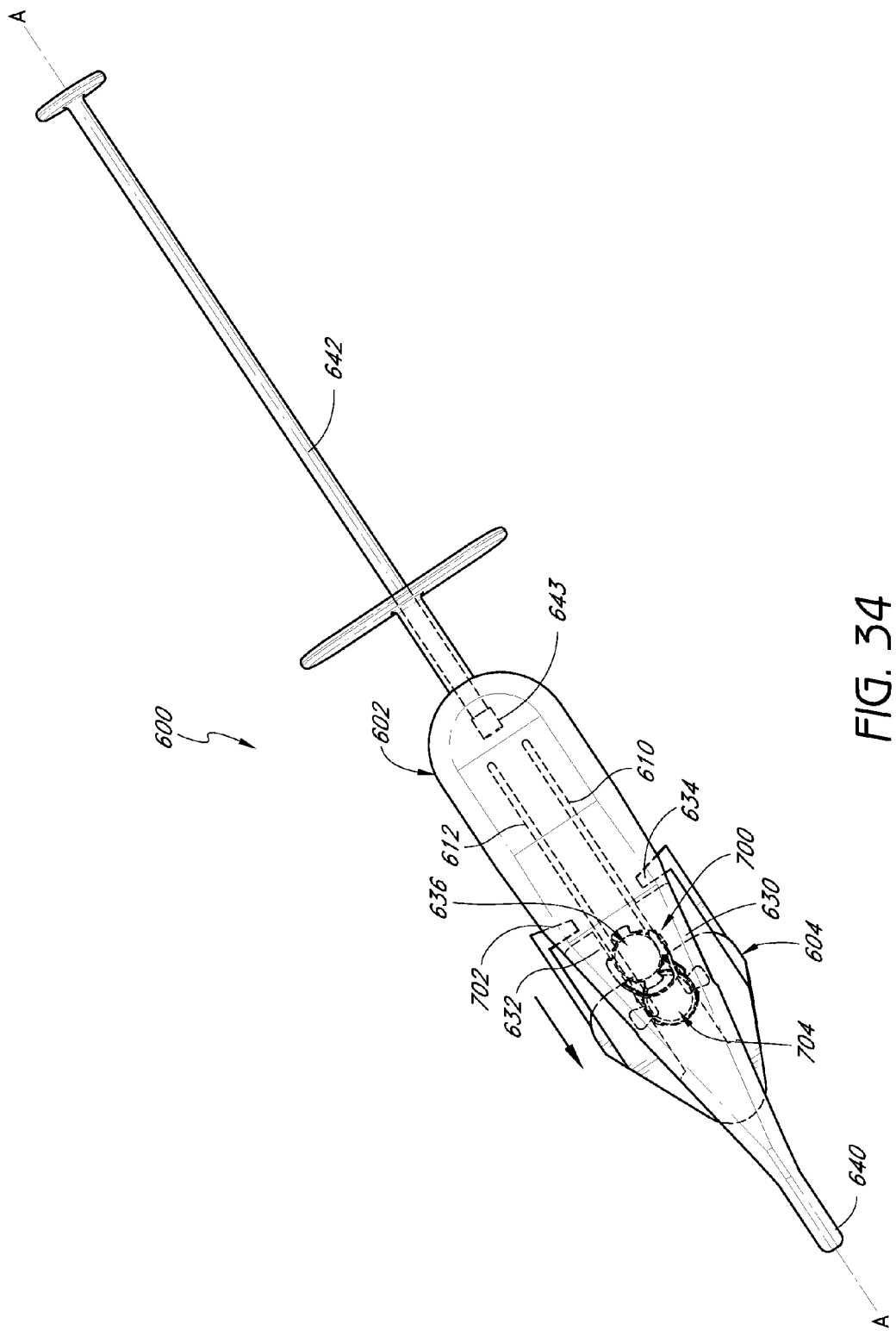
FIG. 34 is a perspective view of the injector of FIG. 33, with the lens system in a displaced condition.
Figure 38:
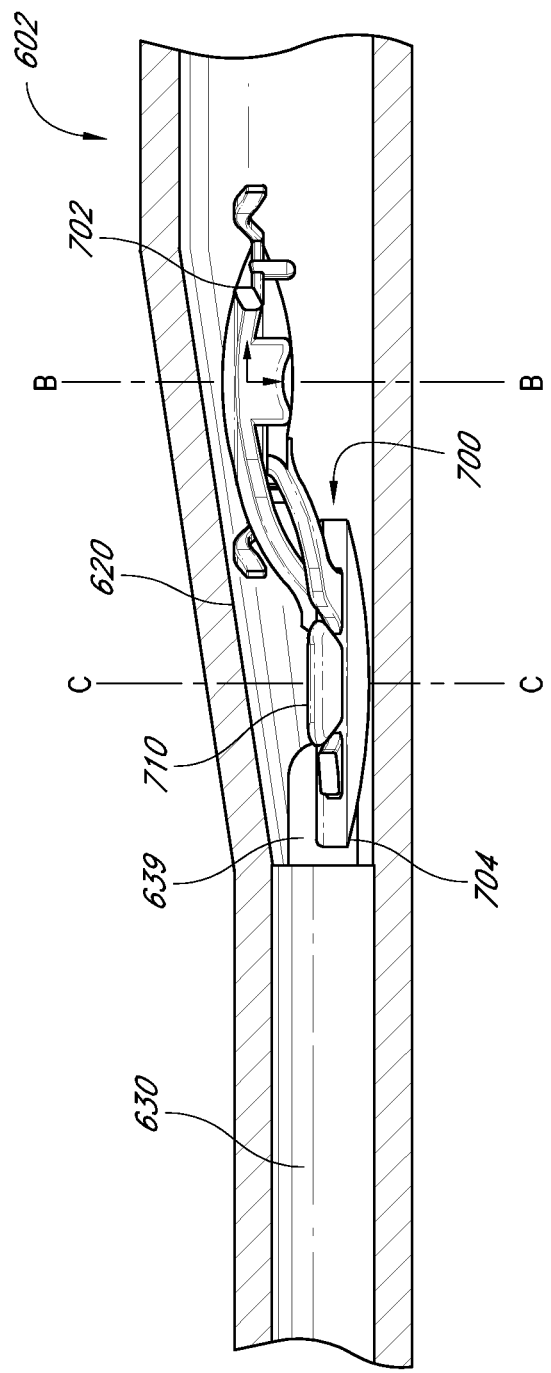
FIG. 38 is a partial side cross-sectional view of a housing of the injector of FIG. 33.

As the IOL 700 is advanced forward, the first optic 702 comes into contact with an inclined portion or ramp portion 620 of the housing 602 (see FIG. 38). The inclined portion 620 forces the first optic 702 to move rearward and downward relative to the advancing second optic 704. Thus the first optic 702 falls behind the advancing second optic 704, urging the optics 702, 704 into a flatter, non-coaxial "displaced" condition as shown in FIGS. 34 and 38. As seen in FIG. 34, the optics 702, 704 preferably remain disposed substantially along the longitudinal axis A-A of the injector 600/housing 602 when the IOL 700 is in the displaced condition shown in FIGS. 34 and 38. In one embodiment, the optics 702, 704 of the IOL 700 are relatively displaced into a condition in which the optics do not "overlap" at all, as viewed along the optical axis of either optic. In still another embodiment, the optics 702, 704 are relatively displaced until the optics 702, 704 are in substantially planar, side-by-side alignment (either overlapping or non-overlapping) such that the thickness of the IOL 700 is minimized.

The inclined portion 620 may be considered one type of "single-element engagement surface" as it is one of a variety of suitable structures which may be employed to engage one, but not the other, of the viewing elements of a two-viewing-element IOL 700 as the IOL 700 advances distally through the injector housing 602.

After the optics 702, 704 have been relatively displaced as shown in FIG. 38, the IOL 700 and actuator 604 may be further advanced until the IOL 700 is situated between a pair of compacting members or wedge plates 630, 632 (see FIG. 34). Tabs 634, 636 formed on the actuator 604 (and extending through slots 638, 639 formed on the sides of the housing 602, upon sufficient advancement of the actuator 604) engage the compacting members 630, 632 and urge the members 630, 632 forward along with the IOL 700 and actuator 604.

As the compacting members 630, 632 move forward, they converge on the IOL 700, due to the tapered configuration of the members' outer edges and the housing 602. Each of the compacting members 630, 632 forms a corresponding face 631, 633 in the form of a half-channel on its inner edge (see FIG. 40). Consequently, the converging faces 631, 633 compact, crush and/or fold the IOL 700 (which is preferably urged into the "displaced" condition shown in FIGS. 34 and 38 before compacting) in the injection channel 635, which is formed at the meeting of the two members 630, 632 once the members have been driven all the way forward. The injection channel 635 thus formed is substantially aligned on the injection axis A-A with an injection probe or nozzle 640 formed by the housing 602, and a plunger 642. This injection channel 635, which preferably has a cross-section which substantially matches that of an inner lumen of the injector probe 640, holds the folded/crushed and displaced IOL 700 ready for further distal longitudinal movement into the injector probe 642.

Figure 35:
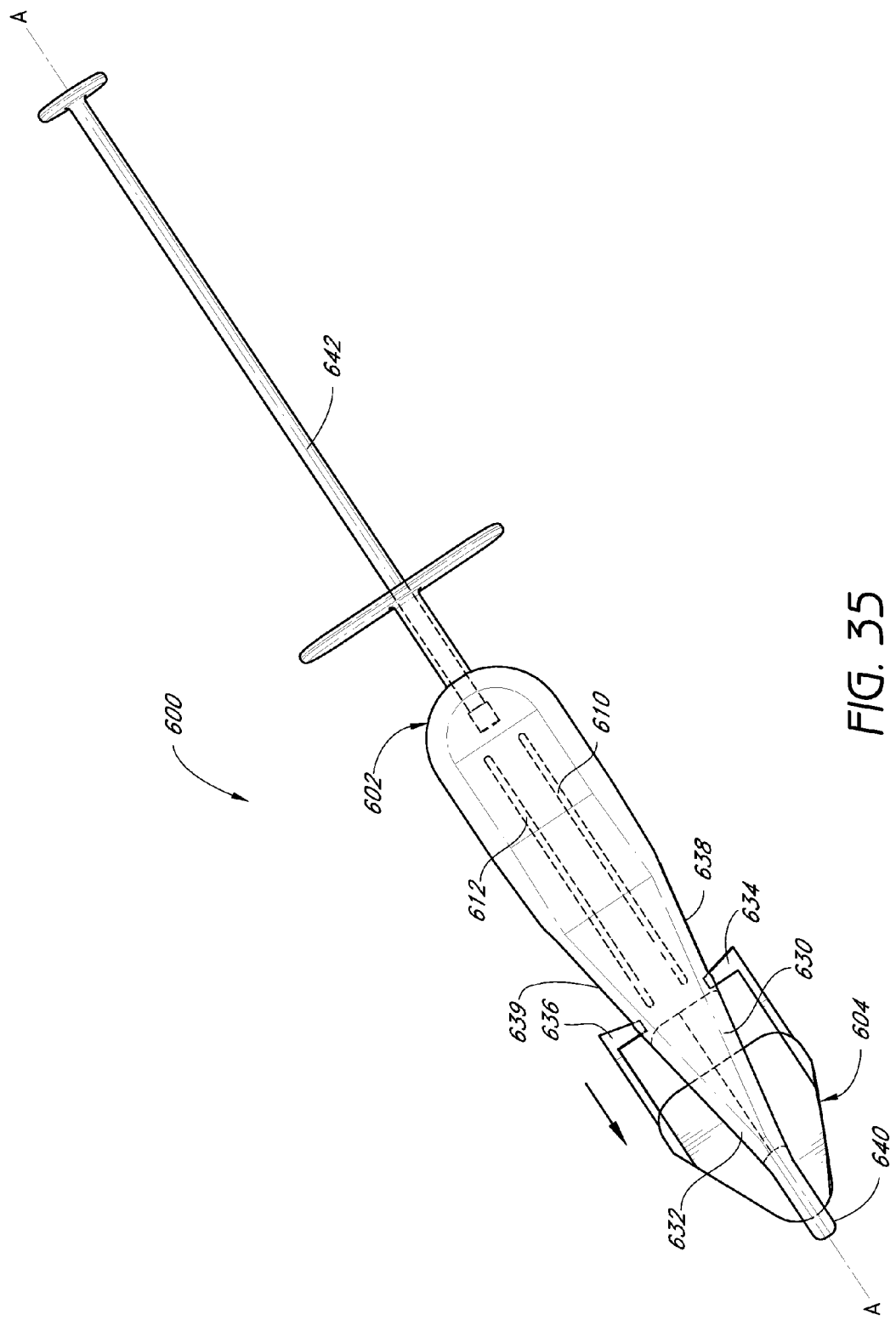
FIG. 35 is a perspective view of the injector of FIG. 33, with the lens system in a displaced and folded/crushed/compacted condition.
Figure 36:
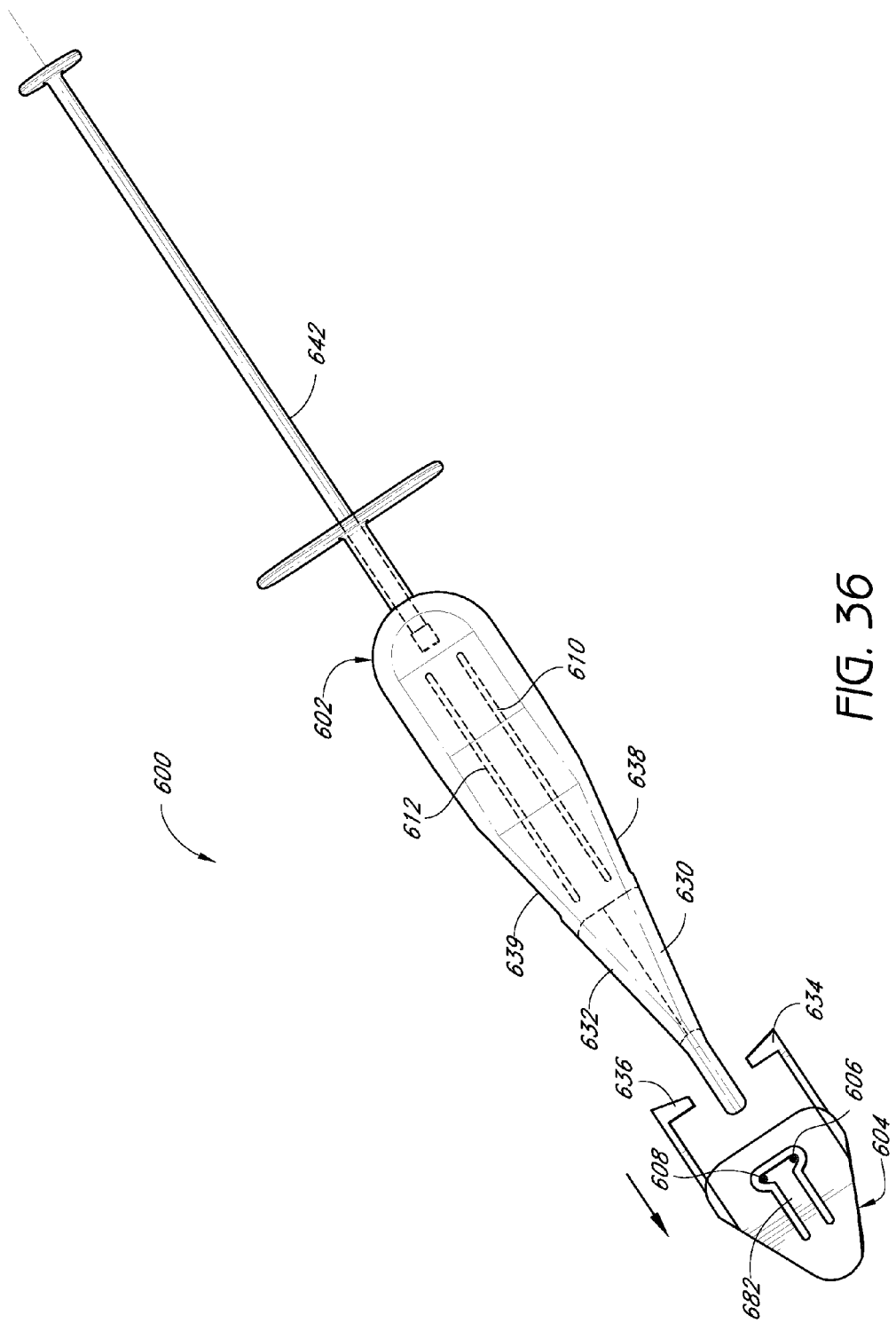
FIG. 36 is a perspective view of the injector of FIG. 33, with the lens system in the displaced and folded/crushed/compacted condition and an actuator thereof removed.

When the compacting members 630, 632 have reached the forwardmost/distalmost position just described and shown in FIG. 35, the members 630, 632 will have converged (and moved laterally) sufficiently for the tabs 634, 636 of the advancing lens carrier 104 to clear and disengage from the rearward surfaces of the members 630, 632. The lens carrier 604 may thus be further advanced distally, detached from the housing 602 and discarded (see FIG. 38).

Figure 41:
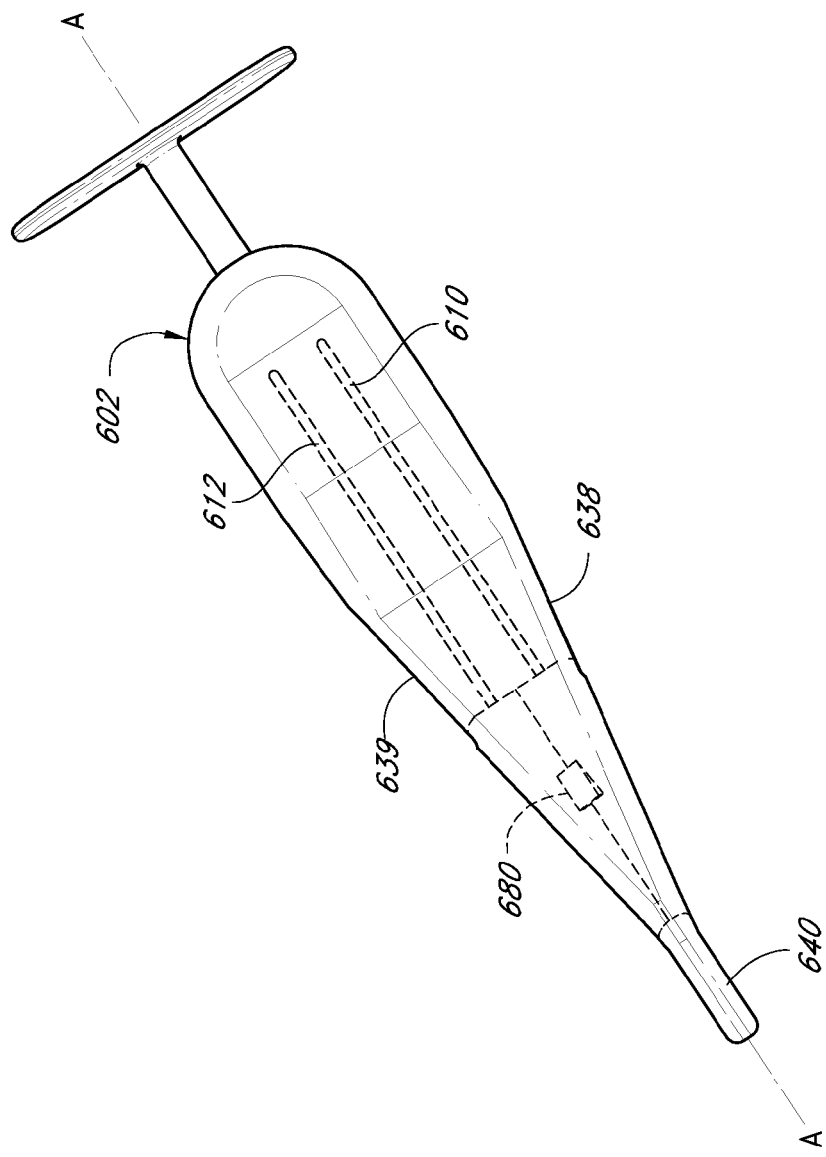
FIG. 41 is a perspective view of the housing.
Figure 42:
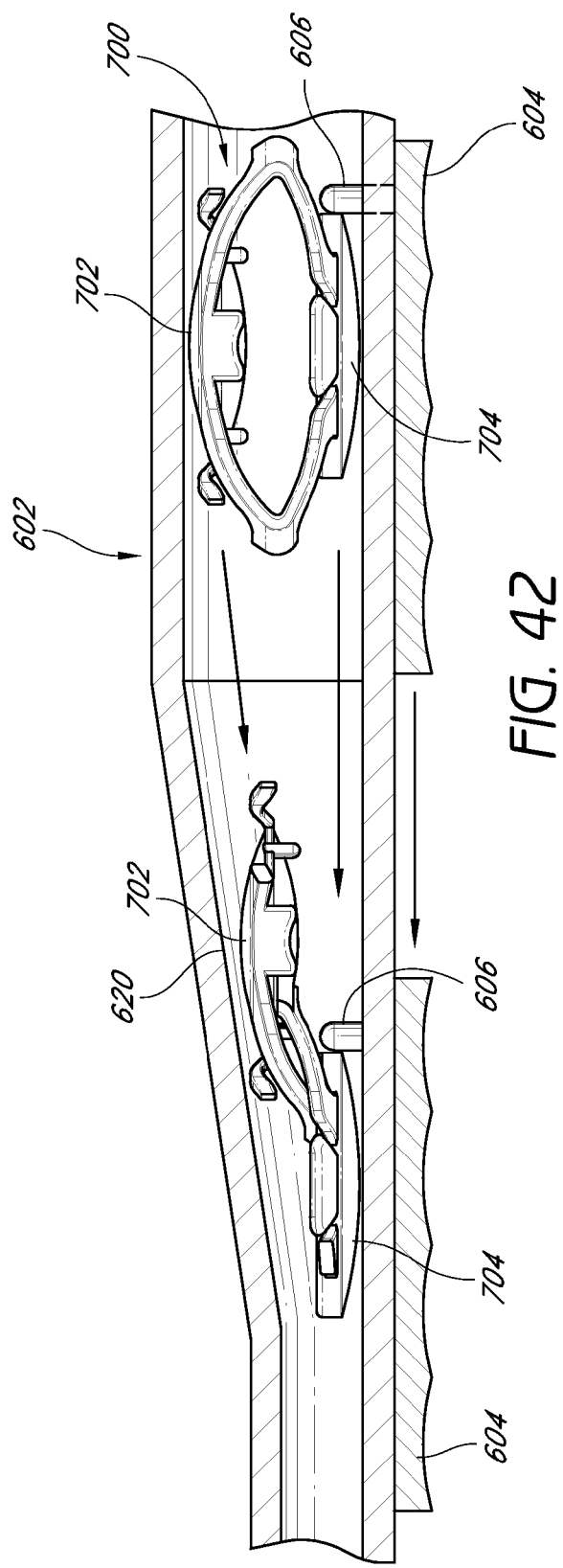
FIG. 42 is a side cross-sectional view of the operation of the actuator.
Figure 43:
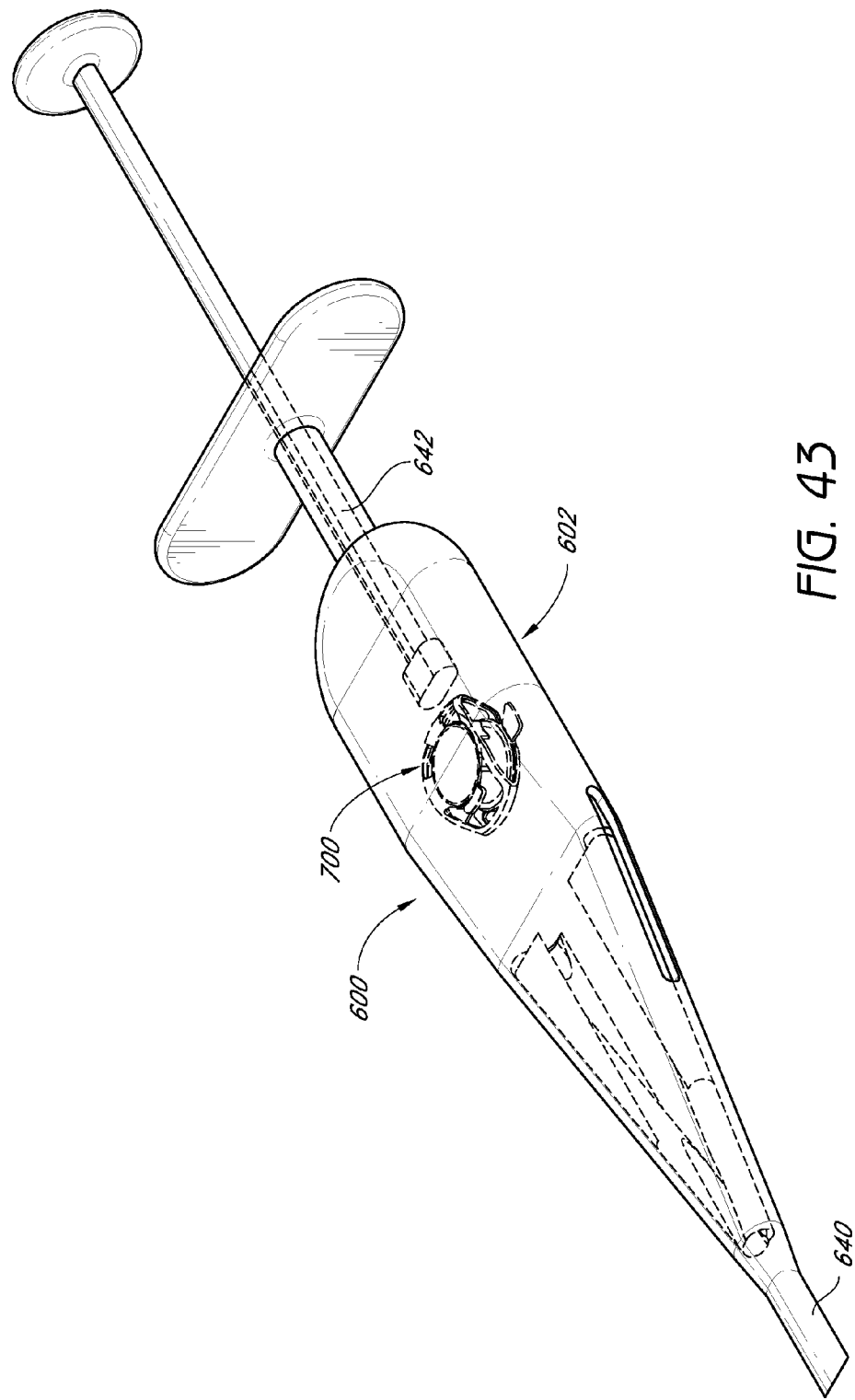
FIG. 43 is a perspective view of the injector.

As seen in FIG. 41, the housing 602 preferably forms a disengagement ramp 680 on its underside. The ramp 680 is positioned to force the pins 606, 608 of the lens carrier 604 to move downward and disengage from the IOL 700 (and, if desired, disengage from the slots 610, 612) as the IOL 700 moves between the compacting members 630, 632. The lens carrier preferably forms a flexible pin tab 682 (see FIGS. 36, 39) which is configured to contact the ramp 680 upon sufficiently distal movement of the lens carrier 604, and flex downward under the urging of the ramp 680, thus disengaging the pins 606, 608 as discussed above.

Figure 37:
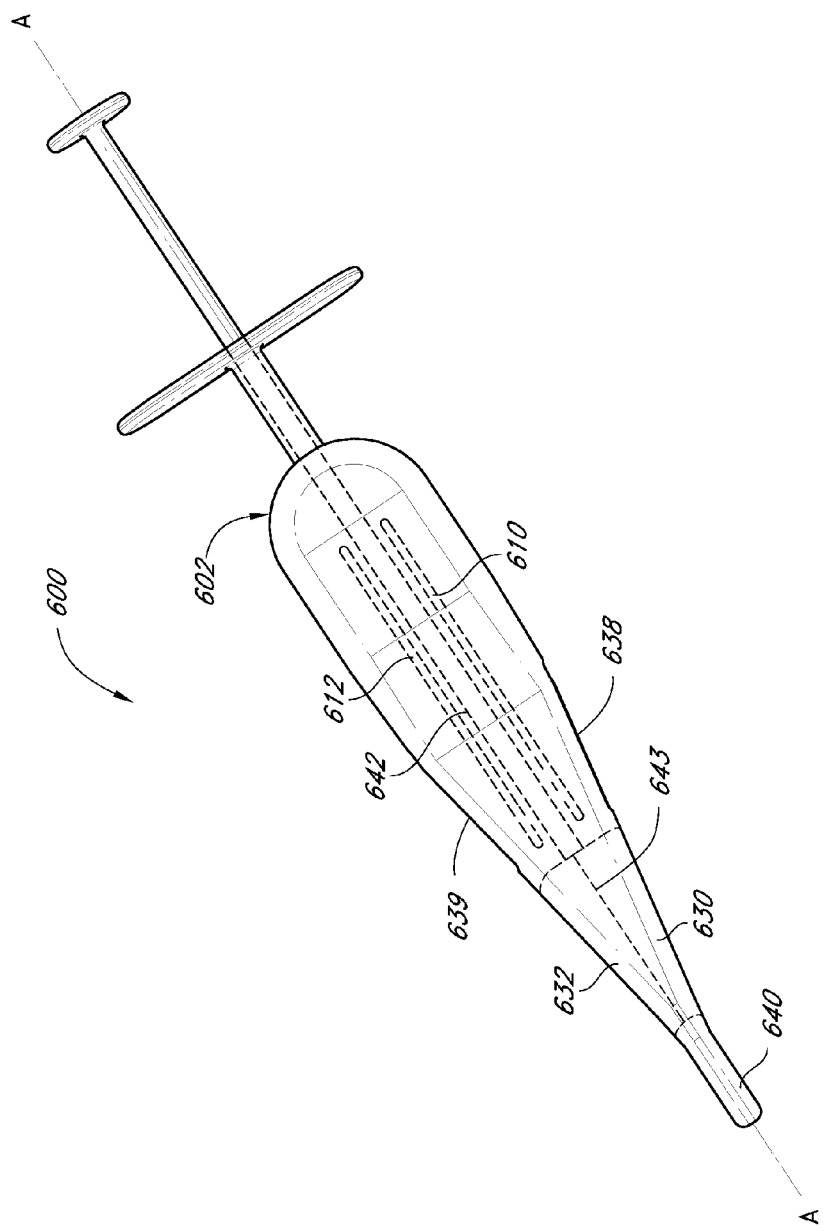
FIG. 37 is a perspective view of the injector of FIG. 33, with the lens system in the displaced and folded/crushed/compacted condition and a plunger thereof advanced forward.

Once the compacting members 630, 632 have folded or compacted the IOL 700, application of pressure to the plunger 642 drives the tip 643 of the plunger forward, into the injection channel 635 between the plates 630, 632 and against the "crushed" or "folded" IOL 700 disposed therebetween (see FIG. 37). With continued application of pressure, the plunger 642 urges the IOL 700 into the inner lumen of the probe 640. The end of the probe 640 may be inserted into the eye of a patient in the typical manner, for delivery of the IOL 700 from the tip of the probe.

Figure 44:
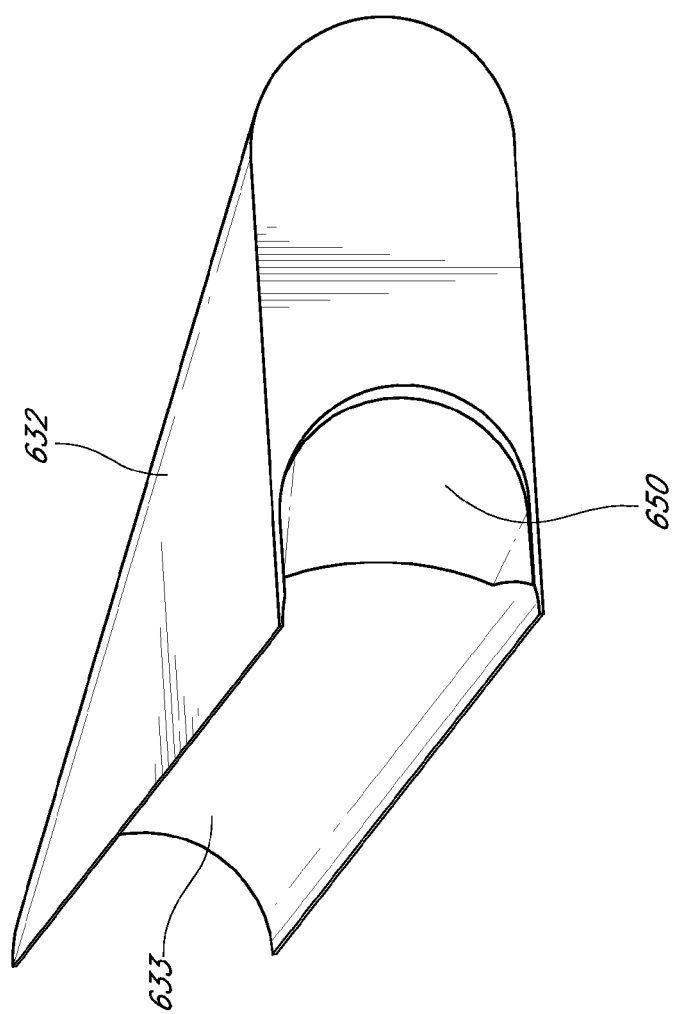
FIG. 44 is a rear detail view of one of the compacting members.

As seen in FIG. 44, each of the compacting members 630, 632 may include a lead-in 650 at the rearward or proximal end of the corresponding face 631, 633 to ensure that the tip 643 of the plunger 642 is easily inserted between the converged compacting members 630, 632.

Figure 45:
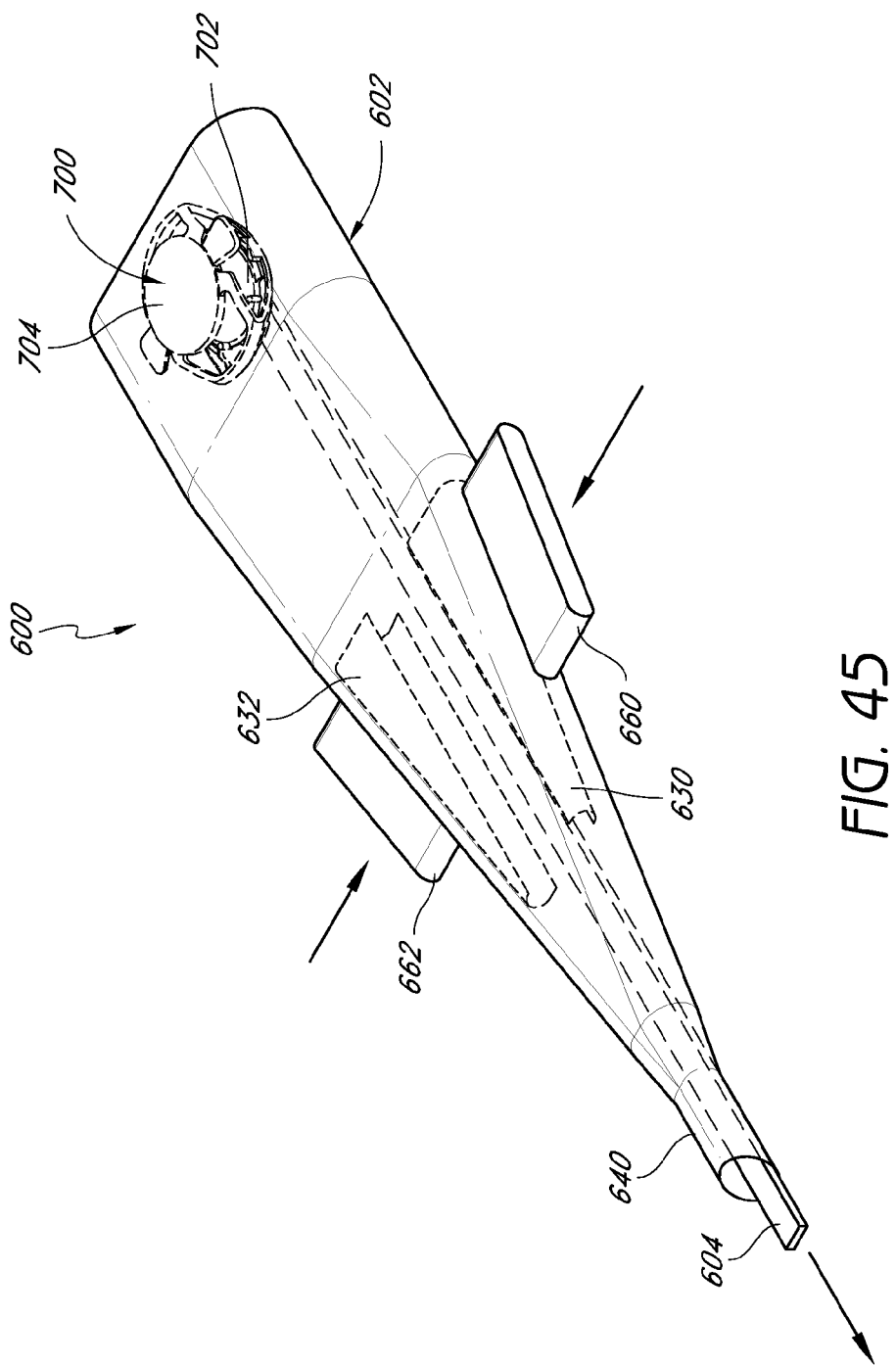
FIG. 45 is a perspective view of another embodiment of the injector.
Figure 46:
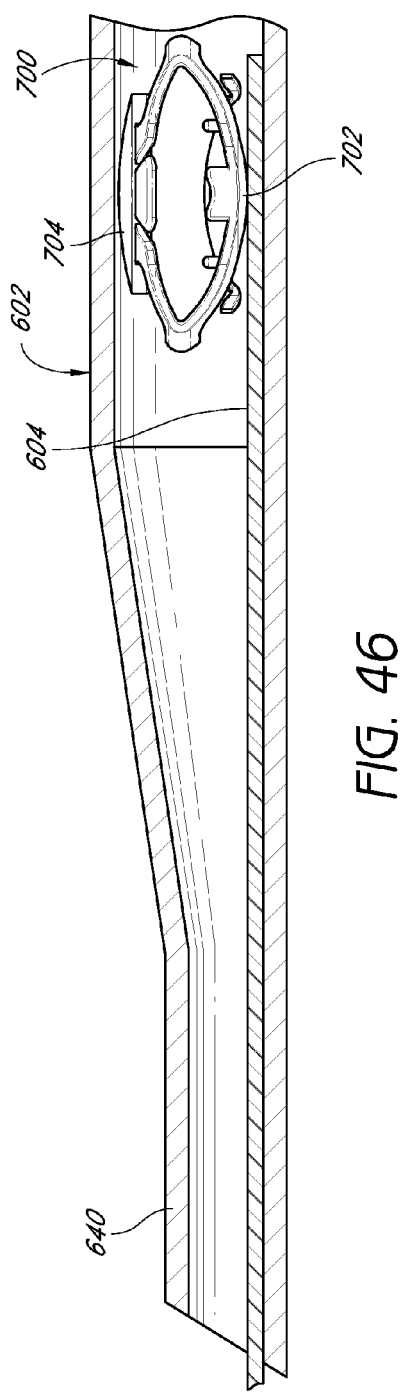
FIG. 46 is a side cross-sectional view of the injector of FIG. 45.
Figure 47:
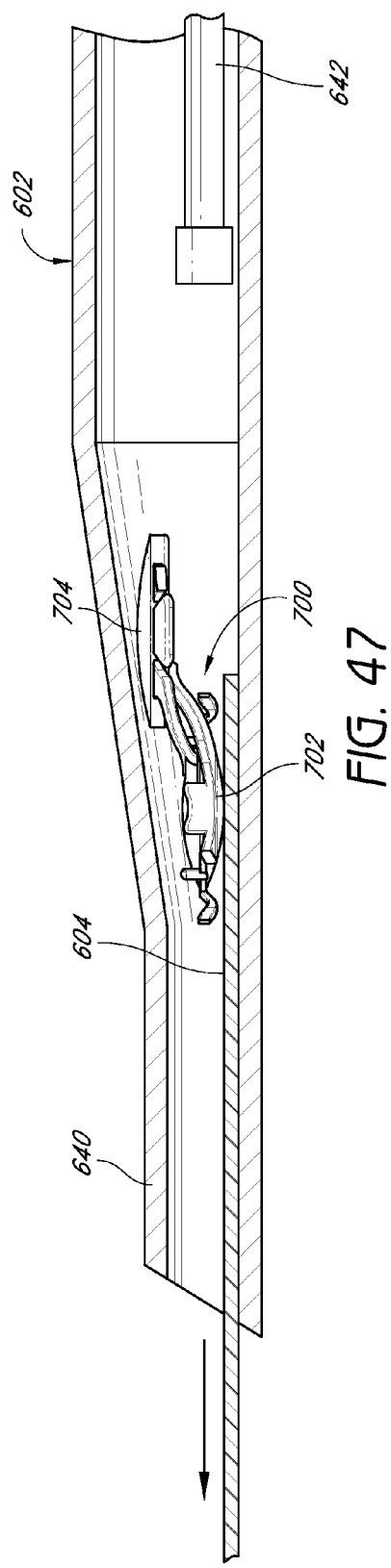
FIG. 47 is another side cross-sectional view of the injector of FIG. 45.

FIGS. 45-47 depict another embodiment of the injector 600, which can be similar to the embodiment of FIGS. 33-44, except as further described and depicted herein. In this embodiment, the actuator/lens carrier 604 may comprise a thin elongate member or strip formed from a suitable polymer film (e.g., PET film). When the IOL 700 is in the storage position (see FIG. 46), the first optic 702 rests on the actuator 604, and the second optic 704 is in contact with the adjacent wall of the housing 602. The actuator 604 is then drawn forward through the tip of the probe 640, and the actuator in turn pulls the IOL 700 forward, causing displacement of the optics into a non-coaxial condition as described above (see FIG. 47). Once the IOL 700 has been drawn between the compacting members 630, 632, the members may be converged by applying pressure to handles 660, 662 formed thereon. (Accordingly, the handles 160, 162 comprise an alternative (or supplement) to the actuator tabs 634, 636 discussed above.) With the lens 200 fully compacted, the plunger 642 may be employed in the usual manner, to push the lens through the injection channel 635 and out the tip of the probe 640.

Accordingly, in the embodiments of FIGS. 33-44 and 45-47, both the lens carrier 604 and the IOL 700 are moved longitudinally, along a continuously longitudinal path, from a first or home position (FIG. 33) in which the lens carrier 604 engages the lens 200 and the optical axes B-B, C-C of the viewing elements or optics 702, 704 are substantially aligned, to a second position (FIG. 35) in which one of the viewing elements/optics is forward of the other and the viewing elements/optics are at least partially compacted. The continuously longitudinal path is, in these embodiments, generally coincident with the longitudinal axis or injection axis A-A. The continuously longitudinal path extends distally from the home position, past the single-element engagement surface 620 located distal of the home position, and between the opposed lens-compacting surfaces of the compacting members 630, 632, which are located distal of the single-element engagement surface 620.

The lens carrier 604 and the IOL 700 are moved further longitudinally, along the continuously longitudinal path, from the second position to a third position in which the (displaced and compacted) IOL 700 is situated within the injector probe 642. From the third position, the IOL 700 is urged longitudinally, along the continuously longitudinal path, out the distal tip of the probe 642.

Figure 48:
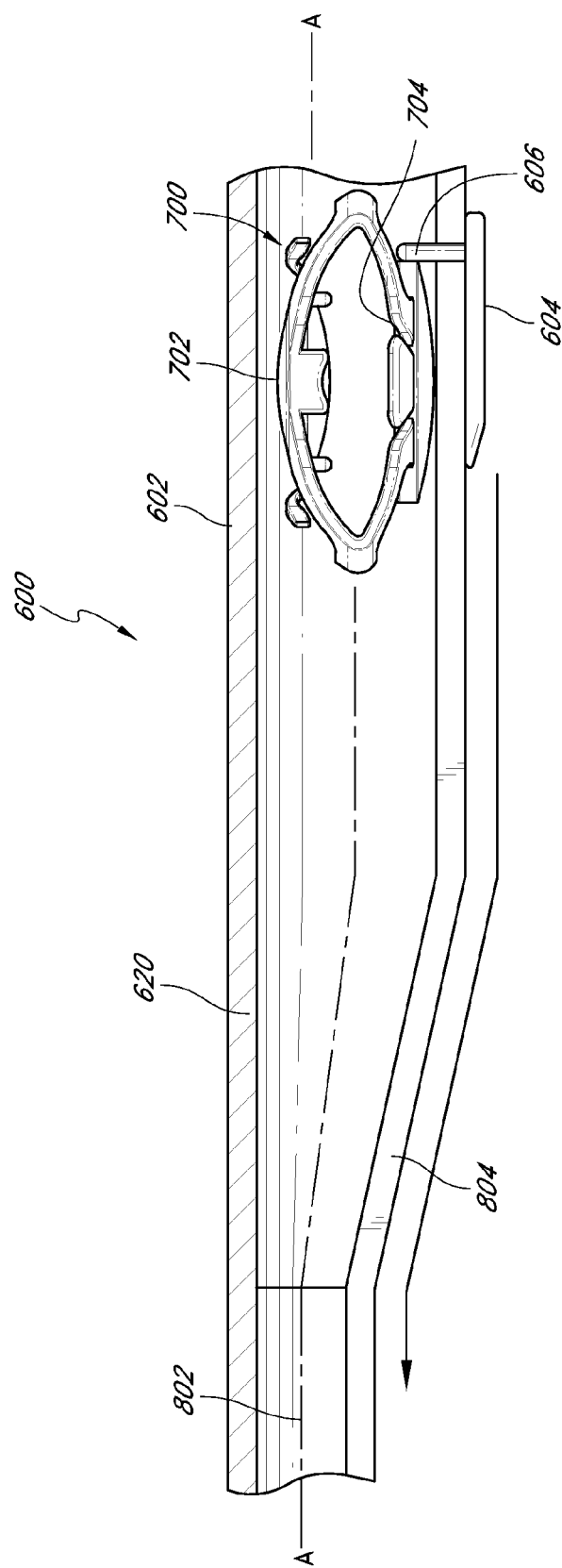
FIG. 48 is a partial side cross-sectional view of another embodiment of the injector.

FIG. 48 depicts another embodiment of the injector 600, which can be similar to the embodiments of FIG. 33-44 or 45-47, except as further described and depicted herein. In the injector 100 of FIG. 48, the lens 200 is configured to move distally, along a continuously longitudinal path in which only a distal portion 802 thereof is substantially coincident with the longitudinal axis/injection axis A-A. Operation of the lens carrier 604 moves the lens distally and along an upslope 804, whereupon the first optic 702 contacts the single-element engagement surface 620. The surface 620 causes the first optic 702 to fall behind the second optic 704, thus displacing the IOL 700 as described and depicted above. Once past the upslope 804, the displaced IOL 700 proceeds distally, substantially along the longitudinal axis A-A, until the IOL 700 reaches the compacting members (not shown in FIG. 48). The compacting and injection process then continues in the manner described and depicted above.

It is contemplated that the IOL 700 may be positioned within (any of the embodiments of) the injector 600 (e.g., with the lens in the storage condition) during manufacture/ assembly of the injector. The injector 600, with the IOL 700 thus disposed inside, may then be sterilized as a unit, either at the point of manufacture or at some downstream location. Where appropriate, the sterilized injector-lens assembly may be contained in a sterile package, wrapper, bag, envelope, etc. in which the injector-lens assembly may remain until arrival at the point (or time) of use. (The injector-lens assembly may be sterilized before and/or after placement in the package, etc.) This facilitates a simple point-of-use procedure for medical personnel involved in implanting the IOL 700 contained in the injector 100: after opening (any) packaging, the physician, or other medical personnel, can compact and insert the IOL 700 using the injector 600 as discussed above, without (any need for) removing the IOL 700 from the injector 600. Accordingly, there is no need to handle the IOL 700 or manually load it into an insertion device at the point of use, both of which can be difficult and tedious, and can compromise the sterility of the lens.

Except as further described herein, any of the embodiments shown in FIGS. 33-48 may be similar to any of the embodiments disclosed in FIGS. 3-32.

In some instances, it can be desirable to provide a tactile feel or tactile feedback to a user of an injector to indicate that an IOL is nearing a distal tip of the injector. This tactile feedback can allow the user to more carefully and controllably advance the IOL through a distal opening of the injector into an eye. In some embodiments, the tactile feedback is provided when the IOL and/or a plunger moving the IOL advances through an area having a higher coefficient of friction. In some embodiments, such an area is located in a distal or terminal region of the injector.

In further instances, it can be desirable to control the direction, orientation, and/or speed at which an IOL is delivered from an injector. In some embodiments, an area having a higher coefficient of friction is provided at the distal end of injector to slow egress of the IOL and thus provide a user with greater control over delivery of the IOL. The higher coefficient of friction can counteract a driving force provided to the IOL by the user of the injector and/or a driving force provided by the IOL itself, such as can arise from the release of stored energy as the IOL transitions from a compressed configuration within the injector to a relaxed configuration outside of the injector. In some embodiments, an expandable member is included at a distal end of the injector to absorb at least a portion of the energy released by the IOL when it transitions from the compressed configuration to the relaxed configuration, thereby slowing egress of the IOL.

FIG. 49 depicts an embodiment of an injector 900 (which may include, but is not limited to, the apparatus 200, the apparatus 400, or the injector 600). In certain embodiments, a frictional force generated during use of the injector 900 provides tactile feedback to a user indicating that an IOL 930 moving within the injector 900 is nearing the position where it will leave the injector 900. In some embodiments, a frictional force slows the egress of the IOL 930 from an opening 917 at a distal end of the injector 900, which can permit relatively controlled delivery of the IOL 930 to an eye.

The injector 900 can include a conduit, conveyance, channel, tube, tubular member, or tubular section 902 that defines a lumen 910 (which may be, but is not limited to, a lumen within the delivery probe 406 or the injector probe 640) having a terminal portion 912 at a distal end 916 and a proximal portion 914 located proximal to, and juxtaposed with, the terminal portion 912. The distal end 916 of the lumen 910 can define the opening 917 through which an IOL 930 can pass to be delivered within an eye. The lumen 910 can further include an inner surface 918. The tubular section 902 can comprise an outer surface 919.

In some embodiments, the injector 900 further includes an injector plunger 920 (which may include, but is not limited to, the driving member 290, the driving member 490, or the plunger 642) that is at least partially disposed within the lumen 910. The injector plunger 920 can impart a driving force on the IOL 930 which moves the IOL 930 within the lumen 910. The IOL 930 may be a single-, dual-, or multiple-optic intraocular lens, including, but not limited to, the IOL 100, the multiple-lens IOL 120, and the IOL 700, referenced above. During injection, the injector plunger 920 is moved towards the distal end 916 of the lumen 910, which in turn causes the IOL 930 to move towards the distal end or distal tip 916. Along its journey through the lumen 910, the IOL 930 moves through the proximal portion 914 of the lumen 910 before passing through the terminal portion 912.

In some embodiments, the IOL 930 is conveyed along the tubular section 902 in a compacted condition. Any suitable orientation of the IOL 930 in the tubular section 902 could be provided. In some embodiments, the IOL 930 comprises two or more optics, and can be advanced through the tubular section 902 with one optic in front of another optic. For example, in some embodiments, a first viewing element (such as the viewing element 702) is in front of a second viewing element (such as the viewing element 704) as the IOL 930 is advanced through the tubular section 902, and in other embodiments, the second viewing element is in front of the first viewing element. In some embodiments, the IOL 930 is more compacted in at least one phase of injection, e.g., within the tubular section 902, than is shown in the illustrated embodiments. For example, one or more optics may be folded or rolled, as described above. This further compaction of the optic(s) can enable insertion through a smaller incision.

With reference to FIGS. 49 and 50, the movement of the IOL 930 through the lumen 910 creates a lens coefficient of friction 940 between the inner surface 918 and the abutting surface of the IOL 930, the lens coefficient of friction being associated with a lens frictional force 942 that acts on the IOL 930 and that resists the driving force 944 imparted on the IOL 930 by the injector plunger 920. The higher the coefficient of sliding friction, $\mu$, between the two surfaces, the greater the frictional force, F, associated with one surface sliding past the other. Quantitatively, $F=\mu N$, where N is the strength of the force (perpendicular to the interface between the surfaces) that holds the two surfaces together. In certain embodiments, the lens frictional force 942 has a smaller value when at least a portion of the IOL 930 abuts the inner surface 918 at a first location, $L_1$, located within the proximal portion 914 of the lumen 910, than when at least a portion of the IOL 930 abuts the inner surface 918 at a second location, $L_2$, located within the terminal portion 912.

In certain embodiments, due to the increase in frictional force experienced by the IOL 930 between the first location $L_1$ and the second location $L_2$ of the lumen 910, the user of the injector 900 is provided with tactile feedback indicating that the IOL 930 is nearing ejection from the distal end 916 of the lumen 910. In further embodiments, the greater frictional force acting on the IOL 930 substantially prevents the IOL 930 from springing from the distal tip 916. The greater frictional force acting on the IOL 930 within the terminal portion 912 can thus provide the user with greater control over the IOL 930 during ejection. Accordingly, in some embodiments, the terminal portion 912 may also be referred to as a release control section.

In certain embodiments, the release control section is sized to fit within the anterior chamber of an eye when the injector 900 is positioned in the eye to inject the IOL 930 into the anterior chamber. Accordingly, in some embodiments, the release control section 912 resists passage of the IOL 930 through the portion of the injector 900 that is located within the anterior chamber.

In some embodiments, the lens frictional force 942 provided by the release control section 912 resists a restorative force of the IOL 930. For example, as described above, the IOL 930 can be deformed, compacted, or compressed to a relatively small configuration as the IOL 930 is prepared for insertion into an eye via the injector 900. As the IOL 930 emerges from the distal end 916 of the injector 900, at least a portion of the IOL 930 can expand to a natural, decompressed, or relaxed state, thereby releasing stored mechanical energy. In some instances, this release of stored energy imparts a driving force to the remainder of the IOL 930 that is located within the injector 900. In some embodiments, the driving or restorative force due to expansion of the IOL 930, or the release of mechanical energy stored in the compacted IOL 930, can be inhibited, slowed or counteracted by the lens frictional force 942.

In some embodiments, once the injector plunger 920 is advanced distally within the lumen 910 sufficiently far to cause a portion of the IOL 930 to emerge from the lumen 910, the resulting driving force due to release of stored energy is sufficient to cause the IOL 930 to emerge from the lumen 910 without further urging from the plunger 920. For example, in some embodiments, the plunger 920 is advanced to the point where the restorative force of the IOL 930 is sufficient to move the IOL 930 from the lumen 910, but is advanced no further than this point, thus permitting the IOL 930 to egress from the lumen 910 of its own accord. In certain of such embodiments, the lens frictional force 942 may thus counteract only the driving force supplied by the IOL 930 itself as it emerges from the lumen 910, thereby slowing egress of the IOL 930.

In other embodiments, the plunger 920 can be advanced beyond a point where a restorative force arises as the IOL 930 egresses the lumen, and thus can help urge the IOL 930 out of the lumen 910. Accordingly, in some embodiments, the lens frictional force 942 resists both the driving force 944 imparted by the plunger 920 and the driving force imparted by the release of stored energy from the IOL 930.

In certain embodiments, such as when the IOL 930 includes two or more optics, the IOL 930 can store more energy and at least for this reason can be more complicated to inject in a controlled manner than can some single-optic systems. For example, in some embodiments, the IOL 930 includes a first and a second viewing element (such as, for example, the viewing elements 702, 704), and further includes two or more biasing members (such as, for example, the biasing members 126, 128) connecting the viewing elements. Accordingly, the dual-optic IOL 930 can have greater mass than certain single-optic varieties, and further, can include separate masses capable of independent movement relative to one other that are joined by spring-like members. Providing controlled egress of such an IOL 930 can be particularly important in the environment of the delicate structures of the eye.

Certain embodiments described herein can advantageously retard egress of the optics of a dual-optic IOL 930 such that the plunger 920 is used to urge both the first and the second optics from the lumen. In some embodiments, the release control section 912 is capable of retaining a second optic (such as the element 704) stationary after a first optic (such as the element 702) has exited the lumen 910. In certain embodiments, the release control section 912 is configured to retain the second optic substantially stationary relative to the injector 900, even after a substantial portion of the second optic has exited the lumen 910. For example, the substantial portion of the second optic can be between about ⅕ and about ½, between about ¼ and about ½, or between about ⅓ and about ½ of the optic. In some embodiments, the portion is no less than about ¼, no less than about ⅓, no less than about ½, or no less than about ⅔ of the optic. Permitting a large portion of the IOL 930 to egress the lumen while maintaining at least a portion of a second optic of the IOL 930 relatively stationary in this manner can provide an operator of the injector 900 with excellent control over the delivery and placement of the IOL 930.

Figure 51C:
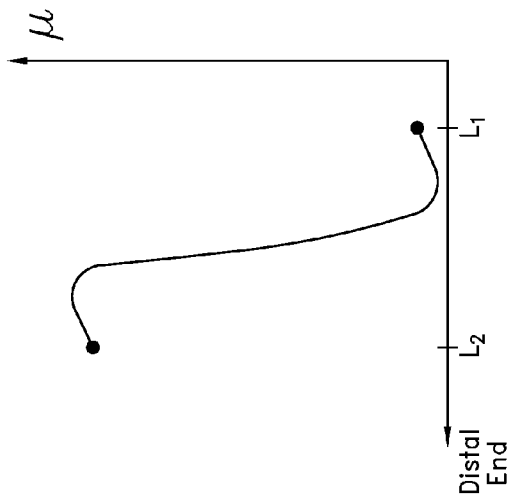
FIGS. 51A, 51B, and 51C display three profiles representing separate manners in which a coefficient of friction can vary with distance between a first location and a second location within an injector.
Figure 51B:
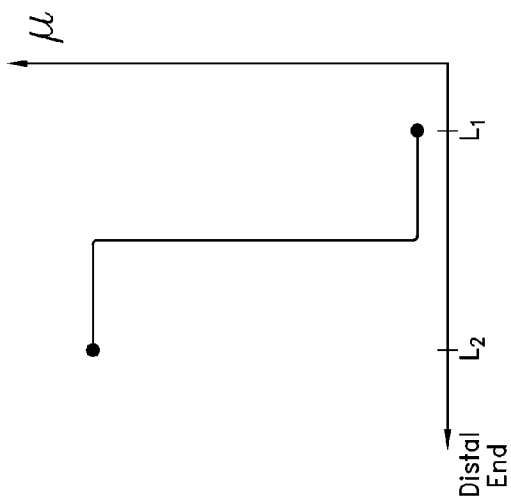
Figure 51A:
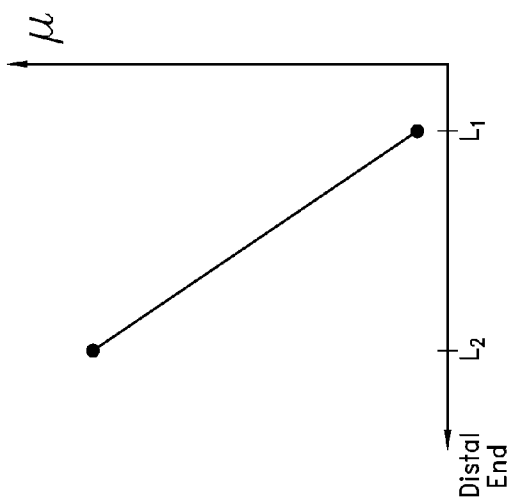

Contact between the IOL 930 and the inner surface 918 of the lumen 910 can create a lens coefficient of friction 940 that varies as the IOL 930 moves through the lumen 910. FIGS. 51A, 51B, and 51C display three profiles illustrating possible manners in which the lens coefficient of friction 940 can be varied in the injector 900. In some embodiments, the frictional force 942 acting on the IOL 930 between the locations $L_1$ and $L_2$ also follows the profiles shown in FIGS. 51A-C.

In FIG. 51A, the lens coefficient of friction 940 acting on the IOL 930 increases in a substantially linear fashion as the IOL 930 moves from the location $L_1$ to the location $L_2$. In some embodiments, the increase in the coefficient of friction 940 is relatively gradual, moderate, regular, or steady. For example, in some embodiments, the slope of the line depicted in FIG. 51A can be relatively small. In other embodiments, the increase in the coefficient of friction 940 is relatively strong or pronounced. For example, in some embodiments, the slope of the line depicted in FIG. 51A can be relatively large.

In FIG. 51B, the lens coefficient of friction 940 is relatively constant between the location $L_1$ and a transition point between the locations $L_1$ and $L_2$ at which the coefficient of friction 940 increases abruptly or suddenly. The coefficient of friction 940 is at a substantially constant, higher value between the transition point and the location $L_2$.

In FIG. 51C, the lens coefficient of friction 940 varies in a non-linear fashion between the locations $L_1$ and $L_2$ such that the coefficient is higher at the location $L_2$ than at the location $L_1$. In each of the foregoing embodiments, the lens coefficient of friction 940 and the corresponding frictional force 942 acting on the IOL 930 each increases as the IOL 930 approaches the distal end 916 of the lumen 910. Other profiles of the lens coefficient of friction 940 and the corresponding frictional force 942 acting on the IOL 930 between the locations $L_1$ and $L_2$ are also possible.

In certain embodiments, the inner surface 918 of the lumen 910 creates a lens coefficient of friction 940 with the IOL 930 that causes the lens frictional force 942 to increase as the IOL 930 egresses the lumen 910. For example, the lens coefficient of friction 940 can increase within the terminal portion 912 such that the associated lens frictional force 942 increases as the IOL 930 egresses the lumen 910. Any suitable technique may be used to control the lens coefficient of friction 940 between the IOL 930 and the inner surface 918.

Figure 52:
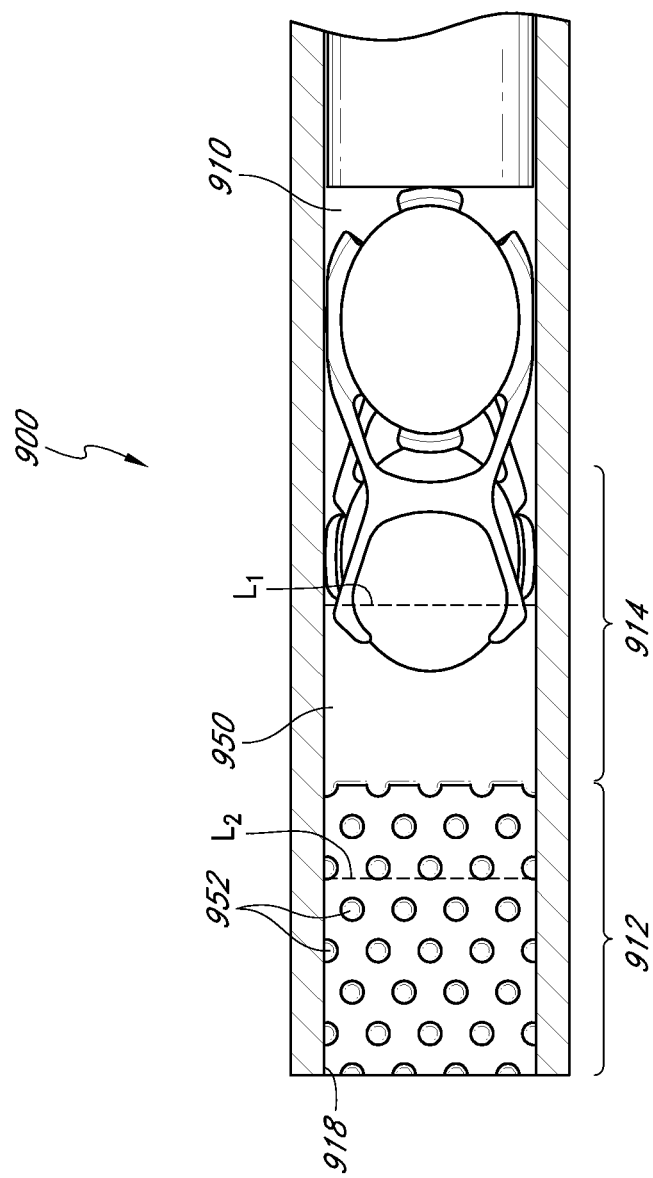
FIG. 52 is a schematic partial top cross-sectional view of an embodiment of an injector having a partially coated inner surface.

With reference to FIG. 52, in some embodiments, the lens coefficient of friction 940 is caused at least in part by one or more coatings 950 selectively covering the inner surface 918 of the lumen 910. In some embodiments, a low-friction coating 950 substantially covers the entire inner surface 918 of the proximal portion 914 of the lumen 910. In some embodiments, a low friction coating 950 covers only a portion of the inner surface 918 of the terminal portion 912 of the lumen 910. The combination of coated and uncoated regions of the inner surface 918 of the terminal portion 912 can provide a higher coefficient of friction at the second location $L_2$ as compared with the first location $L_1$.

In certain embodiments, when the proximal portion 914 is substantially entirely covered with the low-friction coating 950 and the terminal portion 912 is only partially coated with the coating 950, the terminal portion 912 can substantially retard egress of the IOL 930 from the injector 900. Advantageously, in some embodiments, presence of the low-friction coating 950 at the terminal portion 912 provides sufficient lubricity to deliver the IOL 930 substantially without causing harm to the IOL 930. Retarding egress of the IOL 930 in this manner thus can permit more controlled injection of the IOL 930 without scratching or marring the IOL 930, without leaving a film or residue on the IOL 930, and/or without otherwise detrimentally affecting operation of the IOL 930.

The low-friction coating 950 can be of any suitable variety. In some embodiments, the coating 950 is adhered to, deposited on, or otherwise applied to the inner surface 918. In other embodiments, the coating 950 is integrally formed with the material that defines the lumen 910. The coating 950 is preferably configured to not scratch, mar, or otherwise damage the IOL 930. In some embodiments, the coating 950 is hydrophilic. In various embodiments, the coating may comprise hydrophilic materials that are either directly or indirectly adhered, bonded, mechanically locked or otherwise attached to or coupled with the material that forms the inner lumen 910. The hydrophilic material may be a two part polymeric coating comprising a supporting polymer and a hydrophilic polymer. The supporting polymer may be cross-linked polyacrylate that may be attached to the inner surface 918 of the lumen 910.

As indicated above, the inner surface 918 can include partially coated surfaces that include alternating zones of coated surface and uncoated surface, or that define an arrangement of coated portions separated by uncoated portions. In the illustrated embodiment, the coating 950 defines a series of rounded or circular segments 952 that are separated by an uncoated portion of the inner surface 918 of the terminal portion 912 of the lumen 910. The segments 952 can define shapes or configurations other than circles, such as, for example, polygons or substantially irregular shapes. In some embodiments, one or more of the segments 952 are sized differently from other segments 952.

The coated and uncoated surfaces can form a variety of other arrangements or patterns. For example, in some embodiments, at least one of the partially coated surfaces includes a checkerboard or crosshatch pattern of coated surface and uncoated surface. Some patterns or arrangements can be regular or repeated, and others can be substantially irregular. For example, in some embodiments, the arrangement of coated and uncoated surfaces substantially defines a spray pattern or a zigzag pattern, and in other embodiments, the coated and uncoated surfaces are arranged randomly, irregularly, or without a repeated pattern. The size and configuration of a pattern can be optimized to provide a desired amount of slowing to the egress of the IOL 930.

In some embodiments, the partially coated surface extends from a distal edge of the lumen 910 to a position within the lumen only a relatively short distance from the distal edge of the lumen 910. In various embodiments, the distance is between about 1.0 centimeters and about 5.0 centimeters, between about 0.5 centimeters and about 4.0 centimeters, between about 0.1 centimeters and about 3.0 centimeters, or between about 0.1 and about 1.0 centimeter. In some embodiments, the distance is no more than about: 0.1 centimeters, 0.25 centimeters, 0.5 centimeters or 1.0 centimeters. As with other properties of the partially coated surface, the distance from the distal edge of the lumen 910 to which the partially coated surface extends can be optimized to provide a desired amount of slowing to the IOL 930.

In some embodiments, the inner surface 918 includes a low-friction coating surface at the first location, $L_1$, and an uncoated surface at the second location, $L_2$. In other embodiments, the inner surface 918 includes a high-friction coating surface at the second location, $L_2$, and an uncoated surface at the first location, $L_1$. In still other embodiments, the inner surface 918 includes a low-friction coating surface at the first location, $L_1$, and a high-friction coating surface at the second location, $L_2$. In some embodiments, the inner surface includes a partially coated surface at one or both of the first and second locations, $L_1$, $L_2$. In some embodiments, the second location $L_2$ (whether coated or uncoated) is roughened such that the coefficient of friction at the second location $L_2$ is greater than the coefficient of friction at the first location $L_1$.

In some embodiments, the inner surface 918 has a greater proportion of its area coated with a low-friction coating at the first location $L_1$ than at the second location $L_2$. In certain of such embodiments, the inner surface 918 can be completely coated or partially coated with the low-friction coating at the first location $L_1$, and/or the inner surface 918 can be partially coated with the low-friction coating or uncoated at the second location $L_2$.

Figure 53:
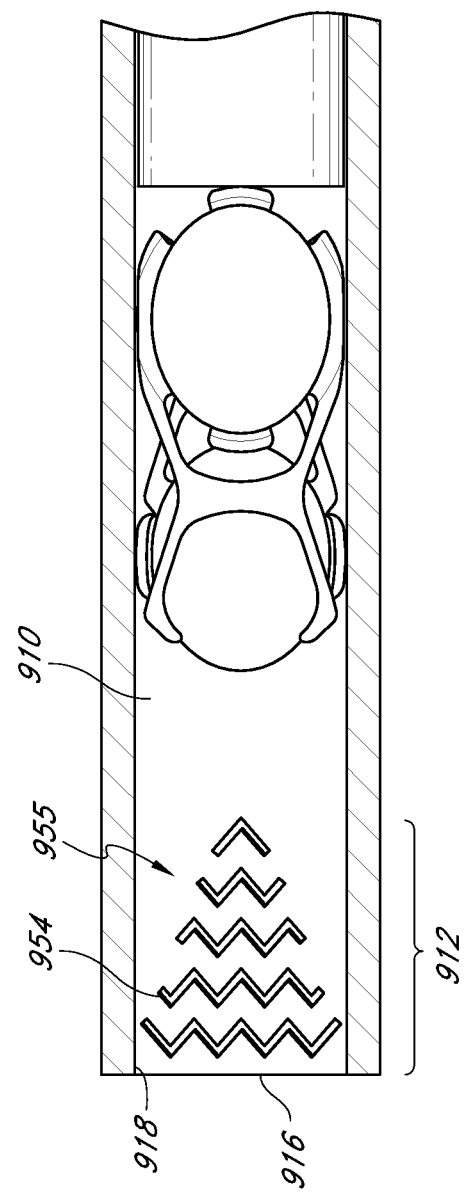
FIG. 53 is a schematic partial top cross-sectional view of an embodiment of an injector having grooves at a terminal portion thereof.

With reference to FIG. 53, in certain embodiments, the lens coefficient of friction 940 is provided at least in part by one or more channels, indentations, depressions, or grooves 954 in the inner surface 918 of the terminal portion 912 of the lumen 910. The grooves 954 can be formed in any suitable manner, such as by molding, milling, or etching. In some embodiments, the grooves 954 are laser etched into the inner surface 918. In various embodiments, one or more of the grooves 954 has a depth, as measured in a direction substantially orthogonal to a straight surface line along a longitudinal length of the inner surface 918, of no more than about 0.0005 inch to about 0.003 inch. In other embodiments, the depth, as measured in a direction substantially orthogonal to a straight surface line along a longitudinal length of the inner surface 918, of about 0.0005 inch to about 0.002 inch. In some embodiments, one or more of the grooves 954 has a width, or a minimal separation distance of opposite sides of a groove 954, of no more than about 0.001 inch to about 0.100 inch or more preferably from about 0.001 inch to about 0.050 inch. Values outside of the listed ranges are also possible.

In the illustrated embodiment, the grooves 954 are substantially zigzagged. Zigzag grooves also can be substantially parallel to each other. The length of the grooves 954 increases toward the distal tip 916 of the lumen 910, thus the grooves 954 generally define a triangular grooved region 955 in one embodiment. The coefficient of friction can increase from a proximal tip of the grooved region 955 to a distal base of the grooved region 955, thus resulting in a coefficient of friction profile, such as that illustrated in FIG. 51A. This figure illustrates that in some embodiments, at least a portion of the coefficient of friction profile can increase linearly. Other arrangements are possible for grooves 954 and/or the grooved region 955. For example, in some embodiments, the grooved region 955 defines a generally parabolic, generally semicircular, or generally polygonal (e.g., square or rectangular) perimeter.

FIG. 54 illustrates another embodiment of the injector 900. The injector 900 can define an angled tip 956 that includes a grooved region 955. In some advantageous embodiments, the angled tip 956 provides for a relatively controlled egress of the IOL 930 from the distal end 916 of the lumen 910. For example, in some embodiments, a portion of the IOL 930 expands from an open region 957 substantially opposite the grooved region 955. As a portion of the IOL 930 expands through the open region 957, energy is released that tends to move the IOL 930 distally from the lumen 910. However, in some embodiments, a portion of the IOL 930 opposite the expanding portion is in contact with the grooved region 955, which can have a relatively large coefficient of friction and thus tend to slow and/or control egress of the IOL 930.

In some embodiments, the angled tip 956 can more easily or more effectively be laser etched than certain flat-tipped embodiments. For example, the open region 957 can provide an optical path that is unobstructed by the lumen 910 and, in further instances, that is substantially orthogonal to the inner surface 918.

With reference to FIGS. 54B-54D, the grooves 954 within the grooved region 955 can define a variety of patterns. As shown in FIG. 54B, in some embodiments, at least some of the grooves 954 are substantially semicircular. As shown in FIG. 54C at least some of the grooves 954 can be substantially rectangular, and can be elongated in a direction substantially parallel to a longitudinal length of the lumen 910. Though illustrated as substantially rectangular, the groves can have varying lengths providing a generally triangular or distally expanding area. As shown in FIG. 54D, at least some of the grooves 954 can be elongated in a direction substantially perpendicular to a longitudinal length of the lumen 910. Other arrangements of the grooves 954 and the grooved region 955 are also possible. For example, the grooves 954 can be substantially ovoid and/or can have rounded edges. The grooved region 955 can define a shape other than substantially triangular, and can extend over a larger or smaller portion of the inner surface 918 than that shown in FIGS. 54B-54D.

In some embodiments, the inner surface 918 of the lumen 910 includes raised portions or protrusions (not shown) in addition to or instead of the grooves 954. In some embodiments, the raised protrusions are relative to each other, sized, and/or shaped in the same manner as the grooves 954 illustrated in any of FIGS. 53 and 54A-D. For example, in some embodiments, the protrusions have a height, as measured from the inner surface 918, that is within the ranges described above with respect to the grooves 954. The protrusions can be arranged in any of the manners described with respect to the grooves 954.

FIG. 55 depicts another embodiment of the injector 900 in which a frictional force can be used to provide tactile feedback to a user to indicate that an intraocular lens moving within the injector is nearing the position where it will leave the injector. The injector 900 includes a lumen 960 having a terminal portion 962 at a distal end 966 and a proximal portion 964 located proximal to, and juxtaposed with, the terminal portion 962. The lumen 960 further includes an inner surface 968.

In certain embodiments, the injector 900 further includes an injector plunger 970 at least partially disposed within the lumen 960. The injector plunger 970 includes an abutting surface 972 in facing arrangement to, and in at least temporary contact with, the inner surface 968 of the lumen 960. The injector plunger 970 imparts a driving force on the IOL 980 which moves it within the lumen 960. The IOL 980 may be a single-, dual-, or multiple-optic intraocular lens, including, but not limited to, the IOL 100, the multiple-lens IOL 120, and the IOL 700, referenced above. During injection, the injector plunger 970 is moved towards the distal end 966 of the lumen 960, which in turn causes the IOL 980 to move towards the distal end 966. Along its journey through the lumen 960, the IOL 980 moves through the proximal portion 964 of the lumen 960 before passing through the terminal portion 962. In some embodiments, the abutting surface 972 of the plunger 970 is relatively closer to the distal end of the plunger 970 than is schematically depicted in FIG. 55. This variation would permit the abutting surface 972 to traverse more than one region of the lumen 960 where increased friction results. This could provide an advantage of more than one discrete area of tactile feedback, e.g., distal of $L_1'$ and distal of $L_1$.

With reference to FIGS. 55 and 56, the movement of the IOL 980 through the lumen 960 creates a plunger coefficient of friction 990 between the inner surface 968 and the abutting surface 972 of the injector plunger 970, the plunger coefficient of friction being associated with a plunger frictional force 992 that acts on the injector plunger 970 and that resists the driving force 994 imparted on the plunger 970 by the user. As discussed above, the higher the coefficient of sliding friction between the two surfaces, $\mu$, the greater the frictional force, F, associated with one surface sliding past the other. In the embodiment of FIG. 52, the plunger frictional force 942 (created by the frictional sliding of the abutting surface 972 against the inner surface 968 of the lumen 960) has a smaller value when the IOL 980 is at a first location, $L_1$, located within the proximal portion 964 of the lumen 960, than when the IOL 980 is at a second location, $L_2$, located within the terminal portion 962.

Because of this increase in frictional force experienced by the IOL 980, the user of the injector 900 is provided with tactile feedback that the IOL 980 is nearing ejection from the distal end 966 of the lumen 960. The greater frictional force acting on the injector plunger 970 within the terminal portion 962 also can provide the user with greater control over the IOL 980 during ejection.

Contact between the abutting surface 972 of the injector plunger 970 and the inner surface 968 of the lumen 960 create a plunger coefficient of friction 990 that varies as the IOL 980 moves through the lumen 960. The profiles displayed in FIGS. 51A, 51B, and 51C also illustrate three possible manners in which the plunger coefficient of friction may be varied for the injector 900. Accordingly, the foregoing discussion of FIGS. 51A-C with respect to the lens coefficient of friction 940 is applicable to the plunger coefficient of friction 990 and corresponding frictional force 992 acting on the plunger 970.

For example, similar to the friction profile illustrated in FIG. 51A, the plunger coefficient of friction 990 acting between the abutting surface 972 and the inner surface 968 can increase in a substantially linear fashion as the IOL 930 moves from the location $L_1$ to the location $L_2$ (i.e., as the abutting surface 972 of the plunger 970 moves from the location $L_1'$ to the location $L_2'$). Similar to the friction profile illustrated in FIG. 51B, the plunger coefficient of friction 990 can be relatively constant between the location $L_1'$ and a transition point between the locations $L_1'$ and $L_2'$ at which the coefficient abruptly increases. The coefficient of friction 990 can be at a substantially constant, higher value between the transition point and the location $L_2'$. Similar to the friction profile illustrated in FIG. 51C, the plunger coefficient of friction 990 can vary in a non-linear fashion between the locations $L_1'$ and $L_2'$, such that the coefficient is higher at the location $L_2'$ than at the location $L_1'$. In each of these embodiments, the plunger coefficient of friction 990 and the corresponding frictional force 992 acting on the plunger 970 each increases as the IOL 980 approaches the distal end 966 of the lumen 960. Other profiles of the plunger coefficient of friction 990 and the corresponding frictional force 992 acting on the plunger 970 between the locations $L_1'$ and $L_2'$ are also possible.

In another embodiment, the inner surface 968 of the lumen 960 creates a plunger coefficient of friction 990 with the plunger 970 that causes the plunger frictional force 992 to increase as the IOL 980 egresses the lumen 960. In this embodiment, the plunger coefficient of friction 990 increases as the plunger 970 pushes the IOL 980 within the terminal portion 962 of the lumen 960, such that the plunger coefficient of friction 990 and the corresponding plunger frictional force 992 increase as the IOL 980 egresses the lumen 960.

Any suitable technique may be used to control the plunger coefficient of friction 990 between the abutting surface 972 and the inner surface 968. For example, one or more of the abutting surface 972 and the inner surface 968 can be coated or partially coated in any suitable manner (such as any manner described above with respect to the distal portion 912 and the proximal portion 914), can include grooves or channels (such as the grooves 954), can include protrusions, or can be roughened.

In some embodiments, the plunger coefficient of friction 990 is caused at least in part by one or more coatings selectively covering the inner surface 968 of the lumen 960. In one embodiment, the inner surface 968 includes a low-friction coating surface at a first location, $L_1'$, and an uncoated surface at the second location, $L_2'$ (see FIG. 55). In this embodiment, the locations $L_1'$ and $L_2'$ correspond to the locations of the abutting surface 972 when the IOL 980 is at the locations $L_1$ and $L_2$, respectively. In another embodiment, the inner surface 968 includes a high-friction coating surface at the second location, $L_2'$, and an uncoated surface at the first location, $L_1'$. In another embodiment, the inner surface 968 includes a low-friction coating surface at the first location, $L_1'$, and a high-friction coating surface at the second location, $L_2'$. In other embodiments, the inner surface includes a partially coated surface at one or both of the first and second locations, $L_1'$, $L_2'$. In some embodiments, the inner surface 968 includes partially coated surfaces that include alternating zones of coated surface and uncoated surface. In some embodiments, at least one of the partially coated surfaces includes a checkerboard pattern of coated surface and uncoated surface.

In some embodiments, the inner surface 968 has a greater proportion of its area coated with a low-friction coating at the first location $L_1'$ than at the second location $L_2'$. In certain such embodiments, the inner surface 968 can be completely coated or partially coated with the low-friction coating at the first location $L_1'$, and/or the inner surface 968 can be partially coated with the low-friction coating or uncoated at the second location $L_2'$.

Referring to FIG. 49, in some embodiments, a low-friction portion 951 is provided on the outer surface 919 of the injector 900. The low-friction portion 951 can be of a coating any suitable variety. In some embodiments, the low-friction portion 951 is adhered to, deposited on, or otherwise applied to the outer surface 919. In other embodiments, the low-friction portion 951 is integrally formed with the material that forms the tubular section 902. The low-friction portion 951 is preferably configured to provide a coefficient of friction between the surface 919 and eye tissue that is lower than a coefficient of friction that would otherwise exist between a tubular section of a conventional injector and the eye tissue. In some embodiments, the low-friction portion 951 is hydrophilic coating. In various embodiments, a coating may be provided that comprises hydrophilic materials that are either directly or indirectly adhered, bonded, mechanically locked or otherwise attached to or coupled with the material that forms the tubular section 902. The hydrophilic material may be a two part polymeric coating comprising a supporting polymer and a hydrophilic polymer. The supporting polymer may be cross-linked polyacrylate that may be attached to the outer surface 919 of the tubular section 902. If a coating 950 is applied to an inner surface of the lumen 910, then coating or other low-friction portion 951 applied to the outer surface 919 can comprise the same or similar materials as the coating 950, or may comprise a different material or combination of materials than the coating 950.

The low-friction portion 951 on the outer surface 919 may facilitate introduction of the tubular section 902 into an anterior chamber of an eye by reducing the coefficient of friction that would otherwise exist between a material conventionally used and the eye tissue, such as the capsular bag. This reduction in friction may allow a physician to apply a lower insertion force when inserting the tubular section 902 through an incision in an eye. Additionally or alternatively, the reduction in friction may allow insertion of the IOL through a smaller incision in the eye and/or inhibit stretching of the incision by the tubular section 902. These advantages may be particularly beneficial to insertion devices for dual-optic IOLs because some such devices employ insertion lumens that are larger than the insertion lumens employed by some insertion devices for single-optic IOLs. Accordingly, the low-friction portion 951 can provide the advantage of reducing trauma to the eye in a number of ways during a procedure to implant an IOL.

Figure 57:
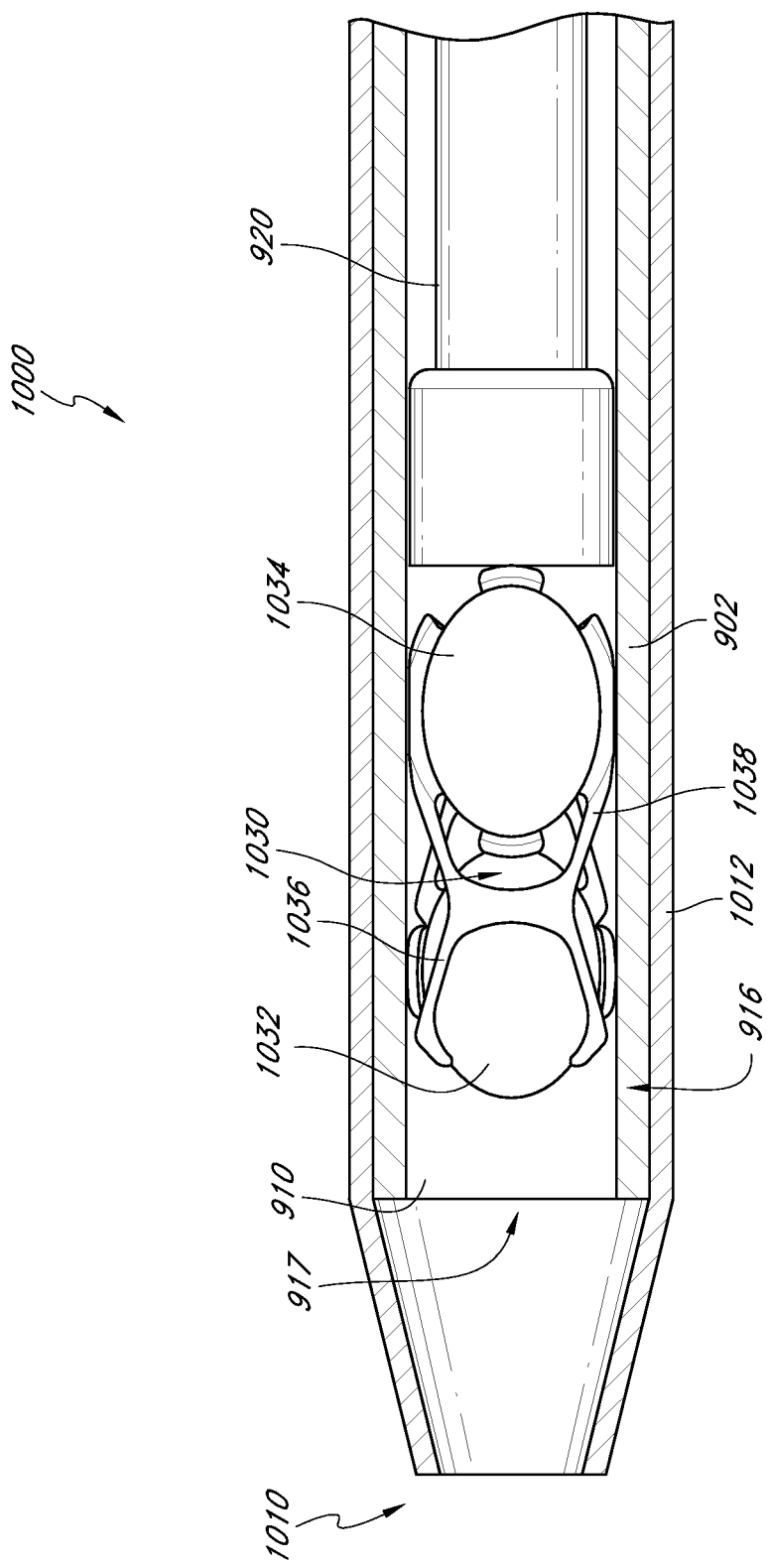
FIG. 57 is a schematic partial top cross-sectional view of another embodiment of an injector.

FIG. 57 illustrates an embodiment of an injector 1000. The injector 1000 can resemble the injector 900 in many respects. Accordingly, like features are identified with like numerals. The injector 1000 can differ in other respects, such as those described hereafter.

In certain embodiments, the injector 1000 includes a generally tubular section 902 that defines a lumen 910. The lumen 910 can define an opening 917 at a distal end 916 thereof. In some embodiments, at least a portion of a plunger 920 is disposed within the lumen 910. In some embodiments, the injector 1000 further includes an expansion member 1010. The expansion member 1010 can take any suitable form permitting controlled expansion of a lens passing therethrough. For example, in various embodiments, the expansion member 1010 can be a sleeve (e.g., an elastomeric sleeve), membrane, energy absorption tip, or release control section. In many embodiments, the expansion member 1010 is at the distal end 916 of the lumen.

In certain embodiments, the expansion member 1010 comprises a flexible, supple, pliable, elastic, and/or expandable material. In some embodiments, the expansion member 1010 comprises a resilient material capable of expanding from a relaxed, contracted, or constricted state to a stretched, enlarged, or expanded state and returning again to the constricted state. For example, in various embodiments, the expansion member 1010 comprises silicone rubber, polyethylene, Pebax®, or other polyolephins.

The expansion member 1010 can be coupled with the tubular section 902 in any suitable manner. For example, in various embodiments, the expansion member 1010 is bonded to, stretch fit about, or integrally formed with the tubular section 902. In some embodiments, the expansion member 1010 comprises heat shrink tubing 1012 and/or can be heat shrink bonded to the tubular section 902.

In some embodiments, the expansion member 1010 extends a relatively small longitudinal distance beyond a distal tip of the tubular section 902. For example, in various embodiments, the longitudinal distance is between about 0.001 inch and about 0.020 inch, and more preferably from about 0.001 inch to about 0.010 inch. In some embodiments, substantially the entire expansion member 1010 is sized to fit within the anterior chamber of an eye when the injector 1000 delivers an IOL 1030 to the eye.

The IOL 1030 can comprise any suitable IOL, such as the IOL 930 described above. Accordingly, the IOL 1030 can comprise a single-, dual-, or multi-optic lens. In the illustrated embodiment, the IOL 1030 comprises a dual-optic system. The IOL 1030 includes a first optic 1032 and a second optic 1034 that are coupled with each other via a first biasing member 1036 and a second biasing member 1038. Other arrangements are also possible. In the embodiment illustrated in FIG. 57, the entire IOL 1030 is within the lumen 910, and the expansion member 1010 is in the constricted state.

Figure 58:
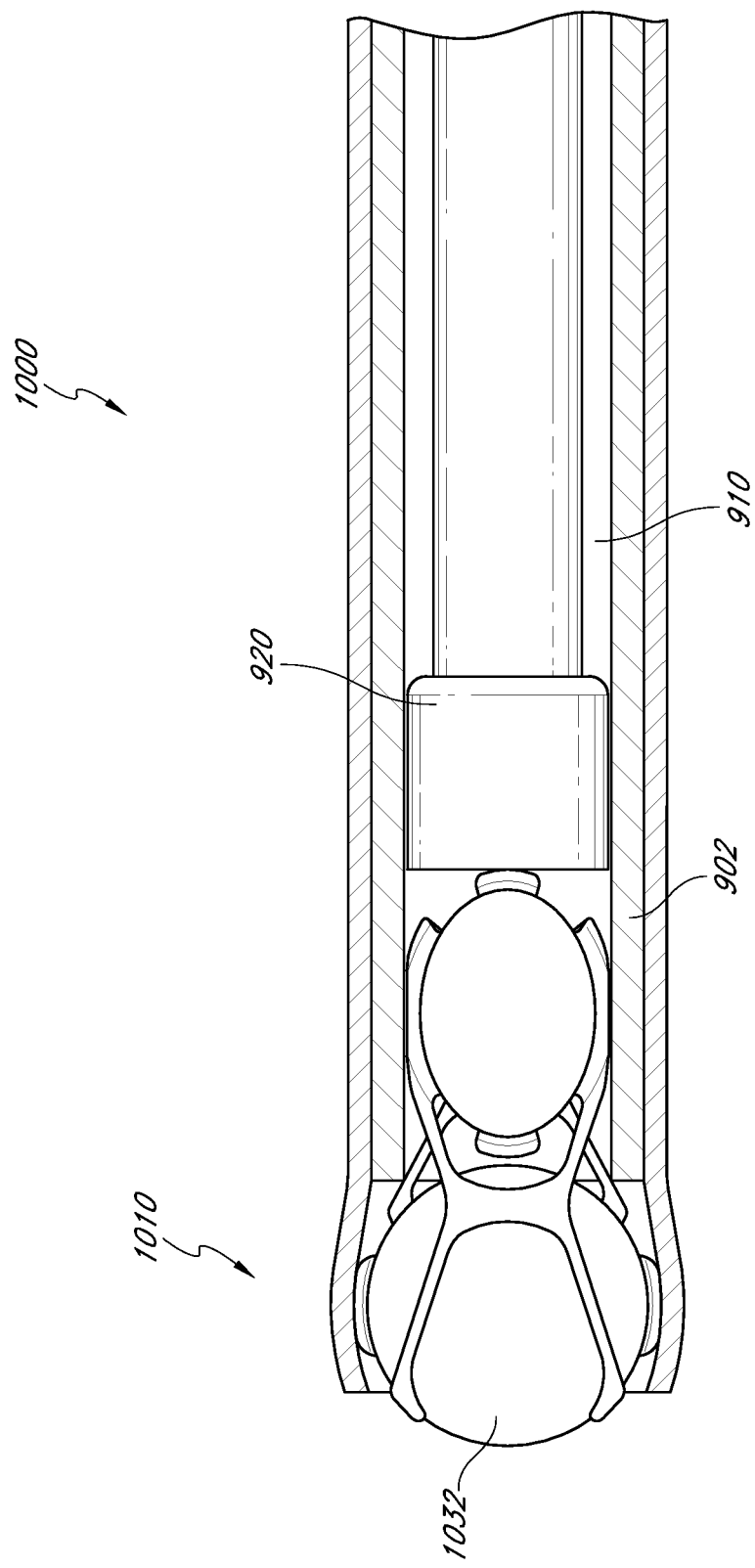
FIG. 58 is a schematic partial top cross-sectional view of the injector of FIG. 57 showing an expansion member in an expanded state and retaining a first optic of an embodiment of an intraocular lens.

With reference to FIG. 58, in certain embodiments, the expansion member 1010 is configured to absorb at least a portion of the stored mechanical energy of the first optic 1032 as the optic is advanced through the opening 917 of the tubular section 902 via the plunger 920. For example, in some embodiments, as the first optic 1032 exits the lumen 910, it expands from a compacted configuration to a natural configuration. As the first optic 1032 expands, it stretches the expansion member 1010 from the constricted configuration to the expanded configuration, thereby storing mechanical energy in the expansion member 1010. In further embodiments, the expansion member 1010 can dissipate energy from the system such as, for example, in the form of a small amount of heat. Accordingly, in various embodiments, the expansion member 1010 can inhibit sudden release of mechanical energy stored in the compacted optic 1032 and slow entry of the IOL 1030 from the injector 1000.

In some embodiments, the IOL 1030 can emerge from the lumen 910 of its own accord. For example, in some embodiments, the injector 1000 does not include an expansion member 1010, and further, can include a relatively smooth, relatively rigid distal tip that deforms only slightly or not at all as the IOL 1030 progresses therethrough. In certain of such embodiments, the plunger 920 can be advanced to a point where the restorative force of the IOL 1030 begins to move the IOL 1030 from the lumen 910. In some embodiments, a smooth, rigid distal tip does not significantly slow the release of stored mechanical energy within the IOL 1030, and in some arrangements, can permit the IOL 1030 to fully emerge from the lumen 910 and, in further arrangements, to spring from the lumen 910.

In other embodiments, the injector 1000 comprises an expansion member 1010 capable of dissipating energy from the IOL 1030 over a range of movement of the plunger 920. For example, in some embodiments, the plunger 920 can be advanced to a point where a restorative force arises as the IOL 1030 emerges from the lumen 910. Stored mechanical energy that otherwise could cause the IOL 1030 to exit the lumen 910 entirely can be absorbed by the expansion member 1010, thus slowing or inhibiting egress of the IOL 1030. In some embodiments, once a portion of the IOL 1030 initially emerges from the lumen 910 and begins to release mechanical energy, the plunger 920 continues to travel through a distance in order to urge the IOL 1030 from the lumen 910. In various embodiments, this distance is no less than about 5%, no less than about 10%, no less than about 15%, no less than about 20%, or no less than about 25% the total distance traveled by the plunger 920 to advance the IOL 1030 in a distal direction.

In some embodiments, the expansion member 1010 retains the first optic 1032 until the second optic 1034 is forced into the expansion member 1010. For example, in some embodiments, the expansion member 1010 comprises a material having a relatively high coefficient of friction when in contact with the material(s) of which the first and/or second optics 1032, 1034 are composed. The expansion member 1010 can thus resist movement of the first optic 1032 as it releases stored mechanical energy to achieve its natural configuration and/or as the second optic 1032 is advanced into the expansion member 1010. Accordingly, in some embodiments, the expansion member 1010 can provide controlled delivery of the first optic 1032 to an eye.

Figure 59:
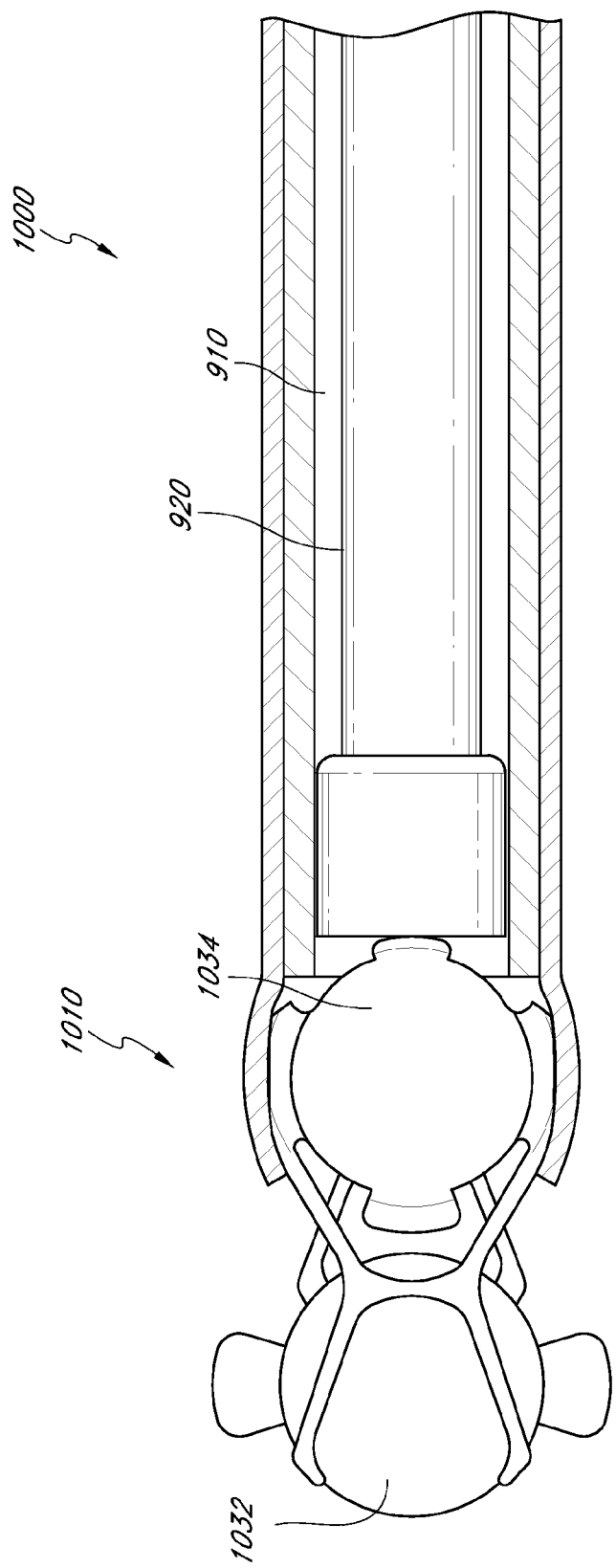
FIG. 59 is a schematic partial top cross-sectional view of the injector of FIG. 57 showing the expansion member retaining a portion of a second optic of the intraocular lens.

With reference to FIG. 59, in some embodiments, the expansion member 1010 is capable of retaining the second optic 1034 stationary after the first optic 1032 has exited the expansion member 1010. In further embodiments, the expansion member 1010 is configured retain the second optic 1034 substantially stationary relative to the injector 1000 after a substantial portion of the second optic 1034 has exited the lumen 910. For example, the expansion member 1010 can stretch to the expanded configuration as the second optic 1034 egresses the lumen 910, thereby resisting movement of the second optic 1034 out of the lumen 910. Accordingly, the plunger 920 can be used to urge the second optic 1034 from the lumen 910 in a controlled manner.

Any suitable combination of the features of the various injectors disclosed herein can be made. For example, compatible features of the injector 1000 can be combined with features of the injector 900. In some embodiments, the release control sections 912 and the expansion member 1010 can be combined in a single embodiment. As another example, in some embodiments, an expansion member 1010 can be fitted to a distal end of the tubular section 902 of the injector 900. Accordingly, a distal edge of the tubular section 902 can be angled, as illustrated in FIGS. 54A-D. In certain of such embodiments, the expansion member 1010 also is angled, and can extend longitudinally beyond the distal edge of the tubular section 902 by a substantially fixed amount.

Figure 60:
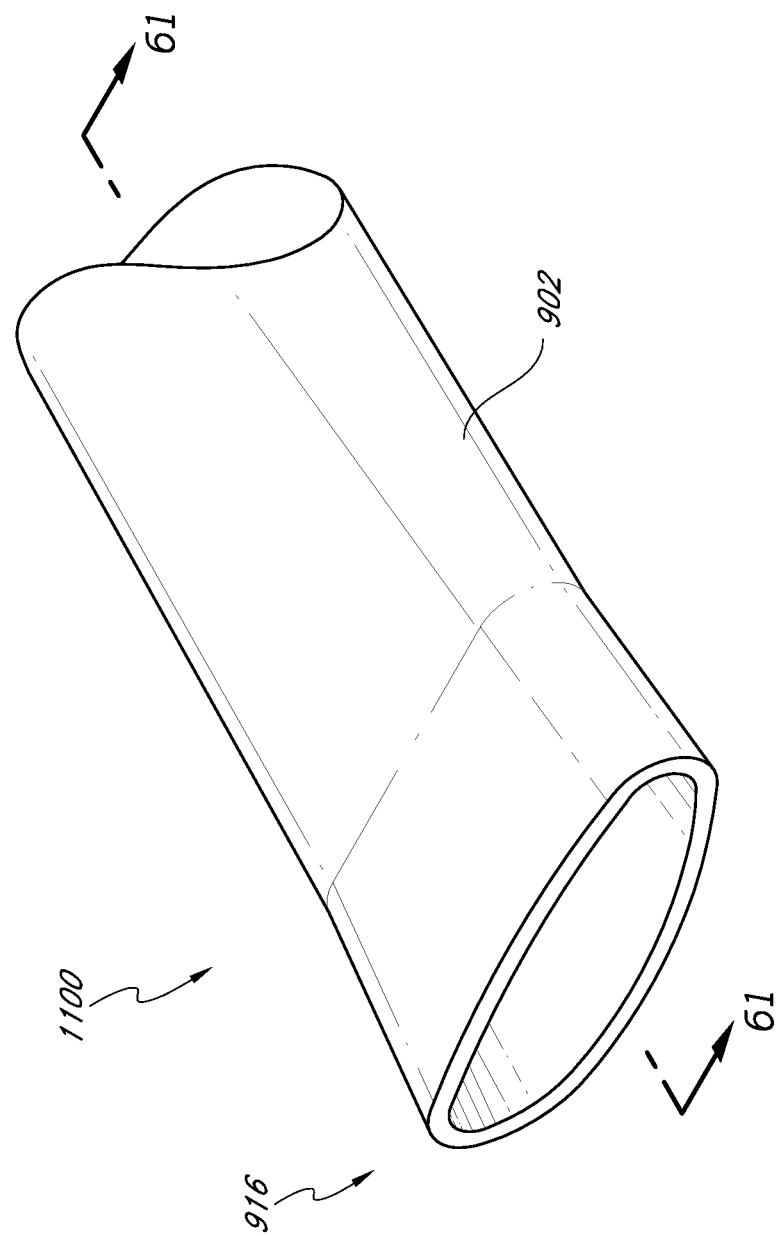
FIG. 60 is a schematic partial perspective view of an embodiment of an injector having a flattened end.

FIGS. 60 and 61 illustrate an embodiment of an injector 1100. The injector 1100 can resemble the injector 900 in many respects, and can differ in other respects such as those described hereafter. In some embodiments, the injector 1100 resembles the embodiments of the injector 900 illustrated in FIGS. 54A-D, except that the distal end 916 of the tubular section 902 is substantially flattened. For example, in some embodiments, the distal end 916 is elongated along a first plane through a longitudinal axis of the tubular section 902, and is relatively narrow along a second plane through the longitudinal axis of the tubular section 902. The first and second planes can be perpendicular to each other.

In some embodiments, the relatively narrow profile of the injector 1100 can advantageously correspond more closely with a linear incision site than can certain other profiles. Accordingly, the injector 1100 may be more easily inserted into an eye in some instances, and may provide for a smaller incision site. In some embodiments, the narrow profile can also apply a retarding pressure against an IOL being inserted in the eye, thereby slowing an exit velocity of the IOL.

A flattened profile of the distal end 916 of the injector 1100 can be achieved in any suitable manner. For example, in some embodiments, the distal end 916 is molded to include a flattened profile, and in other embodiments, the distal end 916 is heated and mechanically flattened. Other methods may also be used.

FIG. 62 illustrates another embodiment of the injector 1100. In the illustrated embodiment, a top portion 1112 and a bottom portion 1114 of the distal end 916 contact each other in at least one position. In some embodiments, the top and bottom portions 1112, 1114 are configured to separate or expand to another position to permit an IOL to pass therethrough. In some embodiments, the injector 1100 provides additional resistance to passage of an IOL than do certain embodiments of the injector 1100 illustrated in FIG. 61. The amount of separation between the top and bottom portions 1112, 1114 and/or the flexibility of the top and bottom portions 1112, 1114 can be optimized to achieve a desired degree of resistance to an IOL.

Any suitable combination of the embodiments described herein is possible. For example, any suitable combination of the embodiments described with respect to FIGS. 49-54 with the embodiments described with respect to FIGS. 55 and 56 is possible. Furthermore, any suitable combination of the embodiments described with respect to FIGS. 49-56 with any of the embodiments described with respect to FIGS. 57-62 is possible. Any suitable combination of the embodiments described with respect to FIGS. 1-48 with the various embodiments described with respect to FIGS. 49-62 is also possible.

Although the invention(s) have been disclosed in the context of certain preferred embodiments and examples, it will be understood by those skilled in the art that the invention(s) extend beyond the specifically disclosed embodiments to other alternative embodiments and/or uses of the invention(s) and obvious modifications and equivalents thereof. Thus, it is intended that the scope of the invention(s) herein disclosed should not be limited by the particular embodiments described above, but should be determined only by a fair reading of the claims that follow.

What is claimed is:

1. An injector for inserting an intraocular lens into an eye, the injector comprising:
   a lumen, said lumen comprising a terminal portion at a distal end and a proximal portion juxtaposed with said terminal portion, the terminal portion including an outlet, said lumen further comprising an inner surface; and
   an injector plunger at least partially disposed within said lumen for generating a driving force on the intraocular lens, the driving force causing the intraocular lens to move within said lumen, the lens moving through said proximal portion before said terminal portion,
   wherein the injector comprises a lens coefficient of friction between said inner surface and the intraocular lens when the lens is moving through said lumen, said lens coefficient of friction associated with a lens frictional force that resists the driving force; said lens coefficient of friction having a first value when the lens is at a first location within said proximal portion and a second value when the lens is at a second location within said terminal portion, the first value being smaller than the second value, and
   wherein a portion of the inner surface at the first location is smooth with a lubricious coating disposed thereon and a portion of the inner surface at the second location is free of the lubricious coating.

2. The injector of claim 1, wherein said lens frictional force increases as the lens approaches said distal end of said lumen.

3. The injector of claim 1, wherein said lens coefficient of friction varies gradually from said first value to said second value with the passage of the lens from said first location to said second location.

4. The injector of claim 1, wherein said lens coefficient of friction varies abruptly from said first to second lens coefficient values with the passage of the lens from said first to said second location.

5. The injector of claim 1, further comprising a tubular section defining the lumen and comprising an outer surface, the injector further comprising a low-friction coating on the outer surface near the distal end of the lumen.

6. An injector for inserting an intraocular lens into an eye, the injector comprising:
   a lumen, said lumen comprising a terminal portion at a distal end and a proximal portion juxtaposed with said terminal portion, the terminal portion including an outlet, said lumen further comprising an inner surface; and
   an injector plunger at least partially disposed within said lumen for generating a driving force on the intraocular lens, the driving force causing the intraocular lens to move within said lumen, the lens moving through said proximal portion before said terminal portion,
   wherein the injector comprises a lens coefficient of friction between said inner surface and the intraocular lens when the lens is moving through said lumen, said lens coefficient of friction associated with a lens frictional force that resists the driving force, and
   wherein said lens frictional force has a first value when the lens is at a first location within said proximal portion and a second value when the lens is at a second location within said terminal portion, the first location including a lubricious coating and the second location being free of the lubricious coating, such that the first value is smaller than the second value, said lens frictional force increasing abruptly from the first value to the second value as the lens approaches said distal end of said lumen.

7. The injector of claim 6, wherein an increase in said lens frictional force from the first value to the second value provides tactile feedback to a user that the lens is near the distal end of the lumen.

8. An injector for inserting an intraocular lens into an eye, the injector comprising:
   a lumen, said lumen comprising a terminal portion at a distal end and a proximal portion juxtaposed with said terminal portion, said lumen further comprising an inner surface; and
   an injector plunger at least partially disposed within said lumen for generating a driving force on the intraocular lens, the driving force causing the intraocular lens to move within said lumen, the lens moving through said proximal portion before said terminal portion, said plunger comprising an abutting surface in facing relationship to said inner surface,
   wherein the injector comprises a plunger coefficient of friction between said inner surface and said abutting surface when the plunger is moving through said lumen, said plunger coefficient of friction associated with a plunger frictional force that resists the driving force; said plunger frictional force having a first value when the lens is at a first location within said proximal portion and a second value when the lens is at a second location within said terminal portion, the first value being smaller than the second value, and
   wherein said plunger coefficient of friction is provided at least in part by one or more lubricious coatings selectively covering said inner surface of said lumen at the first location and wherein the second location does not have the one or more lubricious coatings.

9. The injector of claim 8, wherein said plunger frictional force increases abruptly from the first value to said second value as the lens approaches said distal end of said lumen.

10. The injector of claim 8, wherein an increase in said plunger frictional force from said first value to said second value can provide a tactile feedback to a user indicating that the lens is near the distal end of the lumen.

11. The injector of claim 8, wherein said plunger coefficient of friction has a first plunger coefficient value when the lens is at said first location and a second plunger coefficient value when the lens is at said second location, said second plunger coefficient value being larger than said first plunger coefficient value.

12. The injector of claim 11, wherein said plunger coefficient of friction varies gradually from said first value to said second value during the passage of the lens from said first location to said second location.

13. The injector of claim 11, wherein said plunger coefficient of friction varies abruptly from said first value to said second value during the passage of the lens from said first location to said second location.

14. The injector of claim 11, wherein said inner surface comprises a partially coated surface in contact with said abutting surface when the lens is at at least one of said first and second locations.

15. The injector of claim 8, further comprising a tubular section defining the lumen and comprising an outer surface, the injector further comprising a low-friction coating on the outer surface near the distal end of the lumen.

16. A method of operating an injector comprising a lumen and a plunger at least partially disposed within said lumen, said lumen comprising a terminal portion at a distal end and a proximal portion juxtaposed with said terminal portion, said lumen further comprising an inner surface, said plunger comprising an abutting surface in facing relationship to said inner surface, an intraocular lens being disposed in said injector, said method comprising:
   exerting a first plunger frictional force on the plunger when the lens is at a first location within said proximal portion, said first plunger frictional force being associated with a first plunger coefficient of friction between said abutting surface and said inner surface;
   exerting a second plunger frictional force on the plunger when the lens is at a second location within said terminal portion, said second plunger frictional force being associated with a second plunger coefficient of friction between said abutting surface and said inner surface, wherein said second plunger frictional force is larger than said first plunger frictional force, and
   wherein the plunger coefficient of friction is provided at least in part via one or more lubricious coatings selectively covering said inner surface of said lumen at the first location while not covering the second location.

17. The method of claim 16, further comprising abruptly transitioning from said first plunger frictional force to said second plunger frictional force as said intraocular lens is advanced within said lumen.

18. The method of claim 16, further comprising varying a plunger frictional force gradually from said first plunger frictional force to said second plunger frictional force during the passage of the lens from said first location to said second location.

19. The method of claim 16, further comprising providing a tactile feedback to a user of the injector via transition from said first plunger frictional force to said second plunger frictional force.

20. The method of claim 16, wherein said second plunger coefficient of friction is larger than said first plunger coefficient of friction.

* * * * *